(12) United States Patent
Mattanovich et al.

(10) Patent No.: US 11,401,523 B2
(45) Date of Patent: Aug. 2, 2022

(54) METHODS OF PRODUCING PROMOTER VARIANTS

(71) Applicant: LONZA LTD., Visp (CH)

(72) Inventors: Diethard Mattanovich, Vienna (AT); Brigitte Gasser, Vienna (AT); Michael Maurer, Vienna (AT); Roland Prielhofer, Vienna (AT); Joachim Klein, Visp (CH); Jana Wenger, Visp (CH)

(73) Assignee: LONZA LTD, Visp (CH)

( * ) Notice: Subject to any disclaimer, the term of this patent is extended or adjusted under 35 U.S.C. 154(b) by 527 days.

(21) Appl. No.: 16/293,479

(22) Filed: Mar. 5, 2019

(65) Prior Publication Data
US 2019/0185866 A1 Jun. 20, 2019

Related U.S. Application Data

(60) Division of application No. 15/335,132, filed on Oct. 26, 2016, now Pat. No. 10,301,634, which is a continuation of application No. 14/350,352, filed as application No. PCT/EP2012/069757 on Oct. 5, 2012, now Pat. No. 9,512,432.

(60) Provisional application No. 61/544,451, filed on Oct. 7, 2011.

(30) Foreign Application Priority Data

Oct. 7, 2011 (EP) .................................. 11184323
Jun. 6, 2012 (EP) .................................. 12171006

(51) Int. Cl.
| | | |
|---|---|---|
| C12N 15/81 | (2006.01) | |
| C07K 14/39 | (2006.01) | |
| C12N 15/67 | (2006.01) | |
| C07K 16/00 | (2006.01) | |
| C12N 15/63 | (2006.01) | |
| C12P 21/00 | (2006.01) | |
| C12N 9/02 | (2006.01) | |

(52) U.S. Cl.
CPC ............ *C12N 15/815* (2013.01); *C07K 14/39* (2013.01); *C07K 16/00* (2013.01); *C12N 9/0008* (2013.01); *C12N 15/635* (2013.01); *C12N 15/67* (2013.01); *C12N 15/81* (2013.01); *C12P 21/00* (2013.01); *C12Y 102/01012* (2013.01); *C07K 2317/55* (2013.01)

(58) Field of Classification Search
None
See application file for complete search history.

(56) References Cited

U.S. PATENT DOCUMENTS

| | | |
|---|---|---|
| 4,808,537 A | 2/1989 | Stroman et al. |
| 4,855,231 A | 8/1989 | Stroman et al. |
| 6,730,499 B1 | 5/2004 | Gregg et al. |
| 2008/0153126 A1 | 6/2008 | Qian et al. |
| 2008/0299616 A1* | 12/2008 | Choi ........................ C12N 9/88 435/69.2 |
| 2009/0325241 A1 | 12/2009 | Jeffries et al. |
| 2011/0021378 A1 | 1/2011 | Callewaert et al. |

FOREIGN PATENT DOCUMENTS

| | | |
|---|---|---|
| CN | 1966688 A | 5/2007 |
| EP | 0103409 A2 | 3/1984 |
| EP | 1951877 A1 | 8/2008 |
| WO | 1997/044470 A1 | 11/1997 |
| WO | 2005/003310 A2 | 1/2005 |
| WO | 2006/089329 A2 | 8/2006 |
| WO | 2007/117062 A1 | 10/2007 |
| WO | 2008/063302 A2 | 5/2008 |
| WO | 2008/128701 A2 | 10/2008 |
| WO | 2010/135678 A1 | 11/2010 |

OTHER PUBLICATIONS

Billard, et al., "Glucose uptake in Kluyveromyces lactis: Role of the HGT1 gene in glucose transport," Journal of Bacteriology 178:5860-66 (1996).
Database EMBL, 11 Pichia stipitis clone JGIAHYZ-17LI, complete sequence. 11, XP002760060, retrieved from EBI accession No. EM STD:AC 152111, Oct. 28, 2004.
Hartner F.S. et al., Nucleic Acids Research, Supplementary Data 36: 1-15 (2008).
Hoh En Blum et al., "Effects of gene dosage, promoters, and substrates on unfolded protein stress of recombinant pichia pa . . . " Biotechnology and Bioengineering 85:367-75 (2004).
Kueberl et al., "Pichia pastoris CBS 7435 chromosome 1, complete replicon sequence," XP002667184, "high quality genome sequence of picia pa . . . " Database EMBL 154:312-20 (2011).
Marx et al., "Directed gene copy number amplification in Pichia pastoris by vector integration into the ribosomal DNA locus," FEMS Yeast Res. 9:1260-70 (2009).
Mattanovich et al., "Genome, secretome and glucose transport highlight unique features of the protein . . . ", Microbial Cell factories, Biomed Central, London, NL, 8:29 (2009).
Maurer et al., "Versatile modeling and optimization of fed batch processes for the production of secreted heterologous proteins with pichi . . . " Microb Cell Fact. 5:37, (2006).
Menendez J. et al., "The ICL 1 gene of pichia pastoris, transcriptional regulation and use of its promoter" Yeast, 20:1097-108 (2003).

(Continued)

*Primary Examiner* — Christian L Fronda
(74) *Attorney, Agent, or Firm* — Medler Ferro Woodhouse & Mills PLLC

(57) ABSTRACT

A method of producing a protein of interest (POI) by culturing a recombinant eukaryotic cell line comprising an expression construct comprising a regulatable promoter and a nucleic acid molecule encoding a POI under the transcriptional control of said promoter, comprising the steps a) cultivating the cell line with a basal carbon source repressing the promoter, b) cultivating the cell line with a limited amount of a supplemental carbon source de-repressing the promoter to induce production of the POI at a transcription rate of at least 15% as compared to the native pGAP promoter, and c) producing and recovering the POI; and further an isolated regulatable promoter and a respective expression system.

12 Claims, 17 Drawing Sheets

Figure 14:
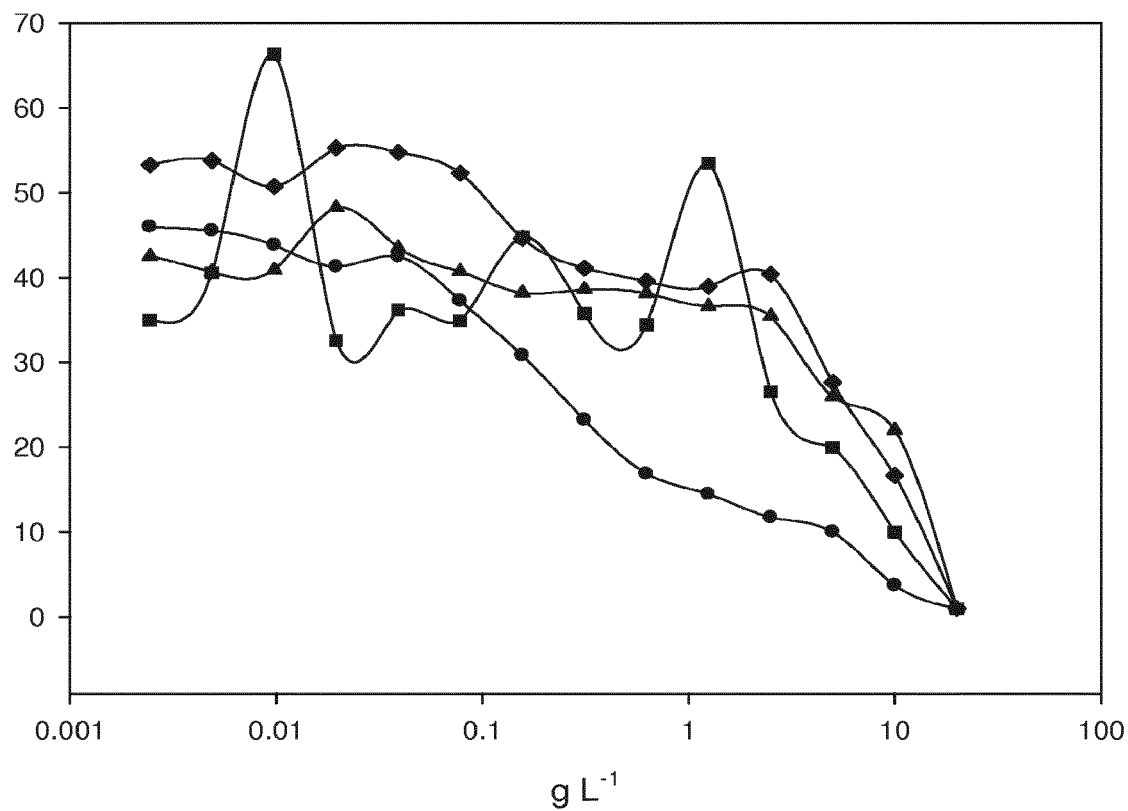

Specification includes a Sequence Listing.

(56) References Cited

OTHER PUBLICATIONS

Pichia pastoris CBS 7435 chromosome 1, complete replicon sequence, Gen Bank Accession No. FR839628 [on line], updated on Jul. 25, 2011, [retrieved on May 10, 2016].
Scholer et al., "A Carbon Source-Responsive Promoter element necessary for activation of the isocitratre lyase gene ICL 1 i . . . " Molecular and Cellular Biology 14:3613-22 (1994).
Sequence FN392322.1, from Pichia pastoris GS 115 chromosome 4, complete sequence, European Nucleotide Archive, cited in corresponding TW Appl. No. 201317350.
Stadlmayr et al., "Identification and characterisation of novel Pichia pastoris promoters for heterologous protein production," Journal of Biotechnology 150:519-29 (2010).
Zhang et al., Catabolite Repression of Aox in Pichia pastoris Is Dependent on Hexose Transporter PpHxt1 and Pexophagy, Appl. Environ. Microbial. 76:6108-6118 (2010).
EP Search Report for EP Appl. No. 11184323.1, dated May 15, 2012.
Written Opinion of the International Searching Authority. Int'l Appl. No. PCT/EP2012/069757, dated Apr. 7, 2014.
Form PCT/ISA/206, Int'l Appl. No. PCT/EP2012/069757, dated Dec. 13, 2012.
International Preliminary Report of Patentability, Int'l Appl. No. PCT/EP2012/069757, dated Oct. 8, 2013 and Response to the Written Opi . . . , dated Jun. 12, 2013.
International Search Report and the Written Opinion, Int'l Appl. No. PCT/EP2012/069757, dated Feb. 20, 2013.

\* cited by examiner

Fig. 1: pG1 (SEQ ID 1)

```
ATTTCCACCCCCATCCCAGTAGAATGTAGGGTCCCCAAACATTTGCTCCCCCTAG
TCTCCAGGGAAATGTAAAATATACTGCTAATAGAAAACAGTAAGACGCTCAGTTGT
CAGGATAATTACGTTCGACTGTAGTAAAACAGGAATCTGTATTGTTAGAAAGAACG
AGAGTTTTTTACGGCGCCGCCATATTGGGCCGTGTGAAAACAGCTTGAAACCCCA
CTACTTTCAAAGGTTCTGTTGCTATACACGAACCATGTTTAACCAACCTCGCTTTT
GACTTGACTGAAGTCATCGGTTAACAATCAAGTACCCTAGTCTGTCTGAATGCTCC
TTTCCATATTCAGTAGGTGTTTCTTGCACTTTTGCATGCACTGCGGAAGAATTAGC
CAATAGCGCGTTTCATATGCGCTTTTACCCCTCTTTTGTCAAGCGCAAAATGCCT
GTAAGATTTGGTGGGGGTGTGAGCCGTTAGCTGAAGTACAACAGGCTAATTCCCT
GAAAAAACTGCAGATAGACTTCAAGATCTCAGGGATTCCCACTATTTGGTATTCTG
ATATGTTTTCCTGATATGCATCAAAACTCTAATCTAAAACCTGAATCTCCGCTATT
TTTTTTTTTTTTTGATGACCCCGTTTTCGTGACAAATTAATTTCCAACGGGGTCTT
GTCCGGATAAGAGAATTTTGTTTGATTATCCGTTCGGATAAATGGACGCCTGCTCC
ATATTTTTCCGGTTATTACCCCACCTGGAAGTGCCCAGAATTTTCCGGGGATTACG
GATAATACGGTGGTCTGGATTAATTAATACGCCAAGTCTTACATTTTGTTGCAGTC
TCGTGCGAGTATGTGCAATAATAAACAAGATGAGCCAATTTATTGGATTAGTTGCA
GCTTGACCCCGCCATAGCTAGGCATAGCCAAGTGCTATGGGTGTTAGATGATGCA
CTTGGATGCAGTGAGTTTTGGAGTATAAAGATCCTTAAAATTCCACCCTT
```

Fig. 2: pG3 (SEQ ID 2)

GTAAATAGCGGCAGCAATCCAGTAACCTTTTCTGAATAGCAGAGCCTTAACTAAAA
TAATGGCCAGGGTAAAAAATTCGAAATTTGACACCAAAAATAAAGACTTGTCGTTA
TAAGTCTTAACAAAGTCCGCAATTTTGGAGCTAACGGTGGCGGTTGCTGGGATAT
TCAATAATGGTAGAATGTTGCTGCGGGTATATGACAGAGCGTGAAACACACTGAA
CAAGGTAAATGGAACAACAGCAATTGCAATATGGGGGAGGATAGTCAAGAACAAA
GCAGCAATGGCAAAGTACTGAATATTCTCCAAAGCCAAAAGGTCCAGTGGTTTCA
ACGACAAAGTCTTGTTGGTATAGCTTTGGAACAAAAGGACACCGAAAGACTCGAC
AGCGCCCACAAATACAGCGTTGTAGAAGAACGAATTGATTGCTCCAGAGCTTCTA
ATAGTCAGAAGATACCCCAAACCTCCGAGCAACGTTAGCACATGACCTAAGAACC
AGGCGAAGTGAAGAGTCTGGAATAACGACACCCAGTCAGTTTTTCCTGAGCTCCT
GGTGGGATTGGTAGAAGCATTTGATTTGCTTGGAGTGGTTTTATTTGAAGATGGT
GTTGAAGCCATTGTTGCTAAAGAGTCGGAGTTTTGCTTTTAGGGTTTGTTAAGCAA
AGGAGGAAAAACTGCGCCGTTTGAAGTCCCAGGTAGTTTCGCGTGTGAGGCCAG
CCAGGGAAAGCTTCCTTCGGTACTTTTTTTCTTTTGCAGGTTCCGGACGGATTAA
GCTTCGGGTTATGAGGGGGGCGGTAGCCAATTCCGGACACAATATTGCGTCGCA
GCTAGTCACCCCGCCATAAATATACGCAGGATTGAGGTAATAACATCGATAGTCTT
AGTAATTAATACAATTCAGTGGCGAATTTGGCAACATGACGTAAGGCCCACTGTTG
TCTATAAAAGGGGATGAATTTTCATGTTTTTGAGGCCTCCCGGACAATTTATTGAA
CTCAA

Fig. 3: pG4 (SEQ ID 4)

TGGACTGTTCAATTTGAAGTCGATGCTGACGATGTCAAGAGAGATGCTCAATTATA
TTTGTCATTTGCTGGTTACACTGGAAACGCTACTTTTGTTGGCGGAAACTCTACCA
GTTTGGCCGTCCATGTAAACGATGTCGTTCTGGGCCGTGACCGTTTCAACACGAA
CATAACCAATGACAAATCCACTTACAGGTCTAGTTCATATGGAGGCAATTGGTACC
TTACTTCTTTGGATGTCCCAAGTGGGGCTTTAACGTCTGGTACTAACAATGTCTCG
TTTGTCACTACAAACTCCGAGGTAAATAAGGATTCTTGTGGGATTCTCTCAAGTT
TGTTTGGAAGTTGTAACAGGTTTATAAGCATATCGTGCGCTTGTCCACAATTGAAT
CATTTATTGTTGCGAGATACATGAACAAAGTGTGAACTGGGACCCATTACTACAAT
TCCCACGCAACCGTTGTTTCAAAGCCCATATTTTTTGACAATTGTTTCGTTACACC
CCCAGTTTGATGTACATCGCTTGCAATGATGTGTGTCCCGGAGTATTTTCCATATT
CAGCTTGAATTCGTATACTCAACCAATATCTGGGGGTATACTTTTATGTAACCTATA
CAAATCAACTATACTATTTCACCTTTCGACCAATCATCTCCATCTTGTTAAGTTTT
GCTTCCTATATCCCTGACCCTGACATCACCCATGATTCCGCTCAACGGTTCTCCTC
TACATCGTCCCTCTTTTGGAGAGGGTGTTCAGTTTGACATTCAAATTACCCCCGC
CATCACGCGCAACCGAGACCGCACCCCGAATTTTCACAAATTACCCCACACCCT
ATACTCCACCACTATGAGGGTTATTAGAACTGATCACGTATAAATACCACCGCAAG
TTCCCAAGGGATCGTGTTCTTCTTCTCCAATTGCAATCATATTTCTGACTCTTTCTA
GTTCAGATTAATTCCTTTACACTTGCTTTTTCCCTTACCTTTATCC

Fig. 4: pG6 (SEQ ID 3)

AGACCAGCAGTTTAACTACGCAAATCCACAGGAATTTCTACATCACAATACCAATG
GTAATACCACGACGTCAAGGAATGGAAACGACGACTTGGAGGAAGACTTCGTCAA
CCTCTTGCGGAGTACCCGAGGCTAAGACAATAAGAAGAAAAAAAAAGAAAAGCG
GTGGGGAGGGATTATTAAATAAGGATTATGTAACCCCAGGGTACCGTTCTATAC
ATATTTAAGGATTATTTAGGACAATCGATGAAATCGGCATCAAACTGGATGGGAGT
ATAGTGTCCGGATAATCGGATAAATCATCTTGCGAGGAGCCGCTTGGTTGGTTGG
TGAGAGGAGTGAAATATGTGTCTCCTCACCCAAGAATCGCGATATCAGCACCCTG
TGGGGACACTATTGGCCTCCCTCCCAAACCTTCGATGTGGTAGTGCTTTATTAT
ATTGATTACATTGATTACATAGCTAAACCCTGCCTGGTTGCAAGTTGAGCTCCGAA
TTCCAATATTAGTAAAATGCCTGCAAGATAACCTCGGTATGGCGTCCGACCCCGC
TTAATTATTTTAACTCCTTTCCAACGAGGACTTCGTAATTTTTGATTAGGGAGTTGA
GAAACGGGGGGTCTTGATACCTCCTCGATTTCAGATCCCACCCCTCTCAGTCCC
AAGTGGGACCCCCCTCGGCCGTGAAATGCGCGCACTTTAGTTTTTTTCGCATGTA
AACGCCGGTGTCCGTCAATTAAAGTCGCAGACTAGGGTGAACTTTACCATTTTT
GTCGCACTCCGTCTCCTCGGAATAGGGGTGTAGTAATTCTGCAGTAGTGCAATTT
TTACCCCGCCAAGGGGGGGCGAAAAGAGACGACCTCATCACGCATTCTCCAGTC
GCTCTCTACGCCTACAGCACCGACGTAGTTAACTTTCTCCCATATATAAAGCAATT
GCCATTCCCCTGAAAACTTTAACCTCTGCTTTTCTTGATTTTCCTTGCCCAAAGA
AAAG

Fig. 5: pG7 (SEQ ID 5)

AATTGATTAAGTTCAGTGAAATTTCAAACCGCTATACACAACAGGACAACTTTGAG
TTTAGAAAAATCCGATGTAGTGTAACGGCTAGCACGGTCCGCTTTCACCGGGCAG
ACCCGGGTTCGACTCCCGGCATCGGAGTTTATTTTTCCATTTCGTTCTTTAGAGTA
TTCTCCTCAGCATGCCCCCTGAATTTTTCCTTTTTTCCATGTGTCCCATTTTTCCA
CTTTTTTTACAGTTTTCCTCGTGATGTTAATTGGCTACACAAAAGCTGCCACACGA
AACCTTAATCACGAAAAACTATACAGCCTTCACTAATCCGTAGCCCCATAATATGT
TGTCCACGTGCTGTTGGGTACTACCTGTAGACTCTCATACCCCACTCCGTCTTTCT
CCAACAATTAACGCAGTACCGAGATTTATCAGCAGACTCAAATTGGGCAAACTCT
GTATTTTTCCTTGCCCGCATAATTTATGGGTCTCAGGCCTCCACGTTTCCTGTTTA
CTTGAAGAATATTGGCTGCGGAAAAAGTGGTAAGGACAACCCCCTTTTAATTGGA
TCCAGTTTTTCCGAAATGTTCCGATCCGTACGTCATCTCCGAAGCCGTACATTTTC
ACTCAATCTACGTAGCTTTGGACTCAGCGCTCCTGGAATTGCCAGGACAGTTTAC
TTGAGTTGATATTCCCTTGTAGATTGTGTGCTTCTTTTTCCAAAATTTGAGGCTTCG
TTTGAAAAGTGGAATCTGGTCGCTAGATCACTTCATGCCTATTTTTCACGGAAAAA
TAAGTGGTACTATGCACCCCTTAAACCTAAAGAAAAACGGAAAAATTACCCCAAAA
CCTGGTGATGTTTTTCGCCCCTTTCTTTTTATCCGAGTTTTTCTTTTTTCTTGTCTG
CCAAATTCCTCTCCTGACCTTAGCGTCCCCGGAAAAATTAACTACTTAAGGACCG
AATGAGCCCCAGCTTTTCCCCTTCTCTTCATTATTCCCCATAATATAAT

Fig. 6: pG8 (SEQ ID 6)

CTGCACAACCATTGCCAGTAAGGACGAAGAGAAGGCCCCACTACCCAAAATTCAG
GATAACGTCTTCATACCATGCAGCGACGCCTACAAGACGCTGTCAAGACATGCCA
ACTTCAACGAAGTGAACTTTAACACATTGATCGGGAAATTGACCACCAAGGGAAT
GCTGGTTGAGGCTGGAAGCGTTGCCAGTGTCCTGAGGGAACTGGACCGAAAGTT
TAGTAATGCATAAGAGGATATATATAGGAATGCAGTAATAATATTAGTACCCATTAA
GTGGGCTAAGCCATTGGAAGGCCGTCTGACTGATGGTGGTGTTCTTCTCATTTAG
ATAGTGCATTTGCAACTACCGTCTGAGATTGAGTTTGATGTGAAGCTCCAGCGCC
AAAACAGTATAAGAACCTTATCTCCGCATTATTGTTCTTGCGTAAAAGTTTGTGTGA
AGAAACAGGGGTAGTTGCGCAGATTAGTTGTAATATGCGCATAGGATGGGTCATT
GACTTCTTTCCTCGAAAGAGCCACACCGTTAGCTAAAAAGGACGCGCATCTACC
CCAAAATAGAATGTGGGGAAATAGGACGCGCAACTTCCTCTCAATCACTGGACGT
CAGAAAAACAAATGCGCAATCGAGTCACCCTCCGTGATACCCTCCGTGATACCCC
CTCTCCGTCTATTCTGACAGCGTCTCCCCATGACGTTTCAATCTACTTAGAAAAGA
TTTCGTTTTTTTTCCTTCAATTACACGATCTCATCTTCTGCAAGGGTCTGGAGGAC
ATCACCAATCTGCGACTCCATAACTTAGTCCTGAGTTTATATTTACGCTTCATCTGA
TGAGTAGGAAGAAAAAGTTTCACGAAATTCCCCGCCAACTTGCCCTTCGGAATA
AGCAGCCACTCTCCTTCTGCCCATAGTAAGCTTGCGCGAGGCCCCAACTTGGCC
AGAAACTTTAAATATGCCAAACAATCTCCCCAATCTAAGTTCTCCCTCTTCTAAAA
A

Fig. 7: G1 (SEQ ID 7)

ATGTCCTCGTTTTTTCTAAACAACCAAACAGTAAAGATGATGACGCCTTTGGGAAG
AGCTAGAGCTCTAAATTTTCAGGGCAAAGTTTATGATAAATTTCCAAAAACTTACAA
TATCTACGCTATTGCAATAACAGCCACCGTTTCTGGACTGATGTTCGGTTTTGATA
TTTCTTCTGTGTCCTCGTTCGTAAGTCAGGATCATTACAGAAACTACTTCAACCGT
CCCGACAGTTTGACGCAAGGGGGTATCACCGCAAGTATGGCTGGAGGTTCTTTCT
TGGGTTCGTTATTTTCTTCTGACTTCCAGGATATCTTTGGAAGAAGAGTTGCTCTG
CATATGTGCAGTGTCCTCTGGATTATCGGGGCCATTCTTCAATGCGCTGCACAAA
ACCAAGGTATGCTGATCGCAGGGAGATTGATTTCCGGTATCGGTGTCGGGTTTGG
TTCAGCTTCAGCTCCAGTCTATTGTTCTGAAGTTGCTCCAGCAAAGATTAGAGGAA
TGATTGGAGGATTATTTCAATTTTCTGTCACTGTGGGTATCATGATAATGTTTTATA
TCGGATATGGATGTCACTACATTGACGGCGTTGCATCATTTAGACTGGCCTGGGG
TTTGCAAATGGTTCCAGGTCTTATTCTTTTGGTCGGTGTATTCTTCCTTCCTGAGT
CTCCAAGATGGCTGGCTAACCACAACCGCTGGGAAGACGCAGTTGAGGTTATTG
CTAATGTTGTTGCAAAAGGTGACAGAGAAAACGCCGATGTGCGTCTGCAATTGGA
TGAAGTTCAGGAGCAACTATTGATTGACAAAGATGCTTCTGATTTTGGTTACCTTG
ATTTGTTTAAGAAAGATTGTATCAAACGTACCTTCATTGGAGTGTCAGCTCAAGTG
TGGCAACAACTTTGTGGTATTAATGTTGCAATGTACTACGTTGTGTATCTCTTCCA
AATGGCTGGTTTTACTGGAAATGTGGCGTTGGTATCGTCCTCAATTCAATATGTTT
TGAATGTTGTTATGACTGTTCCAGCTTTGTTTCTAATGGACCGTATAGGCAGACGA
CCCCTACTAATTGGTGGTGGTATTTTCATGTGTATTTGGCTGTTTGGAGTGGCAG
GATTATTAGGCACTTACTCTGAACCAATTGAAAATTTCAGCGGTGATGATACTGTC
AGAATTACTATTCCTGACCAGCACAAGGCTGCAGCAAGGGGTGTTATTGCCTGTT
CCTATCTATTCGTGTGCTCCTTTGCTCCAACCTGGGGTATCTGCATTTGGGTTTAT
GCCTCTGAAATTTTCAACAACAGACAAAGAGCAAGGGAGCAGCATTTGCTGCCT
CCGCTAACTGGATTTTCAACTTTGCCTTGGCTATGTTCGTGCCATCAGCCTTTAGA
AACATTACATGGAAGACTTACATCATTTTTGGAGTATTTTCGTTCTGCTTAACAATC
CATGTTTTCTTACAATTCCCAGAAACCAGAGGTAAGACTTTGGAAGAAATTGATCA
AATGTTTAAGGACAATATTCCAGCTTGGAGAAGTGCTTCGTACGTTCCAGATATGC
CAATTTTCAACAAGAGAAGGTAGTATCTACTGAGCATGCAGAAAATGCTTCCAGC
TCGTCCGAAAAGCCTTGATGGTTCAGGAAGAGGAATCTGTATAA

Fig. 8: G3 (SEQ ID 8)

ATGGTAGTTGCAATCGAAGGTGGTACAGGCTTAGGCCTTATGAATCTTACTTGGA
AACCAACTCCAACCCCAATTGATGATGCAATTGAGACAATTAGATATGCTGTTGAG
GAAGCTGGTGTCAGATACTTGAACGGAGGAGAGTTCTACAACTTTCCTCTTGATT
CAAACCTGAATTTGCAGTACATTCAGGAATTTGCAAAAGGTACCCCGAGCTATAT
AAAAAGGTGAGTCTGTCGGTAAAAGGTGCTGTCAGTTTGGTCGATGTGAGCCCCG
ATTCTTCCCCGGAGAACCTTGAAAAATCGATTTCAAACATAACCAAACATTTGCCG
AACAACTTCCTGCCAATTTTTGAGCCTGCTAGAATCGATAAACGTTACTCCATTGA
GGAGACAATAAAGAATCTCTCTAAGTTCGTCGAAGATGGCAGAATTGGAGGTATT
TCACTTAGTGAAGTTGGTGCTGACACTATCAGAAGAGCTGCGAAAGTGGCTCCCA
TCGCCTGTGTGGAAGTGGAGTTTTCTCTATTGACTAGAGATATTCTTCATAATGGA
GTTCTTGCTGCTTGTGAGGATTTGAACATTCCTATTATTGCCTACAGTCCCTTGGG
AAGAGGATTTTTGACTGGAACGATAAACAGCAAAGCTGACATTCCTGAAGGTGAT
ATCAGGTTAAGTTTGGAAAGATTCAATGACGATGAAGTTATTGAACACAATTTGAA
ACTTGTTCACGGTTTGAAAAAGATAGCCGACAAAAAGGAGTCACATTGGCTCAAT
TGTCTCTTGCGTGGTTACGAAAGTTTGGAGATAAACACGTCAAGGTGCTTCCTATT
CCAAGCTGCTCATCTCCTCGTAGAGTTGCAGAAAACACAAAAGAGATTTCCTTGA
CTGATAGCGAGTTCCAGGAGATTACTGACTTTGCAGAGTCGGTTCCAATCAAAGG
TGGTCGTTACAACAAAGCAAGTGAGGCTGTTCTTAACGGTTAG

Fig. 9: G4 (SEQ ID 9)

```
ATGACATTTGCTCCTCCCTTAGAATTCGAGATTGACCTTCCTAACGGATTGAAGTA
CACTCAACCATTGGGACTCTTCATCAACAATGAGTTTGTTGAAGGTGTAGAGGGA
AAGCTCTTACCAGTGATCAATCCTTGTGATGAGACTAAAATAACCCAAGTTTGGGA
AGCTTCTGCAGCGGATGTTGACCGTGCTGTTGATGCCGCTGAAGATGCTTTCAAC
AACTCCGTATGGGCTACTCAGGACCCATTAGAGAGGGGAAAGCTGATGAACAAAT
TGGCAGACCTTATCGATCGTGACTTCAACATCTTGGCTGGTATCGAATCCATCGA
CAATGGTAAGGCCTATACCTCTGCCCAGGGTGATGTTACTCTTGCTGTCAACTAC
ATCAGATCCTGTGCTGGATGGGCCGACAAGATTTTGGGAAACGTTGTTGATTCCG
GAAACACCCACCTTAACTTGGTTAAAAGAGAGCCATTGGGTGTTGTGGGACAAAT
TATCCCATGGAACTTTCCTCTCCTGATGTTGGCTTGGAAGTTGGGACCTGCGCTG
GCCACAGGTAACACTGTTGTTTTGAAGACTGCCGAGTCTACCCCTCTGTCGGGTT
TATACGTTGCCAAATTGATCAAGGAGGCCGGTTTCCCACCTGGTGTGGTTAACAT
TCTCAGTGGTTTCGGTAACCCAGCTGGAGCTGCCATCGCTGCTCATCCCAGAATC
AAGAAGATTGCTTTCACCGGATCCACTGCAACAGGCCGTAAGATCATGGAAGCAG
CCGCTAAATCTAACCTGAAAAAGTCACTTTGGAACTAGGTGGTAAATCTCCAAAC
ATTGTGTTTGAAGATGCTGATATCCAGAAGACTATCCATAACATTATTTTGGGAAT
CTTCTTCAATTCTGGTGAAGTCTGTTGTGCAGGTTCCAGAGTCTACATTCAAGACA
CTGTGTATGAAGAAGTGCTTGAAGCCTTCAAGAAGGAGACTGATAACGTTAAGGT
TGGTGGACCATTCGAAGAAGGTGTCTTCCAAGGGCCTCAGACCTCTGAGTTGCAA
CTTAACAGAATCCTTAGTTACATCAAACACGGTAAGGATGAAGGTGCTCGTGTAAT
TACCGGTGGTTCAAGATACCGTAACCGAGGTTACTACATTAAGCCCACAATTTTTG
CTGACGTTACTGAAGACATGAAGATTGTCAAGGAGGAGATTTTGGTCCTGTGGT
TACTATCACTAAGTTCTCTACCGTGGATGAGGTTGTTGGATATGCCAACAACACCA
ACTATGGTCTAGCTGCTGGTATTCACACAAACAACTTGAACAAAGCCATTGATGTT
GCCAGTAGAATCAAGGCGGGTGTCGTTTGGATTAACACCTACAACGATTTCCACC
ACATGGTTCCTTTCGGAGGTTATGGAGAATCTGGTATTGGCAGAGAGCTTGGTGC
TGAGGCTTTGGATAACTACACTCAAGCCAAGGCTATCAGAATTGCTTACACTCCTG
AACATAAGTAG
```

Fig. 10: G6 (SEQ ID 10)

```
ATGCTTAGAACTTCTCCAGCTACTAAGAAAGCTCTCAAGTCGCAGATTAACGCCTT
CAACGTTGCTGCCTTGAGATTCTACTCCTCATTGCCTTTGCAGGTTCCAATTACCT
TGCCAAACGGTAAGACCTACAATCAGCCAACAGGTTTGTTTATCAACAATGAGTTC
GTTCCTTCTAAGCAAGGTAAGACCTTTGCTGTTTTAAACCCTTCCACTGAGGAGGA
GATTACTCACGTCTACGAGTCCAGAGAGGACGACGTTGAGTTAGCCGTTGCAGC
CGCTCAAAAGGCTTTCGACTCAACCTGGTCCACCCAGGACCCTGCTGAGAGAGG
TAAGGTCTTGAACAAGTTGGCTGACCTGATCGAGGAGCACTCTGAGACCCTTGCC
GCCATCGAGTCCTTGGACAACGGTAAGGCCATTTCCTCCGCTAGAGGTGATGTTG
GTCTGGTTGTCGCCTACTTGAAGTCCTGTGCCGGTTGGGCCGACAAGGTTTTCG
GTAGAGTTGTTGAAACCGGAAGCTCCCACTTCAACTACGTTAGAAGAGAGCCATT
GGGTGTTTGTGGTCAGATTATCCCATGGAACTTTCCTCTTCTGATGTGGTCCTGG
AAAGTTGGTCCAGCTTTGGCCACTGGTAACACTGTTGTCCTGAAGACAGCCGAGT
CTACTCCTCTGTCCGCCCTGTACGTTTCCCAATTGGTCAAGGAGGCCGGTATCCC
AGCTGGTGTCCACAACATTGTGTCCGGTTTCGGTAAGATTACTGGTGAAGCTATT
GCTACTCATCCTAAGATCAAGAAGGTTGCCTTCACTGGTTCTACCGCCACTGGTC
GTCACATCATGAAGGCTGCTGCCGAATCCAACTTGAAGAAGGTTACTTTGGAGTT
GGGTGGTAAATCTCCTAACATCGTGTTCAACGATGCTAACATTAAGCAAGCTGTC
GCCAACATCATCCTCGGTATTTACTACAACTCTGGAGAAGTTTGTTGTGCTGGTTC
CAGAGTTTATGTTCAATCCGGTATTTACGACGAGCTTTTGGCCGAATTCAAGACTG
CTGCTGAGAATGTCAAGGTTGGTAACCCATTCGACGAGGACACCTTCCAAGGTGC
TCAAACCTCTCAGCAACAATTGGAGAAGATTTTGGGTTTCGTTGAGCGTGGTAAG
AAGGACGGTGCTACTTTGATTACTGGTGGTGGCAGATTAGGTGACAAGGGTTACT
TCGTCCAGCCAACTATCTTCGGTGATGTTACACCAGAGATGGAGATTGTCAAGGA
AGAGATCTTTGGTCCTGTTGTCACTATCAGCAAGTTTGACACCATTGATGAGGTTG
TCGACCTTGCTAACGACTCTCAATACGGTCTTGCTGCTGGTATCCACTCTGACGA
TATCAACAAGGTCATTGACGTTGCTGCTAGAATCAAGTCCGGTACCGTGTGGGTC
AACACCTACAACGATTTCCACCAAATGGTTCCATTCGGTGGATTTGGCCAATCCG
GTATTGGTCGTGAGATGGGTGTTGAAGCTTTGGAAAACTACACCCAATACAAGGC
TATCCGTGTCAAGATCAACCACAAGAACGAGTAA
```

Fig. 11: G7 (SEQ ID 11)

ATGAGTTCAACAGATATCCAAGGTGATCAAGGTGACAATGAAAAGATATACGCCA
TTGAGAGCAGTCCCTCCAATGAGCAAATAAAAGATATTCATGAGGCTCCGGCCGA
CAACAAAAGTGAACTAGACATCCCAGTCAAACCCAAGGGTTCCTATATCTTGGTGT
CTGTGTTATGTCTTCTAGTCGCATTCGGTGGTTTCGTGTTCGGTTGGGATACCGG
TACCATCTCAGGTTTCGTTAACATGTCTGACTTTACGAGACGTTTCGGACAGTTTA
ACGGTGAAACGTATTACCTTTCTAAAGTGAGAGTTGGTTTAATTGTTTCTATTTTCA
ACATTGGTTGTGCTATCGGAGGTGTCACTCTAGGTAAACTTGGTGACATTTGGGG
TAGAAAGAAGGCTTTGATGTTCGTCATGGTCATCTATATGGTCGGTATTTTGATTC
AAATTGCTTCCATTGACAAATGGTACCAGTATTTCATTGGAAGAATTATTGCAGGT
CTGGCCGTCGGTGCAGTTTCCGTTTTATCCCCATGTTCATCAGTGAGACTTCTC
CTAAACACATCAGAGGTTCCTTAGTCTCCTGCTACCAATTAATGATTACAGCCGGT
ATTTTCTTGGGTTACTGTACCACTTACGGAACCAAGACTTACACCGACTCCACCCA
ATGGAGAGTTCCTTTGGGATTGTGTTTCGCTTGGGCCATTCTGATGATTGTTGGTA
TGACCTTCATGCCAGAGTCCCCACGTTTCTTGGTTGAGGTTAACAGAGTCGACGA
GGCTATGAAGTCCATTGCCAGAGTTAACAAGGTCTCTATCGACGATCCATCTGTC
TACAATGAGATGAGACTTATTTCTGACGGTATTGAGAAGGAGAAGGAGGCTGGTA
GCGTTTCTTGGGGTGAACTGTTCACTGGTAAGCCAAAGATTTTCTACCGTCTATTG
ATTGGTATTTTCATGCAATCTTTGCAACAATTGACCGGTAACAACTATTTCTTCTAC
TACGGAACTACCATTTTCAAGGCTGTCGGATTGGACGATTCTTTCCAAACTTCTAT
CATTCTTGGTGTTGTCAATTTTGCTTCCACATTCCTAGGTATCTACACCATGGATAA
ATTTGGTAGAAGAAGAACACTTTTAGGAGGTTCTGGAGCCATGGTTGTTTGTTTGG
TCATTTTCAGTTCCGTTGGTGTCAAGTCTCTTTATGAGAACGGTAAGGATGATCCA
TCCAAACCAGCAGGTAACGCCATGATTGTCTTCACCTGTCTGTTCATTTTCTTCTT
TGCATGTACCTGGGCTCCAGGTGTTTTCGTCGTTGTGTCTGAAACCTACCCACTT
AGAATTAGATCCAAGGGTATGGCCATCGCTCAAGGTTCCAATTGGCTTTGGGGTT
TCCTCATTGCCTTCTTCACTCCATTTATCTCAGGTGCCATTGATTTCGCCTACGGT
TACGTCTTTATGGGATGTACTCTGTTCGCCTTCTTCTTTGTGTACTTCTTCGTTCCT
GAAACCAAGGGTCTGTCGCTGGAAGACGTTGATGAAGTCTATGAGAACCTTACCT
TCGGAAGAGCATATGCATACAGCCACACGATTAAAGACAAGGGCGCCCTATAA

Fig. 12: G8 (SEQ ID 12)

```
ATGGCCCTATCTCCTACCTATCAGGGCTACATATCTACCACTGGCGACGCGTTGA
TCGTGATCCAGGCAGCTCTAAATAACCATTTGAATCTTCTTCCCCGAAGACCAAGA
GAAAGAGAGCGAGATGGGCTAATACGATCAGGTAACGTATTTGTTTTTGTCGAGC
AACGGTCTCATATCAAACGATGGACCGATGGTATCCCCTGGTCTCCATCTAGAGT
CCTTGGAAAGTTCTTGTTGTATCGGGAACTGGACAAGGATACCCCCAAAAACTCG
CAAAGTGACGAAGATACTGAGGAGGGGAGAAAGAGGCGAAAGACTTCTGTGGAT
GTAACCGATCCAAATACCAGGCAGTTGGTGGGATCATTGGTGACTTCCTATGACT
TCAAAGAGGATGGACTTATTAAAAAACACTCTCCTTGACTTTCCAGACCGGTGCT
AATGAAGAAAGGGAAACAGTGCACTTGATTAGTTATTATACTCCGGAAGATGTAAC
GAACCATCGTTTGAACAGGCCGTCTGACAATCCATATCTGGCCAATATCACTGTTT
CAGAGTCATTATTGACTGCCTTGAGAGAGAGTACCCTTGGAGGAAGAGCAACGTC
TGATGACGAGCTTTCTTTAGTCAGAAGTAACTCGTTAGAGTACCAAGAGGTACCAA
TGAACATATCTATGTCTTTACCTTTATCAACTCCACTTTCCTTGAACACAGGAGTAA
ACTCAACTACCCAGCTGCAACAGCAACAACTACAACAACAACAACAGCAACAGCA
ACAGCAGCAGCAACAACAGCAGCAACAACAGCAACCGGTAGCATCCCTTCCAAA
ATTTGATGGATCCTTTCTATTACAACAGGGTGTAATTCCAGTTCCTCATTTCATGGA
CCAAAAAATGGGAAGTAGCAATTCGTGGATTAACAATTGGTTTCGTCCAAATTCGT
CAGAATCAAATGGGCTATCGGTTATCGGACCTCACAAGGGATATGACGAACAAAG
TCCAGCAACGAGTTATACTTTGAATGAACGTTGA
```

Fig. 13: pGAP (SEQ ID 13)

```
CTTTTTTGTAGAAATGTCTTGGTGTCCTCGTCCAATCAGGTAGCCATCTCTGAAAT
ATCTGGCTCCGTTGCAACTCCGAACGACCTGCTGGCAACGTAAAATTCTCCGGGG
TAAAACTTAAATGTGGAGTAATGGAACCAGAAACGTCTCTTCCCTTCTCTCTCCTT
CCACCGCCCGTTACCGTCCCTAGGAAATTTTACTCTGCTGGAGAGCTTCTTCTAC
GGCCCCCTTGCAGCAATGCTCTTCCCAGCATTACGTTGCGGGTAAAACGGAGGT
CGTGTACCCGACCTAGCAGCCCAGGGATGGAAAAGTCCCGGCCGTCGCTGGCAA
TAATAGCGGGCGGACGCATGTCATGAGATTATTGGAAACCACCAGAATCGAATAT
AAAAGGCGAACACCTTTCCCAATTTTGGTTTCTCCTGACCCAAAGACTTTAAATTT
AATTTATTTGTCCCTATTTCAATCAATTGAACAACTATCACCTGCAGGCC
```

Fig. 15 pG1a (SEQ ID 41)

GGAATCTGTATTGTTAGAAAGAACGAGAGTTTTTTACGGCGCCGCCATATTGGGC
CGTGTGAAAACAGCTTGAAACCCCACTACTTTCAAAGGTTCTGTTGCTATACACGA
ACCATGTTTAACCAACCTCGCTTTTGACTTGACTGAAGTCATCGGTTAACAATCAA
GTACCCTAGTCTGTCTGAATGCTCCTTTCCATATTCAGTAGGTGTTTCTTGCACTT
TTGCATGCACTGCGGAAGAATTAGCCAATAGCGCGTTTCATATGCGCTTTTACCC
CCTCTTTTGTCAAGCGCAAAATGCCTGTAAGATTTGGTGGGGGTGTGAGCCGTTA
GCTGAAGTACAACAGGCTAATTCCCTGAAAAAACTGCAGATAGACTTCAAGATCTC
AGGGATTCCCACTATTTGGTATTCTGATATGTTTTCCTGATATGCATCAAAACTCT
AATCTAAAACCTGAATCTCCGCTATTTTTTTTTTTTTTGATGACCCCGTTTTCGT
GACAAATTAATTTCCAACGGGGTCTTGTCCGGATAAGAGAATTTTGTTTGATTATC
CGTTCGGATAAATGGACGCCTGCTCCATATTTTCCGGTTATTACCCCACCTGGAA
GTGCCCAGAATTTTCCGGGGATTACGGATAATACGGTGGTCTGGATTAATTAATA
CGCCAAGTCTTACATTTTGTTGCAGTCTCGTGCGAGTATGTGCAATAATAAACAAG
ATGAGCCAATTTATTGGATTAGTTGCAGCTTGACCCCGCCATAGCTAGGCATAGC
CAAGTGCTATGGGTGTTAGATGATGCACTTGGATGCAGTGAGTTTTGGAGTATAA
AAGATCCTTAAAATTCCACCCTT

Fig. 15 (continued)

pG1b (SEQ ID 42)

CCATATTCAGTAGGTGTTTCTTGCACTTTTGCATGCACTGCGGAAGAATTAGCCAA
TAGCGCGTTTCATATGCGCTTTTACCCCCTCTTTTGTCAAGCGCAAAATGCCTGTA
AGATTTGGTGGGGGTGTGAGCCGTTAGCTGAAGTACAACAGGCTAATTCCCTGAA
AAAACTGCAGATAGACTTCAAGATCTCAGGGATTCCCACTATTTGGTATTCTGATA
TGTTTTTCCTGATATGCATCAAAACTCTAATCTAAAACCTGAATCTCCGCTATTTTT
TTTTTTTTTTGATGACCCCGTTTTCGTGACAAATTAATTTCCAACGGGGTCTTGTC
CGGATAAGAGAATTTTGTTTGATTATCCGTTCGGATAAATGGACGCCTGCTCCATA
TTTTTCCGGTTATTACCCCACCTGGAAGTGCCCAGAATTTTCCGGGGATTACGGA
TAATACGGTGGTCTGGATTAATTAATACGCCAAGTCTTACATTTTGTTGCAGTCTC
GTGCGAGTATGTGCAATAATAAACAAGATGAGCCAATTTATTGGATTAGTTGCAGC
TTGACCCCGCCATAGCTAGGCATAGCCAAGTGCTATGGGTGTTAGATGATGCACT
TGGATGCAGTGAGTTTTGGAGTATAAAGATCCTTAAAATTCCACCCTT pG1c (SEQ ID 43)

CTGCAGATAGACTTCAAGATCTCAGGGATTCCCACTATTTGGTATTCTGATATGTT
TTTCCTGATATGCATCAAAACTCTAATCTAAAACCTGAATCTCCGCTATTTTTTTTT
TTTTTTGATGACCCCGTTTTCGTGACAAATTAATTTCCAACGGGGTCTTGTCCGGA
TAAGAGAATTTTGTTTGATTATCCGTTCGGATAAATGGACGCCTGCTCCATATTTTT
CCGGTTATTACCCCACCTGGAAGTGCCCAGAATTTTCCGGGGATTACGGATAATA
CGGTGGTCTGGATTAATTAATACGCCAAGTCTTACATTTTGTTGCAGTCTCGTGCG
AGTATGTGCAATAATAAACAAGATGAGCCAATTTATTGGATTAGTTGCAGCTTGAC
CCCGCCATAGCTAGGCATAGCCAAGTGCTATGGGTGTTAGATGATGCACTTGGAT
GCAGTGAGTTTTGGAGTATAAAGATCCTTAAAATTCCACCCTT

Fig. 15 (continued)

pG1d (SEQ ID 44)

GACCCCGTTTTCGTGACAAATTAATTTCCAACGGGGTCTTGTCCGGATAAGAGAA
TTTTGTTTGATTATCCGTTCGGATAAATGGACGCCTGCTCCATATTTTCCGGTTAT
TACCCCACCTGGAAGTGCCCAGAATTTTCCGGGGATTACGGATAATACGGTGGTC
TGGATTAATTAATACGCCAAGTCTTACATTTTGTTGCAGTCTCGTGCGAGTATGTG
CAATAATAAACAAGATGAGCCAATTTATTGGATTAGTTGCAGCTTGACCCCGCCAT
AGCTAGGCATAGCCAAGTGCTATGGGTGTTAGATGATGCACTTGGATGCAGTGAG
TTTTGGAGTATAAAGATCCTTAAAATTCCACCCTT pG1e (SEQ ID 45)

CCGGATAAGAGAATTTTGTTTGATTATCCGTTCGGATAAATGGACGCCTGCTCCAT
ATTTTTCCGGTTATTACCCCACCTGGAAGTGCCCAGAATTTTCCGGGGATTACGG
ATAATACGGTGGTCTGGATTAATTAATACGCCAAGTCTTACATTTTGTTGCAGTCT
CGTGCGAGTATGTGCAATAATAAACAAGATGAGCCAATTTATTGGATTAGTTGCAG
CTTGACCCCGCCATAGCTAGGCATAGCCAAGTGCTATGGGTGTTAGATGATGCAC
TTGGATGCAGTGAGTTTTGGAGTATAAAGATCCTTAAAATTCCACCCTT pG1f (SEQ ID 46)

GCCTGCTCCATATTTTTCCGGTTATTACCCCACCTGGAAGTGCCCAGAATTTTCCG
GGGATTACGGATAATACGGTGGTCTGGATTAATTAATACGCCAAGTCTTACATTTT
GTTGCAGTCTCGTGCGAGTATGTGCAATAATAAACAAGATGAGCCAATTTATTGGA
TTAGTTGCAGCTTGACCCCGCCATAGCTAGGCATAGCCAAGTGCTATGGGTGTTA
GATGATGCACTTGGATGCAGTGAGTTTTGGAGTATAAAGATCCTTAAAATTCCAC
CCTT

SEQUENCE LISTING

<160> NUMBER OF SEQ ID NOS: 46

<210> SEQ ID NO 1
<211> LENGTH: 1001
<212> TYPE: DNA
<213> ORGANISM: Pichia pastoris

<400> SEQUENCE: 1

```
atttccaccc ccatcccagt agaatgtagg gtccccaaac atttgctccc cctagtctcc      60
agggaaatgt aaaatatact gctaatagaa aacagtaaga cgctcagttg tcaggataat     120
tacgttcgac tgtagtaaaa caggaatctg tattgttaga aagaacgaga gttttttacg     180
gcgccgccat attgggccgt gtgaaaacag cttgaaaccc cactactttc aaaggttctg     240
ttgctataca cgaaccatgt ttaaccaacc tcgcttttga cttgactgaa gtcatcggtt     300
aacaatcaag taccctagtc tgtctgaatg ctcctttcca tattcagtag gtgtttcttg     360
cacttttgca tgcactgcgg aagaattagc caatagcgcg tttcatatgc gcttttaccc     420
cctcttttgt caagcgcaaa atgcctgtaa gatttggtgg gggtgtgagc cgttagctga     480
agtacaacag gctaattccc tgaaaaaact gcagatagac ttcaagatct cagggattcc     540
cactatttgg tattctgata tgttttttcct gatatgcatc aaaactctaa tctaaaacct     600
gaatctccgc tattttttttt ttttttttga tgaccccgtt tcgtgacaa attaatttcc      660
aacgggtct tgtccggata agagaatttt gtttgattat ccgttcggat aaatggacgc      720
ctgctccata ttttttccggt tattacccca cctggaagtg cccagaattt tccggggatt     780
acggataata cggtggtctg gattaattaa tacgccaagt cttacatttt gttgcagtct     840
cgtgcgagta tgtgcaataa taaacaagat gagccaattt attggattag ttgcagcttg     900
accccgccat agctaggcat agccaagtgc tatgggtgtt agatgatgca cttggatgca     960
gtgagttttg gagtataaaa gatccttaaa attccaccct t                        1001
```

```
<210> SEQ ID NO 2
<211> LENGTH: 1000
<212> TYPE: DNA
<213> ORGANISM: Pichia pastoris

<400> SEQUENCE: 2
gtaaatagcg gcagcaatcc agtaaccttt tctgaatagc agagccttaa ctaaaataat      60
ggccagggta aaaaattcga aatttgacac caaaaataaa gacttgtcgt tataagtctt     120
aacaaagtcc gcaattttgg agctaacggt ggcggttgct gggatattca ataatggtag     180
aatgttgctg cgggtatatg acagagcgtg aaacacactg aacaaggtaa atggaacaac     240
agcaattgca atatggggga ggatagtcaa gaacaaagca gcaatggcaa agtactgaat     300
attctccaaa gccaaaaggt ccagtggttt caacgacaaa gtcttgttgg tatagctttg     360
gaacaaaagg acaccgaaag actcgacagc gcccacaaat acagcgttgt agaagaacga     420
attgattgct ccagagcttc taatagtcag aagataccc aaacctccga gcaacgttag     480
cacatgacct aagaaccagg cgaagtgaag agtctggaat aacgacaccc agtcagtttt     540
tcctgagctc ctggtgggat tggtagaagc atttgatttg cttggagtgg ttttatttga     600
agatggtgtt gaagccattg ttgctaaaga gtcggagttt tgcttttagg gtttgttaag     660
caaaggagga aaaactgcgc cgtttgaagt cccaggtagt ttcgcgtgtg aggccagcca     720
gggaaagctt ccttcggtac ttttttttct tttgcaggtt ccggacggat taagcttcgg     780
gttatgaggg gggcggtagc caattccgga cacaatattg cgtcgcagct agtcaccccg     840
ccataaatat acgcaggatt gaggtaataa catcgatagt cttagtaatt aatacaattc     900
agtggcgaat ttggcaacat gacgtaaggc ccactgttgt ctataaaagg ggatgaattt     960
tcatgttttt gaggcctccc ggacaattta ttgaactcaa                          1000

<210> SEQ ID NO 3
<211> LENGTH: 1001
<212> TYPE: DNA
<213> ORGANISM: Pichia pastoris

<400> SEQUENCE: 3
agaccagcag tttaactacg caaatccaca ggaatttcta catcacaata ccaatggtaa      60
taccacgacg tcaaggaatg gaaacgacga cttggaggaa gacttcgtca acctcttgcg     120
gagtacccga ggctaagaca ataagaagaa aaaaaaaaga aaagcggtgg gggagggatt     180
attaaataag gattatgtaa ccccagggta ccgttctata catatttaag gattatttag     240
gacaatcgat gaaatcggca tcaaactgga tgggagtata gtgtccggat aatcggataa     300
atcatcttgc gaggagccgc ttggttggtt ggtgagagga gtgaaatatg tgtctcctca     360
cccaagaatc gcgatatcag caccctgtgg gggacactat tggcctccct cccaaacctt     420
cgatgtggta gtgctttatt atattgatta cattgattac atagctaaac cctgcctggt     480
tgcaagttga gctccgaatt ccaatattag taaaatgcct gcaagataac ctcggtatgg     540
cgtccgaccc cgcttaatta ttttaactcc tttccaacga ggacttcgta attttgatt      600 agggagttga gaaacggggg gtcttgatac ctcctcgatt tcagatccca ccccctctca     660
gtcccaagtg ggacccccct cggccgtgaa atgcgcgcac tttagttttt ttcgcatgta     720
aacgccggtg tccgtcaatt aaaagtcgca gactagggtg aactttacca ttttttgtcgc    780 actccgtctc ctcggaatag gggtgtagta attctgcagt agtgcaattt ttaccccgcc     840
aagggggggc gaaaagagac gacctcatca cgcattctcc agtcgctctc tacgcctaca     900
```

| | |
|---|---|
| gcaccgacgt agttaacttt ctcccatata taaagcaatt gccattcccc tgaaaacttt | 960 |
| aacctctgct tttcttgat tttccttgc ccaaagaaaa g | 1001 |

<210> SEQ ID NO 4
<211> LENGTH: 1000
<212> TYPE: DNA
<213> ORGANISM: Pichia pastoris

<400> SEQUENCE: 4

| | |
|---|---|
| tggactgttc aatttgaagt cgatgctgac gatgtcaaga gagatgctca attatatttg | 60 |
| tcatttgctg gttacactgg aaacgctact tttgttggcg aaactctac cagtttggcc | 120 |
| gtccatgtaa acgatgtcgt tctgggccgt gaccgtttca cacgaacat aaccaatgac | 180 |
| aaatccactt acaggtctag ttcatatgga ggcaattggt accttacttc tttggatgtc | 240 |
| ccaagtgggg ctttaacgtc tggtactaac aatgtctcgt tgtcactac aaactccgag | 300 |
| gtaaataaag gattcttgtg ggattctctc aagtttgttt ggaagttgta acaggtttat | 360 |
| aagcatatcg tgcgcttgtc cacaattgaa tcatttattg ttgcgagata catgaacaaa | 420 |
| gtgtgaactg ggacccatta ctacaattcc cacgcaaccg ttgtttcaaa gcccatattt | 480 |
| tttgacaatt gtttcgttac accccagtt tgatgtacat cgcttgcaat gatgtgtgtc | 540 |
| ccggagtatt ttccatattc agcttgaatt cgtatactca accaatatct gggggtatac | 600 |
| ttttatgtaa cctatacaaa tcaactatac tatttcacct ttcgaccaat catctcccat | 660 |
| cttgttaagt tttgcttcct atatccctga ccctgacatc acccatgatt ccgctcaacg | 720 |
| gttctcctct acatcgtccc tcttttggag agggtgttca gtttgacatt caaattaccc | 780 |
| cccgccatca cgcgcaaccg agaccgcacc cccgaatttt cacaaattac cccacaccct | 840 |
| atactccacc actatgaggg ttattagaac tgatcacgta taaataccac cgcaagttcc | 900 |
| caagggatcg tgttcttctt ctccaattgc aatcatattt ctgactcttt ctagttcaga | 960 |
| ttaattcctt tacacttgct tttttcccctt acctttatcc | 1000 |

<210> SEQ ID NO 5
<211> LENGTH: 1000
<212> TYPE: DNA
<213> ORGANISM: Pichia pastoris

<400> SEQUENCE: 5

| | |
|---|---|
| aattgattaa gttcagtgaa atttcaaacc gctatacaca acaggacaac tttgagttta | 60 |
| gaaaaatccg atgtagtgta acggctagca cggtccgctt tcaccgggca gacccgggtt | 120 |
| cgactcccgg catcggagtt tattttcca tttcgttctt tagagtattc tcctcagcat | 180 |
| gcccccctga attttccctt ttttccatgt gtcccatttt tccactttt ttacagtttt | 240 |
| cctcgtgatg ttaattggct acacaaaagc tgccacacga aaccttaatc acgaaaaact | 300 |
| atacagcctt cactaatccg tagccccata atatgttgtc cacgtgctgt tgggtactac | 360 |
| ctgtagactc tcatacccca ctccgtcttt ctccaacaat taacgcagta ccgagattta | 420 |
| tcagcagact caaattgggc aaactctgta ttttccttg cccgcataat ttatgggtct | 480 |
| caggcctcca cgtttcctgt ttacttgaag aatattggct gcggaaaaag tggtaaggac | 540 |
| aaccccttt taattggatc cagtttttcc gaaatgttcc gatccgtacg tcatctccga | 600 |
| agccgtacat tttcactcaa tctacgtagc tttggactca gcgctcctgg aattgccagg | 660 |
| acagtttact tgagttgata ttcccttgta gattgtgtgc ttcttttcc aaaatttgag | 720 |
| gcttcgtttg aaaagtggaa tctggtcgct agatcacttc atgcctattt ttcacggaaa | 780 |

```
aataagtggt actatgcacc ccttaaacct aagaaaaac ggaaaaatta ccccaaaacc      840
tggtgatgtt tttcgcccct ttcttttat ccgagttttt cttttttctt gtctgccaaa      900
ttcctctcct gaccttagcg tccccggaaa aaattaacta cttaaggacc gaatgagccc      960
cagcttttcc ccttctcttc attattcccc ataatataat                          1000
```

<210> SEQ ID NO 6
<211> LENGTH: 1000
<212> TYPE: DNA
<213> ORGANISM: Pichia pastoris

<400> SEQUENCE: 6

```
ctgcacaacc attgccagta aggacgaaga gaaggcccca ctacccaaaa ttcaggataa       60
cgtcttcata ccatgcagcg acgcctacaa gacgctgtca agacatgcca acttcaacga     120
agtgaacttt aacacattga tcgggaaatt gaccaccaag ggaatgctgg ttgaggctgg     180
aagcgttgcc agtgtcctga gggaactgga ccgaaagttt agtaatgcat aagaggatat     240
atataggaat gcagtaataa tattagtacc cattaagtgg gctaagccat ggaaggccg     300 tctgactgat ggtggtgttc ttctcattta gatagtgcat ttgcaactac cgtctgagat     360
tgagtttgat gtgaagctcc agcgccaaaa cagtataaga accttatctc cgcattattg     420
ttcttgcgta aaagtttgtg tgaagaaaca ggggtagttg cgcagattag ttgtaatatg     480
cgcataggat gggtcattga cttctttcct cgaaagagcc acaccgttag ctaaaaaagg     540
acgcgcatct accccaaaat agaatgtggg gaaataggac gcgcaacttc ctctcaatca     600
ctggacgtca gaaaaacaaa tgcgcaatcg agtcaccctc cgtgatatccc tccgtgatac     660 cccctctccg tctattctga cagcgtctcc ccatgacgtt tcaatctact tagaaaagat     720 ttcgttttt tttccttcaa ttacacgatc tcatcttctg caagggtctg gaggacatca     780
ccaatctgcg actccataac ttagtcctga gtttatattt acgcttcatc tgatgagtag     840
gaagaaaaag tttcacgaaa ttcccccgcc aacttgccct tcggaataag cagccactct     900
ccttctgccc atagtaagct tgcgcgaggc cccaacttgg ccagaaactt taaatatgcc     960
aaacaatctc ccccaatcta agttctccct cttctaaaaa                          1000
```

<210> SEQ ID NO 7
<211> LENGTH: 1662
<212> TYPE: DNA
<213> ORGANISM: Pichia pastoris

<400> SEQUENCE: 7

```
atgtcctcgt tttttctaaa caaccaaaca gtaaagatga tgacgccttt gggaagagct       60
agagctctaa attttcaggg caagtttat gataaatttc caaaaactta caatatctac      120
gctattgcaa taacagccac cgtttctgga ctgatgttcg gttttgatat ttcttctgtg     180
tcctcgttcg taagtcagga tcattacaga aactacttca accgtcccga cagtttgacg     240 caaggggta tcaccgcaag tatggctgga ggttcttct gggttcgtt attttcttct     300 gacttccagg atatctttgg aagaagagtt gctctgcata tgtgcagtgt cctctggatt     360
atcggggcca ttcttcaatg cgctgcacaa aaccaaggta tgctgatcgc agggagattg     420
atttccggta tcggtgtcgg gtttggttca gcttcagctc cagtctattg ttctgaagtt     480
gctccagcaa agattagagg aatgattgga ggattatttc aattttctgt cactgtgggt     540
atcatgataa tgttttatat cggatatgga tgtcactaca ttgacggcgt tgcatcattt     600
agactggcct ggggtttgca aatggttcca ggtcttattc ttttggtcgg tgtattcttc     660
```

```
cttcctgagt ctccaagatg gctggctaac cacaaccgct gggaagacgc agttgaggtt        720
attgctaatg ttgttgcaaa aggtgacaga gaaaacgccg atgtgcgtct gcaattggat        780
gaagttcagg agcaactatt gattgacaaa gatgcttctg attttggtta ccttgatttg        840
tttaagaaag attgtatcaa acgtaccttc attggagtgt cagctcaagt gtggcaacaa        900
ctttgtggta ttaatgttgc aatgtactac gttgtgtatc tcttccaaat ggctggtttt        960
actggaaatg tggcgttggt atcgtcctca attcaatatg ttttgaatgt tgttatgact       1020
gttccagctt tgtttctaat ggaccgtata ggcagacgac ccctactaat tggtggtggt       1080
attttcatgt gtatttggct gtttggagtg caggattat taggcactta ctctgaacca        1140
attgaaaatt tcagcggtga tgatactgtc agaattacta ttcctgacca gcacaaggct       1200
gcagcaaggg gtgttattgc ctgttcctat ctattcgtgt gctcctttgc tccaacctgg       1260
ggtatctgca tttgggttta tgcctctgaa attttcaaca acagacaaag agcaaaggga       1320
gcagcatttg ctgcctccgc taactggatt tcaactttg ccttggctat gttcgtgcca        1380
tcagccttta gaaacattac atggaagact tacatcattt ttggagtatt ttcgttctgc       1440
ttaacaatcc atgttttctt acaattccca gaaaccagag gtaagacttt ggaagaaatt       1500
gatcaaatgt ttaaggacaa tattccagct tggagaagtg cttcgtacgt tccagatatg       1560
ccaattttca caaagagaa ggtagtatct actgagcatg cagaaaatgc ttccagctcg        1620
tccgaaaaag ccttgatggt tcaggaagag gaatctgtat aa                          1662

<210> SEQ ID NO 8
<211> LENGTH: 987
<212> TYPE: DNA
<213> ORGANISM: Pichia pastoris

<400> SEQUENCE: 8
atggtagttg caatcgaagg tggtacaggc ttaggcctta tgaatcttac ttggaaacca         60
actccaaccc caattgatga tgcaattgag acaattagat atgctgttga ggaagctggt        120
gtcagatact tgaacggagg agagttctac aactttcctc ttgattcaaa cctgaatttg        180
cagtacattc aggaatttgc aaaaaggtac cccgagctat ataaaaaggt gagtctgtcg        240
gtaaaaggtg ctgtcagttt ggtcgatgtg agccccgatt cttccccgga gaaccttgaa        300
aaatcgattt caaacataac caaacatttg ccgaacaact tcctgccaat tttttgagcct       360 gctagaatcg ataaacgtta ctccattgag gagacaataa agaatctctc taagttcgtc        420
gaagatggca gaattggagg tatttcactt agtgaagttg gtgctgacac tatcagaaga        480
gctgcgaaag tggctcccat cgcctgtgtg gaagtggagt tttctctatt gactagagat        540
attcttcata tggagttcct tgctgcttgt gaggatttga acattcctat tattgcctac        600
agtcccttgg gaagaggatt tttgactgga acgataaaca gcaaagctga cattcctgaa        660
ggtgatatca ggttaagttt ggaaagattc aatgacgatg aagttattga acacaatttg        720
aaacttgttc acggttttga aaagatagcc gacaaaaaag gagtcacatt ggctcaattg        780
tctcttgcgt ggttacgaaa gtttggagat aaacacgtca aggtgcttcc tattccaagc        840
tgctcatctc ctcgtagagt tgcagaaaac acaaaagaga tttccttgac tgatagcgag        900
ttccaggaga ttactgactt tgcagagtcg gttccaatca aggtggtcg ttacaacaaa         960 gcaagtgagg ctgttcttaa cggttag                                            987
```

<210> SEQ ID NO 9
<211> LENGTH: 1506
<212> TYPE: DNA
<213> ORGANISM: Pichia pastoris

<400> SEQUENCE: 9

| | | | | | |
|---|---|---|---|---|---|
| atgacatttg | ctcctccctt | agaattcgag | attgaccttc | ctaacggatt | gaagtacact | 60 |
| caaccattgg | gactcttcat | caacaatgag | tttgttgaag | gtgtagaggg | aaagctctta | 120 |
| ccagtgatca | atccttgtga | tgagactaaa | ataacccaag | tttgggaagc | ttctgcagcg | 180 |
| gatgttgacc | gtgctgttga | tgccgctgaa | gatgctttca | acaactccgt | atgggctact | 240 |
| caggacccat | tagagagggg | aaagctgatg | aacaaattgg | cagaccttat | cgatcgtgac | 300 |
| ttcaacatct | tggctggtat | cgaatccatc | gacaatggta | aggcctatac | ctctgcccag | 360 |
| ggtgatgtta | ctcttgctgt | caactacatc | agatcctgtg | ctggatgggc | cgacaagatt | 420 |
| ttgggaaacg | ttgttgattc | cggaaacacc | caccttaact | tggttaaaag | agagccattg | 480 |
| ggtgttgtgg | gacaaattat | cccatggaac | tttcctctcc | tgatgttggc | ttggaagttg | 540 |
| ggacctgcgc | tggccacagg | taacactgtt | gttttgaaga | ctgccgagtc | taccctctg | 600 |
| tcgggtttat | acgttgccaa | attgatcaag | gaggccggtt | tcccacctgg | tgtggttaac | 660 |
| attctcagtg | gtttcggtaa | cccagctgga | gctgccatcg | ctgctcatcc | cagaatcaag | 720 |
| aagattgctt | tcaccggatc | cactgcaaca | ggccgtaaga | tcatgaagc | agccgctaaa | 780 |
| tctaacctga | aaaaagtcac | tttggaacta | ggtggtaaat | ctccaaacat | tgtgtttgaa | 840 |
| gatgctgata | tccagaagac | tatccataac | attattttgg | gaatcttctt | caattctggt | 900 |
| gaagtctgtt | gtgcaggttc | cagagtctac | attcaagaca | ctgtgtatga | agaagtgctt | 960 |
| gaagccttca | gaaggagac | tgataacgtt | aaggttggtg | accattcga | agaaggtgtc | 1020 |
| ttccaagggc | ctcagacctc | tgagttgcaa | cttaacagaa | tccttagtta | catcaaacac | 1080 |
| ggtaaggatg | aaggtgctcg | tgtaattacc | ggtggttcaa | gataccgtaa | ccgaggttac | 1140 |
| tacattaagc | ccacaatttt | tgctgacgtt | actgaagaca | tgaagattgt | caaggaggag | 1200 |
| atttttggtc | ctgtggttac | tatcactaag | ttctctaccg | tggatgaggt | tgttggatat | 1260 |
| gccaacaaca | ccaactatgg | tctagctgct | ggtattcaca | aaacaacttt | gaacaaagcc | 1320 |
| attgatgttg | ccagtagaat | caaggcgggt | gtcgtttgga | ttaacaccta | caacgatttc | 1380 |
| caccacatgg | ttcctttcgg | aggttatgga | gaatctggta | ttggcagaga | gcttggtgct | 1440 |
| gaggctttgg | ataactacac | tcaagccaag | gctatcagaa | ttgcttacac | tcctgaacat | 1500 |
| aagtag | | | | | | 1506 |

<210> SEQ ID NO 10
<211> LENGTH: 1578
<212> TYPE: DNA
<213> ORGANISM: Pichia pastoris

<400> SEQUENCE: 10

| | | | | | |
|---|---|---|---|---|---|
| atgcttagaa | cttctccagc | tactaagaaa | gctctcaagt | cgcagattaa | cgccttcaac | 60 |
| gttgctgcct | tgagattcta | ctcctcattg | cctttgcagg | ttccaattac | cttgccaaac | 120 |
| ggtaagacct | acaatcagcc | aacaggtttg | tttatcaaca | atgagttcgt | tccttctaag | 180 |
| caaggtaaga | cctttgctgt | tttaaaccct | tccactgagg | aggagattac | tcacgtctac | 240 |
| gagtccagag | aggacgacgt | tgagttagcc | gttgcagccg | ctcaaaaggc | tttcgactca | 300 |
| acctggtcca | cccaggaccc | tgctgagaga | ggtaaggtct | tgaacaagtt | ggctgacctg | 360 |

```
atcgaggagc actctgagac ccttgccgcc atcgagtcct tggacaacgg taaggccatt    420
tcctccgcta gaggtgatgt tggtctggtt gtcgcctact tgaagtcctg tgccggttgg    480
gccgacaagg ttttcggtag agttgttgaa accggaagct cccacttcaa ctacgttaga    540
agagagccat tgggtgtttg tggtcagatt atcccatgga actttcctct tctgatgtgg    600
tcctggaaag ttggtccagc tttggccact ggtaacactg ttgtcctgaa gacagccgag    660
tctactcctc tgtccgccct gtacgtttcc aattggtca aggaggccgg tatcccagct     720
ggtgtccaca acattgtgtc cggtttcggt aagattactg gtgaagctat tgctactcat    780
cctaagatca agaaggttgc cttcactggt tctaccgcca ctggtcgtca catcatgaag    840
gctgctgccg aatccaactt gaagaaggtt actttggagt tgggtggtaa atctcctaac    900
atcgtgttca acgatgctaa cattaagcaa gctgtcgcca acatcatcct cggtatttac    960
tacaactctg agaagtttg ttgtgctggt tccagagttt atgttcaatc cggtatttac     1020
gacgagcttt tggccgaatt caagactgct gctgagaatg tcaaggttgg taacccattc    1080
gacgaggaca ccttccaagg tgctcaaacc tctcagcaac aattggagaa gattttgggt    1140
ttcgttgagc gtggtaagaa ggacggtgct actttgatta ctggtggtgg cagattaggt    1200
gacaagggtt acttcgtcca gccaactatc ttcggtgatg ttacaccaga gatggagatt    1260
gtcaaggaag agatctttgg tcctgttgtc actatcagca agtttgacac cattgatgag    1320
gttgtcgacc ttgctaacga ctctcaatac ggtcttgctg ctggtatcca ctctgacgat    1380
atcaacaagg tcattgacgt tgctgctaga atcaagtccg gtaccgtgtg ggtcaacacc    1440
tacaacgatt tccaccaaat ggttccattc ggtggatttg gccaatccgg tattggtcgt    1500
gagatgggtg ttgaagcttt ggaaaactac acccaataca aggctatccg tgtcaagatc    1560
aaccacaaga acgagtaa                                                  1578
```

<210> SEQ ID NO 11
<211> LENGTH: 1614
<212> TYPE: DNA
<213> ORGANISM: Pichia pastoris

<400> SEQUENCE: 11

```
atgagttcaa cagatatcca aggtgatcaa ggtgacaatg aaaagatata cgccattgag    60
agcagtccct ccaatgagca aataaaagat attcatgagg ctccggccga caacaaaagt    120
gaactagaca tcccagtcaa acccaagggt tcctatatct tggtgtctgt gttatgtctt    180
ctagtcgcat tcggtggttt cgtgttcggt tgggataccg gtaccatctc aggtttcgtt    240
aacatgtctg actttacgag acgtttcgga cagtttaacg gtgaaacgta ttacctttct    300
aaagtgagag ttggtttaat tgtttctatt ttcaacattg gttgtgctat cggaggtgtc    360
actctaggta aacttggtga catttggggt agaaagaagg ctttgatgtt cgtcatggtc    420
atctatatgg tcggtatttt gattcaaatt gcttccattg acaaatggta ccagtatttc    480
attggaagaa ttattgcagg tctggccgtc ggtgcagttt ccgttttatc ccccatgttc    540
atcagtgaga cttctcctaa acacatcaga ggttccttag tctcctgcta ccaattaatg    600
attacagccg gtatttcctt gggttactgt accacttacg gaaccaagac ttacaccgac    660
tccacccaat ggagagttcc tttgggattg tgtttcgctt gggccattct gatgattgtt    720
ggtatgacct tcatgccaga gtccccacgt ttcttggttg aggttaacag agtcgacgag    780
gctatgaagt ccattgccag agttaacaag gtctctatcg acgatccatc tgtctacaat    840
gagatgagac ttatttctga cggtattgag aaggagaagg aggctggtag cgtttcttgg    900
```

```
ggtgaactgt tcactggtaa gccaaagatt ttctaccgtc tattgattgg tattttcatg      960
caatctttgc aacaattgac cggtaacaac tatttcttct actacggaac taccattttc     1020
aaggctgtcg gattggacga ttctttccaa acttctatca ttcttggtgt tgtcaatttt     1080
gcttccacat tcctaggtat ctacaccatg gataaatttg gtagaagaag aacacttttta    1140 ggaggttctg gagccatggt tgtttgtttg gtcattttca gttccgttgg tgtcaagtct     1200
ctttatgaga acggtaagga tgatccatcc aaaccagcag gtaacgccat gattgtcttc     1260
acctgtctgt tcattttctt ctttgcatgt acctgggctc caggtgtttt cgtcgttgtg     1320
tctgaaacct acccacttag aattagatcc aagggtatgg ccatcgctca aggttccaat     1380
tggctttggg gtttcctcat tgccttcttc actccattta tctcaggtgc cattgatttc     1440
gcctacggtt acgtctttat gggatgtact ctgttcgcct tcttctttgt gtacttcttc     1500
gttcctgaaa ccaagggtct gtcgctggaa gacgttgatg aagtctatga gaaccttacc     1560
ttcggaagag catatgcata cagccacacg attaaagaca agggcgccct ataa           1614
```

<210> SEQ ID NO 12
<211> LENGTH: 1032
<212> TYPE: DNA
<213> ORGANISM: Pichia pastoris

<400> SEQUENCE: 12

```
atggccctat ctcctaccta tcagggctac atatctacca ctggcgacgc gttgatcgtg       60
atccaggcag ctctaaataa ccatttgaat cttcttcccc gaagaccaag agaaagagag      120
cgagatgggc taatacgatc aggtaacgta tttgttttttg tcgagcaacg gtctcatatc     180
aaacgatgga ccgatggtat cccctggtct ccatctagag tccttggaaa gttcttgttg     240
tatcgggaac tggacaagga tacccccaaa aactcgcaaa gtgacgaaga tactgaggag     300
gggagaaaga ggcgaaagac ttctgtggat gtaaccgatc caaataccag gcagttggtg     360
ggatcattgg tgacttccta tgacttcaaa gaggatggac ttattaaaaa aacactctcc     420
ttgactttcc agaccggtgc taatgaagaa agggaaacag tgcacttgat tagttattat     480
actccggaag atgtaacgaa ccatcgtttg aacaggccgt ctgacaatcc atatctggcc     540
aatatcactg tttcagagtc attattgact gccttgagag agagtaccct tggaggaaga     600
gcaacgtctg atgacgagct ttctttagtc agaagtaact cgttagagta ccaagaggta     660
ccaatgaaca tatctatgtc tttacccttta tcaactccac tttccttgaa cacaggagta     720
aactcaacta cccagctgca acagcaacaa ctacaacaac aacaacagca acagcaacag     780
cagcagcaac aacagcagca acaacagcaa ccggtagcat cccttccaaa atttgatgga     840
tcctttctat tacaacaggg tgtaattcca gttcctcatt tcatggacca aaaaatggga     900
agtagcaatt cgtggattaa caattggttt cgtccaaatt cgtcagaatc aaatgggcta     960
tcggttatcg acctcacaa gggatatgac gaacaaagtc cagcaacgag ttatactttg    1020
aatgaacgtt ga                                                       1032
```

<210> SEQ ID NO 13
<211> LENGTH: 491
<212> TYPE: DNA
<213> ORGANISM: Pichia pastoris

<400> SEQUENCE: 13

```
cttttttgta gaaatgtctt ggtgtcctcg tccaatcagg tagccatctc tgaaatatct       60
ggctccgttg caactccgaa cgacctgctg gcaacgtaaa attctccggg gtaaaactta    120
```

```
aatgtggagt aatggaacca gaaacgtctc ttcccttctc tctccttcca ccgcccgtta    180
ccgtccctag gaaattttac tctgctggag agcttcttct acggccccct tgcagcaatg    240
ctcttcccag cattacgttg cgggtaaaac ggaggtcgtg tacccgacct agcagcccag    300
ggatggaaaa gtcccggccg tcgctggcaa taatagcggg cggacgcatg tcatgagatt    360
attggaaacc accagaatcg aatataaaag gcgaacacct ttcccaattt tggtttctcc    420
tgacccaaag actttaaatt taatttattt gtccctattt caatcaattg aacaactatc    480
acctgcaggc c                                                         491
```

<210> SEQ ID NO 14
<211> LENGTH: 34
<212> TYPE: DNA
<213> ORGANISM: artificial
<220> FEATURE:
<223> OTHER INFORMATION: Primer

<400> SEQUENCE: 14

```
gatagggccc caaacatttg ctcccctag tctc                                 34
```

<210> SEQ ID NO 15
<211> LENGTH: 39
<212> TYPE: DNA
<213> ORGANISM: artificial
<220> FEATURE:
<223> OTHER INFORMATION: Primer

<400> SEQUENCE: 15

```
gatacctgca ggaagggtgg aattttaagg atcttttat                           39
```

<210> SEQ ID NO 16
<211> LENGTH: 36
<212> TYPE: DNA
<213> ORGANISM: artificial
<220> FEATURE:
<223> OTHER INFORMATION: Primer

<400> SEQUENCE: 16

```
gatagggccc cagcaatcca gtaaccttt ctgaat                               36
```

<210> SEQ ID NO 17
<211> LENGTH: 36
<212> TYPE: DNA
<213> ORGANISM: artificial
<220> FEATURE:
<223> OTHER INFORMATION: Primer

<400> SEQUENCE: 17

```
gatacctgca ggttgagttc aataaattgt ccggga                              36
```

<210> SEQ ID NO 18
<211> LENGTH: 35
<212> TYPE: DNA
<213> ORGANISM: artificial
<220> FEATURE:
<223> OTHER INFORMATION: Primer

<400> SEQUENCE: 18

```
gatagggccc tggactgttc aatttgaagt cgatg                               35
```

<210> SEQ ID NO 19
<211> LENGTH: 37
<212> TYPE: DNA
<213> ORGANISM: artificial

```
<220> FEATURE:
<223> OTHER INFORMATION: Primer

<400> SEQUENCE: 19
gatacctgca ggggataaag gtaagggaaa aaagcaa                                37

<210> SEQ ID NO 20
<211> LENGTH: 36
<212> TYPE: DNA
<213> ORGANISM: artificial
<220> FEATURE:
<223> OTHER INFORMATION: Primer

<400> SEQUENCE: 20
gatagggccc agaccagcag tttaactacg caaatc                                 36

<210> SEQ ID NO 21
<211> LENGTH: 36
<212> TYPE: DNA
<213> ORGANISM: artificial
<220> FEATURE:
<223> OTHER INFORMATION: Primer

<400> SEQUENCE: 21
gatacctgca ggcttttctt tgggcaagga aaaatc                                 36

<210> SEQ ID NO 22
<211> LENGTH: 39
<212> TYPE: DNA
<213> ORGANISM: artificial
<220> FEATURE:
<223> OTHER INFORMATION: Primer

<400> SEQUENCE: 22
gatagggccc aattgattaa gttcagtgaa atttcaaac                              39

<210> SEQ ID NO 23
<211> LENGTH: 42
<212> TYPE: DNA
<213> ORGANISM: artificial
<220> FEATURE:
<223> OTHER INFORMATION: Primer

<400> SEQUENCE: 23
gatacctgca ggattatatt atggggaata atgaagagaa gg                          42

<210> SEQ ID NO 24
<211> LENGTH: 33
<212> TYPE: DNA
<213> ORGANISM: artificial
<220> FEATURE:
<223> OTHER INFORMATION: Primer

<400> SEQUENCE: 24
gatagggccc ctgcacaacc attgccagta agg                                    33

<210> SEQ ID NO 25
<211> LENGTH: 40
<212> TYPE: DNA
<213> ORGANISM: artificial
<220> FEATURE:
<223> OTHER INFORMATION: Primer

<400> SEQUENCE: 25
gatacctgca ggtttttaga agagggagaa cttagattgg                             40
```

```
<210> SEQ ID NO 26
<211> LENGTH: 24
<212> TYPE: DNA
<213> ORGANISM: artificial
<220> FEATURE:
<223> OTHER INFORMATION: Primer

<400> SEQUENCE: 26
cctgaggctt tgttccaccc atct                                          24

<210> SEQ ID NO 27
<211> LENGTH: 30
<212> TYPE: DNA
<213> ORGANISM: artificial
<220> FEATURE:
<223> OTHER INFORMATION: Primer

<400> SEQUENCE: 27
ggaacatagt agtaccaccg gacataacga                                    30

<210> SEQ ID NO 28
<211> LENGTH: 22
<212> TYPE: DNA
<213> ORGANISM: artificial
<220> FEATURE:
<223> OTHER INFORMATION: Primer

<400> SEQUENCE: 28
tcgccgacca ctaccagcag aa                                            22

<210> SEQ ID NO 29
<211> LENGTH: 23
<212> TYPE: DNA
<213> ORGANISM: artificial
<220> FEATURE:
<223> OTHER INFORMATION: Primer

<400> SEQUENCE: 29
accatgtgat cgcgcttctc gtt                                           23

<210> SEQ ID NO 30
<211> LENGTH: 24
<212> TYPE: DNA
<213> ORGANISM: artificial
<220> FEATURE:
<223> OTHER INFORMATION: Primer

<400> SEQUENCE: 30
cctgaggctt tgttccaccc atct                                          24

<210> SEQ ID NO 31
<211> LENGTH: 30
<212> TYPE: DNA
<213> ORGANISM: artificial
<220> FEATURE:
<223> OTHER INFORMATION: Primer

<400> SEQUENCE: 31
ggaacatagt agtaccaccg gacataacga                                    30

<210> SEQ ID NO 32
<211> LENGTH: 28
<212> TYPE: DNA
<213> ORGANISM: artificial
<220> FEATURE:
<223> OTHER INFORMATION: Primer
```

```
<400> SEQUENCE: 32
aaacctagga aaagtgggca gcaaatgt                                        28

<210> SEQ ID NO 33
<211> LENGTH: 29
<212> TYPE: DNA
<213> ORGANISM: artificial
<220> FEATURE:
<223> OTHER INFORMATION: Primer

<400> SEQUENCE: 33
actctgtcac ttactggcgt tttctcatg                                       29

<210> SEQ ID NO 34
<211> LENGTH: 34
<212> TYPE: DNA
<213> ORGANISM: artificial
<220> FEATURE:
<223> OTHER INFORMATION: Primer

<400> SEQUENCE: 34
gatagggccc caaacatttg ctcccsctag tctc                                 34

<210> SEQ ID NO 35
<211> LENGTH: 39
<212> TYPE: DNA
<213> ORGANISM: artificial
<220> FEATURE:
<223> OTHER INFORMATION: Primer

<400> SEQUENCE: 35
gatagggccc ggaatctgta ttgttagaaa gaacgagag                            39

<210> SEQ ID NO 36
<211> LENGTH: 36
<212> TYPE: DNA
<213> ORGANISM: artificial
<220> FEATURE:
<223> OTHER INFORMATION: Primer

<400> SEQUENCE: 36
gatagggccc ccatattcag taggtgtttc ttgcac                               36

<210> SEQ ID NO 37
<211> LENGTH: 36
<212> TYPE: DNA
<213> ORGANISM: artificial
<220> FEATURE:
<223> OTHER INFORMATION: Primer

<400> SEQUENCE: 37
gatagggccc ctgcagatag acttcaagat ctcagg                               36

<210> SEQ ID NO 38
<211> LENGTH: 32
<212> TYPE: DNA
<213> ORGANISM: artificial
<220> FEATURE:
<223> OTHER INFORMATION: Primer

<400> SEQUENCE: 38
gatagggccc gaccccgttt tcgtgacaaa tt                                   32
```

<210> SEQ ID NO 39
<211> LENGTH: 37
<212> TYPE: DNA
<213> ORGANISM: artificial
<220> FEATURE:
<223> OTHER INFORMATION: Primer

<400> SEQUENCE: 39
gatagggccc ccggataaga gaattttgtt tgattat        37

<210> SEQ ID NO 40
<211> LENGTH: 31
<212> TYPE: DNA
<213> ORGANISM: artificial
<220> FEATURE:
<223> OTHER INFORMATION: Primer

<400> SEQUENCE: 40
gatagggccc gcctgctcca tattttccg g        31

<210> SEQ ID NO 41
<211> LENGTH: 859
<212> TYPE: DNA
<213> ORGANISM: artificial
<220> FEATURE:
<223> OTHER INFORMATION: promoter variant

<400> SEQUENCE: 41
ggaatctgta ttgttagaaa gaacgagagt ttttacggc gccgccatat tgggccgtgt        60
gaaaacagct tgaaacccca ctactttcaa aggttctgtt gctatacacg aaccatgttt        120
aaccaacctc gcttttgact tgactgaagt catcggttaa caatcaagta ccctagtctg        180
tctgaatgct cctttccata ttcagtaggt gtttcttgca cttttgcatg cactgcggaa        240
gaattagcca atagcgcgtt tcatatgcgc ttttaccccc tcttttgtca gcgcaaaat        300 gcctgtaaga tttggtgggg gtgtgagccg ttagctgaag tacaacaggc taattccctg        360
aaaaaactgc agatagactt caagatctca gggattccca ctatttggta ttctgatatg        420
tttttcctga tatgcatcaa aactctaatc taaaacctga atctccgcta tttttttttt        480 tttttttgatg accccgtttt cgtgacaaat taatttccaa cggggtcttg tccggataag        540
agaattttgt tgattatcc gttcggataa atggacgcct gctccatatt tttccggtta        600 ttacccccacc tggaagtgcc cagaattttc cggggattac ggataatacg gtggtctgga        660
ttaattaata cgccaagtct tacatttttgt tgcagtctcg tgcgagtatg tgcaataata        720
aacaagatga gccaatttat tggattagtt gcagcttgac cccgccatag ctaggcatag        780
ccaagtgcta tgggtgttag atgatgcact tggatgcagt gagttttgga gtataaaaga        840
tccttaaaat tccacccctt        859

<210> SEQ ID NO 42
<211> LENGTH: 664
<212> TYPE: DNA
<213> ORGANISM: artificial
<220> FEATURE:
<223> OTHER INFORMATION: promoter variant

<400> SEQUENCE: 42
ccatattcag taggtgtttc ttgcacttttt gcatgcactg cggaagaatt agccaatagc        60
gcgtttcata tgcgctttta ccccctcttt tgtcaagcgc aaaatgcctg taagatttgg        120
tgggggtgtg agccgttagc tgaagtacaa caggctaatt ccctgaaaaa actgcagata        180

```
gacttcaaga tctcagggat tcccactatt tggtattctg atatgttttt cctgatatgc    240
atcaaaactc taatctaaaa cctgaatctc cgctattttt tttttttttt tgatgacccc    300
gttttcgtga caaattaatt ccaacggggt cttgtccgga taagagaatt tttgtttgat    360
tatccgttcg gataaatgga cgcctgctcc atatttttcc ggttattacc ccacctggaa    420
gtgcccagaa ttttccgggg attacggata tacggtggtc tggattaatt aatacgcca     480 agtcttacat tttgttgcag tctcgtgcga gtatgtgcaa taataaacaa gatgagccaa    540
tttattggat tagttgcagc ttgaccccgc catagctagg catagccaag tgctatgggt    600
gttagatgat gcacttggat gcagtgagtt ttggagtata aaagatccta aaaattccac    660
cctt                                                                664

<210> SEQ ID NO 43
<211> LENGTH: 493
<212> TYPE: DNA
<213> ORGANISM: artificial
<220> FEATURE:
<223> OTHER INFORMATION: promoter variant

<400> SEQUENCE: 43
ctgcagatag acttcaagat ctcagggatt cccactattt ggtattctga tatgttttc      60 ctgatatgca tcaaaactct aatctaaaac ctgaatctcc gctatttttt tttttttttt    120
gatgaccccg ttttcgtgac aaattaattt ccaacggggt cttgtccgga taagagaatt    180
ttgtttgatt atccgttcgg ataaatggac gcctgctcca tatttttccg gttattaccc    240
cacctggaag tgcccagaat tttccgggga ttacggataa tacggtggtc tggattaatt    300
aatacgccaa gtcttacatt ttgttgcagt ctcgtgcgag tatgtgcaat aataaacaag    360
atgagccaat ttattggatt agttgcagct tgaccccgcc atagctaggc atagccaagt    420
gctatgggtg ttagatgatg cacttggatg cagtgagttt tggagtataa aagatcctta    480
aaattccacc ctt                                                       493

<210> SEQ ID NO 44
<211> LENGTH: 370
<212> TYPE: DNA
<213> ORGANISM: artificial
<220> FEATURE:
<223> OTHER INFORMATION: promoter variant

<400> SEQUENCE: 44
gaccccgttt tcgtgacaaa ttaatttcca acggggtctt gtccggataa gagaattttg     60
tttgattatc cgttcggata aatggacgcc tgctccatat ttttccggtt attaccccac    120
ctggaagtgc ccagaatttt ccggggatta cggataatac ggtggtctgg attaattaat    180
acgccaagtc ttacattttg ttgcagtctc gtgcgagtat gtgcaataat aaacaagatg    240
agccaattta ttggattagt tgcagcttga ccccgccata gctaggcata gccaagtgct    300
atgggtgtta gatgatgcac ttggatgcag tgagttttgg agtataaaag atccttaaaa    360
ttccacccct                                                            370

<210> SEQ ID NO 45
<211> LENGTH: 328
<212> TYPE: DNA
<213> ORGANISM: artificial
<220> FEATURE:
<223> OTHER INFORMATION: promoter variant
```

```
<400> SEQUENCE: 45
ccggataaga gaattttgtt tgattatccg ttcggataaa tggacgcctg ctccatattt      60
ttccggttat taccccacct ggaagtgccc agaattttcc ggggattacg gataatacgg     120
tggtctggat taattaatac gccaagtctt acattttgtt gcagtctcgt gcgagtatgt     180
gcaataataa acaagatgag ccaatttatt ggattagttg cagcttgacc ccgccatagc     240
taggcatagc caagtgctat gggtgttaga tgatgcactt ggatgcagtg agttttggag     300
tataaaagat ccttaaaatt ccaccctt                                        328

<210> SEQ ID NO 46
<211> LENGTH: 283
<212> TYPE: DNA
<213> ORGANISM: artificial
<220> FEATURE:
<223> OTHER INFORMATION: promoter variant

<400> SEQUENCE: 46
gcctgctcca tattttccg gttattaccc cacctggaag tgcccagaat tttccgggga      60
ttacggataa tacggtggtc tggattaatt aatacgccaa gtcttacatt ttgttgcagt    120
ctcgtgcgag tatgtgcaat aataaacaag atgagccaat ttattggatt agttgcagct    180
tgaccccgcc atagctaggc atagccaagt gctatgggtg ttagatgatg cacttggatg    240
cagtgagttt tggagtataa aagatcctta aaattccacc ctt                      283
```

METHODS OF PRODUCING PROMOTER VARIANTS

The invention refers to regulatable promoters and a method of producing a protein of interest in a eukaryotic cell culture under the control of a regulatable promoter.

BACKGROUND

Successful production of recombinant proteins has been accomplished with eukaryotic hosts. The most prominent examples are yeasts like *Saccharomyces cerevisiae*, *Pichia pastoris* or *Hansenula polymorpha*, filamentous fungi like *Aspergillus awamori* or *Trichoderma reesei*, or mammalian cells like e.g. CHO cells. While the production of some proteins is readily achieved at high rates, many other proteins are only obtained at comparatively low levels.

The heterologous expression of a gene in a host organism usually requires a vector allowing stable transformation of the host organism. A vector would provide the gene with a functional promoter adjacent to the 5' end of the coding sequence. The transcription is thereby regulated and initiated by this promoter sequence. Most promoters used up to date have been derived from genes that code for proteins that are usually present at high concentrations in the cell.

EP0103409A2 discloses the use of yeast promoters associated with expression of specific enzymes in the glycolytic pathway, i.e. promoters involved in expression of pyruvate kinase, triosephosphate isomerase, phosphoglucose isomerase, phosphorglycerate mutase, hexokinase 1 and 2, glucokinase, phosphofructose kinase, aldolase and glycolytic regulation gene.

WO 97/44470 describes yeast promoters from *Yarrowia lipolytica* for the translation elongation factor 1 (TEF1) protein and for the ribosomal protein S7 that are suitable for heterologous expression of proteins in yeast, and EP1951877A1 describes the use of the *P. pastoris* TEF1 promoter for the production of heterologous proteins.

WO2005003310 provides methods for the expression of a coding sequence of interest in yeast using a promoter of the glyceraldehyde-3-phosphate dehydrogenase or phosphoglycerate mutase from oleaginous yeast *Yarrowia lipolytica*.

Promoter sequences derived from genes involved in the methanol metabolic pathway of *Pichia pastoris* are disclosed in U.S. Pat. Nos. 4,808,537 and 4,855,231 (alcohol oxidase AOX1, AOX2) and U.S. Pat. No. 6,730,499B1 (formaldehyde dehydrogenase FLD1). US20080153126A1 includes mutant promoter sequences based on the AOX1 promoter.

The AOX1 promoter is induced only in response to methanol and repressed by other carbon sources, such as glucose or ethanol. Methanol has the disadvantage that it is unsuitable for use in the production of certain products, since it is potentially hazardous for its toxicity and flammability. Therefore, alternatives to the AOX1 promoter are sought.

US2008299616A1 introduces the regulatory sequences of the malate synthase (MLS1) gene for heterologous gene expression in *P. pastoris*, which is repressed in media containing glucose and derepressed under glucose starvation conditions or when acetate is present. However, this system is not considered suitable for efficient production methods, since the MLS1 promoter is weak with low activity under de-repressed conditions.

Schöler and Schüller (Mol. Cell Biol. 1994 14(6):3613-22) describe the control region of the isocitrate lyase gene ICL1, which is derepressed after transfer of cells from fermentative to non-fermentative growth conditions.

WO2008063302A2 describes the use of novel inducible promoters derived from ADH1 (alcohol dehydrogenase), ENO1 (enolase) and GUT1 genes of *P. pastoris* for the expression of heterologous proteins, CN1966688A the *P. pastoris* omega 3-fatty acid dehydrogenase promoter sequence, and WO002007117062A1 the *P. pastoris* derived auto-inducible NPS promoter, which is induced by phosphor limitation.

WO2008128701A2 describes the use of novel promoters, of which the promoter derived from the TH13 (thiamine metabolism) gene of *P. pastoris* is repressed in medium containing thiamine, and derepressed upon thiamine depletion.

US2009325241 A1 describes a method of ethanol production in a yeast cell employing a xylose-inducible promoter (FAS2 promoter).

It is desirable to provide improved recombinant eukaryotic cell lines to produce fermentation products that can be isolated with high yields. Therefore, it is the object of the present invention to provide for alternative regulatory elements suitable for recombinant production methods, which are simple and efficient.

SUMMARY OF THE INVENTION

The object is solved by the subject matter as claimed.

According to the invention there is provided a method of producing a protein of interest (POI) by culturing a recombinant eukaryotic cell line comprising an expression construct comprising a regulatable promoter and a nucleic acid molecule encoding a POI under the transcriptional control of said promoter, comprising the steps a) cultivating the cell line with a basal carbon source repressing the promoter, b) cultivating the cell line with no or a limited amount of a supplemental carbon source de-repressing the promoter to induce production of the POI at a transcription rate of at least 15% as compared to the native pGAP promoter of the cell, and c) producing and recovering the POI.

Said cultivating steps specifically comprise cultivating the cell line in the presence of said carbon sources, thus, in a culture medium comprising said carbon sources, or in step b) also in the absence of a supplemental carbon source.

Said induction of POI production specifically refers to induction of transcription, specifically including further translation and optional expression of said POI.

Said transcription rate specifically refers to the amount of transcripts obtained upon fully inducing said promoter. Said promoter is considered as de-repressed and fully induced, if the culture conditions provide for about maximum induction, e.g. at glucose concentrations of less than 0.4 g/L, preferably less than 0.04 g/L, specifically less than 0.02 g/L. The fully induced promoter preferably shows a transcription rate of at least 15%, preferably at least 20%, more preferred at least 30%, 40%, 50%, 60%, 70%, 80%, 90% and at least 100% or even higher transcription rate of at least 150% or at least 200% as compared to the native pGAP promoter. The transcription rate may, for example, be determined by the amount of transcripts of a reporter gene, such as eGFP, such as described in the Example section below, which shows the relatively high transcription rate of pG1 promoter of at least 50% as compared to the native pGAP promoter, upon cultivating a clone in solution. Alternatively, the transcription rate may be determined by the transcription strength on a microarray, where microarray data show the difference of expression level between repressed and de-repressed state and a high signal intensity in the fully induced state as compared to the native pGAP promoter. Such microarray data specifically show a transcription rate of more than 200% for pG1, more than 30% for pG3 and pG4, more than 60% for pG6, more than 30% for pG7, more than 20% for pG8, each value as compared to the native pGAP. Prior art promoter MLS1 or ICL1 were found to be too weak and thus not suitable for the purpose of the invention.

Said native pGAP promoter specifically is active in said recombinant eukaryotic cell in a similar way as in a native eukaryotic cell of the same species or strain, including the unmodified (non-recombinant) or recombinant eukaryotic cell. Such native pGAP promoter is commonly understood to be an endogenous promoter, thus, homologous to the eukaryotic cell, and serves as a standard or reference promoter for comparison purposes.

For example, a native pGAP promoter of *P. pastoris* is the unmodified, endogenous promoter sequence in *P. pastoris*, as used to control the expression of GAPDH in *P. pastoris*, e.g. having the sequence shown in FIG. 13: native pGAP promoter sequence of *P. pastoris* (GS115) (SEQ ID 13). If *P. pastoris* is used as a host for producing a POI according to the invention, the transcription strength or rate of the promoter according to the invention is compared to such native pGAP promoter of *P. pastoris*.

As another example, a native pGAP promoter of *S. cerevisiae* is the unmodified, endogenous promoter sequence in *S. cerevisiae*, as used to control the expression of GAPDH in *S. cerevisiae*. If *S. cerevisiae* is used as a host for producing a POI according to the invention, the transcription strength or rate of the promoter according to the invention is compared to such native pGAP promoter of *S. cerevisiae*.

Therefore, the relative transcription strength or rate of a promoter according to the invention is usually compared to the native pGAP promoter of a cell of the same species or strain that is used as a host for producing a POI.

According to a specific embodiment the basal carbon source is different from the supplemental carbon source, e.g. quantitatively and/or qualitatively different. The quantitative difference may provide for the different conditions to repress or de-repress the promoter activity.

According to a further specific embodiment the basal and the supplemental carbon sources comprise the same type of molecules or carbohydrates, preferably in different concentrations. According to a further specific embodiment the carbon source is a mixture of two or more different carbon sources.

Any type of organic carbon suitable used for eukaryotic cell culture may be used. According to a specific embodiment the carbon source is a hexose such as glucose, fructose, galactose or mannose, a disaccharide, such as saccharose, an alcohol, such as glycerol or ethanol, or a mixture thereof.

According to a specifically preferred embodiment, the basal carbon source is selected from the group consisting of glucose, glycerol, ethanol, or mixtures thereof, and complex nutrient material. According to a preferred embodiment, the basal carbon source is glycerol.

According to a further specific embodiment, the supplemental carbon source is a hexose such as glucose, fructose, galactose and mannose, a disaccharide, such as saccharose, an alcohol, such as glycerol or ethanol, or a mixture thereof. According to a preferred embodiment, the supplemental carbon source is glucose.

Specifically, the method may employ glycerol as the basal carbon source and glucose as the supplemental carbon source.

The de-repressed conditions suitably may be achieved by specific means. Step b) optionally employs a feed medium that provides for no or the supplemental carbon source in a limited amount.

Specifically, the feed medium is chemically defined and methanol-free.

The feed medium may be added to the culture medium in the liquid form or else in an alternative form, such as a solid, e.g. as a tablet or other sustained release means, or a gas, e.g. carbon dioxide. Yet according to a preferred embodiment the limited amount of the supplemental carbon source added to the cell culture medium, may even be zero. Preferably, the concentration of the supplemental carbon source in the culture medium is 0-1 g/L, preferably less than 0.6 g/L, more preferred less than 0.3 g/L, more preferred less than 0.1 g/L, preferably 1-50 mg/L, more preferred 1-10 mg/L, specifically preferred 1 mg/L or even below, such as below the detection limit as measured with a suitable standard assay, e.g. determined as a residual concentration in the culture medium upon consumption by the growing cell culture.

In a preferred method, the limited amount of the supplemental source provides for a residual amount in the cell culture which is below the detection limit as determined in the fermentation broth at the end of a production phase or in the output of a fermentation process, preferably upon harvesting the fermentation product.

Preferably, the limited amount of the supplemental carbon source is growth limiting to keep the specific growth rate within the range of 0.02 $h^{-1}$ to 0.2 $h^{-1}$, preferably 0.02 $h^{-1}$ to 0.15 $h^{-1}$.

According to a specific aspect of the invention, the promoter is a *Pichia pastoris* promoter or a functionally active variant thereof.

Herein the promoter according to the invention shall always refer to the sequences described herein, and functionally active variants thereof. As explained in detail below, such variants include homologs and analogs derived from species other than *Pichia pastoris*.

The method according to the invention may employ a promoter which is a wild-type promoter of *P. pastoris* or a functionally active variant thereof, e.g. capable of controlling the transcription of a specific gene in a wild-type or recombinant eukaryotic cell, e.g. a wild-type promoter for selected genes, which gene is selected from the group consisting of G1 (SEQ ID 7), such as coding for a (high affinity) glucose transporter, G3 (SEQ ID 8), G4 (SEQ ID 9), such as coding for a mitochondrial aldehyde dehydrogenase, G6 (SEQ ID 10), G7 (SEQ ID 11), such as coding for a member of the major facilitator sugar transporter family, or G8 (SEQ ID 12), such as coding for a member of the Gti1_Pac2 superfamily, or a functionally active variant thereof.

According to the invention there is specifically provided a promoter or a functionally active variant thereof, which would be natively associated with one of such genes in a wild-type yeast cell.

According to a specific embodiment, the cell line is selected from the group consisting of mammalian, insect, yeast, filamentous fungi and plant cell lines, preferably a yeast.

Specifically the yeast is selected from the group consisting of *Pichia, Candida, Torulopsis, Arxula, Hensenula, Yarrowia, Kluyveromyces, Saccharomyces, Komagataella*, preferably a methylotrophic yeast.

A specifically preferred yeast is *Pichia pastoris, Komagataella pastoris, K. phaffii*, or *K. pseudopastoris*.

According to a further specific embodiment, the promoter is not natively associated with the nucleotide sequence encoding the POI.

Specifically, the POI is a eukaryotic protein, preferably a mammalian protein.

A POI produced according to the invention may be a multimeric protein, preferably a dimer or tetramer.

According to one aspect of the invention, the POI is a recombinant or heterologous protein, preferably selected from therapeutic proteins, including antibodies or fragments thereof, enzymes and peptides, protein antibiotics, toxin fusion proteins, carbohydrate—protein conjugates, structural proteins, regulatory proteins, vaccines and vaccine like proteins or particles, process enzymes, growth factors, hormones and cytokines, or a metabolite of a POI.

A specific POI is an antigen binding molecule such as an antibody, or a fragment thereof. Among specific POIs are antibodies such as monoclonal antibodies (mAbs), immunoglobulin (Ig) or immunoglobulin class G (IgG), heavy-chain antibodies (HcAb's), or fragments thereof such as fragment-antigen binding (Fab), Fd, single-chain variable fragment (scFv), or engineered variants thereof such as for example Fv dimers (diabodies), Fv trimers (triabodies), Fv tetramers, or minibodies and single-domain antibodies like VH or VHH or V-NAR.

According to a specific embodiment, a fermentation product is manufactured using the POI, a metabolite or a derivative thereof.

According to another aspect of the invention, there is provided a method for controlling the expression of a POI in a recombinant eukaryotic cell under the transcriptional control of a carbon source regulatable promoter having a transcription strength of at least 15% as compared to the native pGAP promoter of the cell, wherein the expression is induced under conditions limiting the carbon source. The carbon source regulatable promoter preferably has a transcription strength of at least 20% as compared to the reference pGAP promoter, and specifically a transcription strength as described above with respect to the transcription rate as compared to the native pGAP promoter. Therefore, the fully induced promoter preferably has a transcription strength of at least 15%, preferably at least 20%, more preferred at least 30%, 40%, 50%, 60%, 70%, 80%, 90% and at least 100% or an even higher transcription strength of at least 150% or at least 200% as compared to the native pGAP promoter of the cell, as determined in the eukaryotic cell selected for producing the POI.

In a preferred embodiment such promoter is used that has a transcriptional activity or transcription strength in the de-repressed state, which is at least 2 fold, more preferably at least 5 fold, even more preferred at least 10 fold, more preferred at least 20 fold, more preferably at least 30, 40, 50, or 100 fold in the de-repressed state compared to the repressed state.

According to another aspect of the invention, there is provided a method of producing a POI in a recombinant eukaryotic cell under the transcriptional control of a carbon source regulatable promoter, wherein said promoter has a transcription strength as described above, i.e. at least 15% as compared to the native pGAP promoter of the cell. The carbon source regulatable promoter preferably has a transcription strength of at least 20% as compared to the reference pGAP promoter, more preferred at least 30%, 40%, 50%, 60%, 70%, 80%, 90% and at least 100% or an even higher transcription strength of at least 150% or at least 200% as compared to the native pGAP promoter of the cell. In a preferred embodiment such promoter is used that has a transcriptional activity in the de-repressed state which is at least which is at least 2 fold, more preferably at least 5 fold, even more preferred at least 10 fold, more preferred at least 20 fold, more preferably at least 30, 40, 50, or 100 fold in the de-repressed state compared to the repressed state. Suitably a specific promoter according to the invention is used in such a method.

In a specifically preferred method according to the invention, the promoter is a the regulatable promoter comprising a nucleic acid sequence selected from the group consisting of a) pG1 (SEQ ID 1), pG3 (SEQ ID 2), pG4 (SEQ ID 4), pG6 (SEQ ID 3), pG7 (SEQ ID 5), or pG8 (SEQ ID 6);

b) a sequence having at least 60% homology to pG1 (SEQ ID 1), pG3 (SEQ ID 2), pG4 (SEQ ID 4), pG6 (SEQ ID 3), pG7 (SEQ ID 5), or pG8 (SEQ ID 6);

c) a sequence which hybridizes under stringent conditions to pG1 (SEQ ID 1), pG3 (SEQ ID 2), pG4 (SEQ ID 4), pG6 (SEQ ID 3), pG7 (SEQ ID 5), or pG8 (SEQ ID 6); and d) a fragment or variant derived from a), b) or c), wherein said promoter is a functionally active promoter, which is a carbon source regulatable promoter capable of expressing a POI in a recombinant eukaryotic cell at a transcription rate of at least 15% as compared to the native pGAP promoter of the cell.

Specifically the variant of pG1 (SEQ ID 1), pG3 (SEQ ID 2), pG4 (SEQ ID 4), pG6 (SEQ ID 3), pG7 (SEQ ID 5) or pG8 (SEQ ID 6) is a functionally active variant selected from the group consisting of homologs with at least about 60% nucleotide sequence identity, homologs obtainable by modifying the parent nucleotide sequence by insertion, deletion or substitution of one or more nucleotides within the sequence or at either or both of the distal ends of the sequence, preferably with a nucleotide sequence of at least 200 bp, preferably at least 250 bp, preferably at least 300 bp, more preferred at least 400 bp, at least 500 bp, at least 600 bp, at least 700 bp, at least 800 bp, at least 900 bp, or at least 1000 bp, and analogs derived from species other than *Pichia pastoris*.

Some of the preferred functionally active variants of the promoter according to the invention are fragments of any of the pG1, pG3, pG4, pG6, pG7 or pG8 promoter nucleotide sequences, preferably fragments including the 3' end of a promoter nucleotide sequence, e.g. a nucleotide sequence derived from one of the promoter nucleotide sequences which has of a specific length and a deletion of the 5' terminal region, e.g. a cut-off of the nucleotide sequence at the 5' end, so to obtain a specific length with a range from the 3' end to a varying 5' end, such as with a length of the nucleotide sequence of at least 200 bp, preferably at least 250 bp, preferably at least 300 bp, more preferred at least 400 bp, at least 500 bp, at least 600 bp, at least 700 bp, at least 800 bp, at least 900 bp, or at least 1000 bp.

Exemplary variants have proven to be functionally active comprising or consisting of such fragments, e.g. fragments with a specific length within the range of 200 to 1000 bp, preferably within the range of 250 to 1000 bp, more preferably within the range of 300 to 1000 bp, e.g. including the 3' terminal sequence. For example, a functionally active variant of pG1 is selected from the group consisting of pG1a (SEQ ID 41), pG1b (SEQ ID 42), pG1c (SEQ ID 43), pG1d (SEQ ID 44), pG1e (SEQ ID 45) and pG1f (SEQ ID 46), thus, a nucleotide sequence within the range of 300-1000 bp, including the 3' terminal sequence up to nucleotide 1001.

According to another aspect of the invention, there is provided an isolated nucleic acid comprising a nucleic acid sequence selected from the group consisting of a) pG1 (SEQ ID 1), pG3 (SEQ ID 2), pG6 (SEQ ID 3), pG7 (SEQ ID 5) or pG8 (SEQ ID 6), b) a sequence having at least 60% homology to pG1 (SEQ ID 1), pG3 (SEQ ID 2), pG6 (SEQ ID 3), pG7 (SEQ ID 5) or pG8 (SEQ ID 6), c) a sequence which hybridizes under stringent conditions to pG1 (SEQ ID 1), pG3 (SEQ ID 2), pG6 (SEQ ID 3), pG7 (SEQ ID 5) or pG8 (SEQ ID 6), and d) a fragment or variant derived from a), b) or c), wherein said nucleic acid comprises a functionally active promoter, which is a carbon source regulatable promoter capable of expressing a POI in a recombinant eukaryotic cell at a transcription rate of at least 15% as compared to the native pGAP promoter of the cell.

Specifically the variant of pG1 (SEQ ID 1), pG3 (SEQ ID 2), pG6 (SEQ ID 3), pG7 (SEQ ID 5) or pG8 (SEQ ID 6) is a functionally active variant selected from the group consisting of homologs with at least about 60% nucleotide sequence identity, homologs obtainable by modifying the parent nucleotide sequence by insertion, deletion or substitution of one or more nucleotides within the sequence or at either or both of the distal ends of the sequence, preferably with a nucleotide sequence of at least 200 bp, preferably at least 250 bp, preferably at least 300 bp, more preferred at least 400 bp, at least 500 bp, at least 600 bp, at least 700 bp, at least 800 bp, at least 900 bp, or at least 1000 bp, and analogs derived from species other than *Pichia pastoris*.

Some of the preferred functionally active variants of the promoter according to the invention are fragments of any of the pG1, pG3, pG6, pG7 or pG8 promoter nucleotide sequences, preferably fragments including the 3' end of a promoter nucleotide sequence, e.g. a nucleotide sequence derived from one of the promoter nucleotide sequences which has of a specific length and a deletion of the 5' terminal region, e.g. a cut-off of the nucleotide sequence at the 5' end, so to obtain a specific length with a range from the 3' end to a varying 5' end, such as with a length of the nucleotide sequence of at least 200 bp, preferably at least 250 bp, preferably at least 300 bp, more preferred at least 400 bp, at least 500 bp, at least 600 bp, at least 700 bp, at least 800 bp, at least 900 bp, or at least 1000 bp.

Exemplary variants have proven to be functionally active comprising or consisting of such fragments, e.g. fragments with a specific length within the range of 200 to 1000 bp, preferably within the range of 250 to 1000 bp, more preferably within the range of 300 to 1000 bp, e.g. including the 3' terminal sequence. For example, a functionally active variant of pG1 is selected from the group consisting of pG1a (SEQ ID 41), pG1b (SEQ ID 42), pG1c (SEQ ID 43), pG1d (SEQ ID 44), pG1e (SEQ ID 45) and pG1f (SEQ ID 46), thus, a nucleotide sequence within the range of 300-1000 bp, including the 3' terminal sequence up to nucleotide 1001.

The carbon source regulatable promoter preferably has a transcription strength as described above, preferably at least 20% as compared to the reference pGAP promoter, more preferred at least 30%, 40%, 50%, 60%, 70%, 80%, 90% and at least 100% or an even higher transcription strength of at least 150% or at least 200% as compared to the native pGAP promoter. In a preferred embodiment such promoter is used that has a transcriptional activity in the de-repressed state which is at least which is at least 2 fold, more preferably at least 5 fold, even more preferred at least 10 fold, more preferred at least 20 fold, more preferably at least 30, 40, 50, or 100 fold in the de-repressed state compared to the repressed state. Suitably a specific promoter according to the invention is used in such a method.

Yet, according to a further aspect of the invention, there is provided an expression construct comprising a promoter according to the invention, operably linked to a nucleotide sequence encoding a POI under the transcriptional control of said promoter, which promoter is not natively associated with the coding sequence of the POI.

A further aspect of the invention refers to a vector comprising the construct according to the invention.

A further aspect of the invention refers to a recombinant eukaryotic cell comprising the construct or the vector according to the invention.

Specifically the cell is selected from the group consisting of mammalian, insect, yeast, filamentous fungi and plant cell lines, preferably a yeast.

The yeast may suitably be selected from the group consisting of *Pichia, Candida, Torulopsis, Arxula, Hensenula, Yarrowia, Kluyveromyces, Saccharomyces, Komagataella*, preferably a methylotrophic yeast.

Preferably, the yeast is *Pichia pastoris, Komagataella pastoris, K. phaffii*, or *K. pseudopastoris*.

According to a specific embodiment a cell is employed, which has a higher specific growth rate in the presence of a surplus of carbon source relative to conditions of limited carbon source.

A further aspect of the invention refers to the use of the recombinant eukaryotic cell of the invention for the production of the POI.

According to a further aspect of the invention, there is provided a method to screen or identify a carbon source regulatable promoter from eukaryotic cells, comprising the steps of a) cultivating eukaryotic cells in the presence of a carbon source in a batch culture under cell growing conditions, b) further cultivating the cells in a fed batch culture in the presence of a limited amount of a supplemental carbon source, c) providing samples of the cell culture of step a) and b), and d) performing transcription analysis in said samples to identify a regulatable promoter that shows a higher transcriptional strength in cells of step b) than in cells of step a).

Said higher transcriptional strength may be determined by the transcription strength in the fully induced state, which is e.g. obtained under conditions of glucose-limited chemostat cultivations, which is at least which is at least 2 fold, more preferably at least 5 fold, even more preferred at least 10 fold, more preferred at least 20 fold, more preferably at least 30, 40, 50, or 100 fold in the de-repressed state compared to the repressed state.

Preferably the transcription analysis is quantitative or semi-quantitative, preferably employing DNA microarrays, RNA sequencing and transcriptome analysis.

FIGURES

FIG. 1: promoter sequence pG1 (SEQ ID 1) of *P. pastoris*.
FIG. 2: promoter sequence pG3 (SEQ ID 2) of *P. pastoris*.
FIG. 3: promoter sequence pG4 (SEQ ID 4) of *P. pastoris*.
FIG. 4: promoter sequence pG6 (SEQ ID 3) of *P. pastoris*.
FIG. 5: promoter sequence pG7 (SEQ ID 5) of *P. pastoris*.
FIG. 6: promoter sequence pG8 (SEQ ID 6) of *P. pastoris*.
FIG. 7: coding sequences of gene of GS115 genome 01 (SEQ ID 7) of *P. pastoris*.
FIG. 8: coding sequences of gene of GS115 genome G3 (SEQ ID 8) of *P. pastoris*.

FIG. 9: coding sequences of gene of GS115 genome G4 (SEQ ID 9) of *P. pastoris*.

FIG. 10: coding sequences of gene of GS115 genome G6 (SEQ ID 10) of *P. pastoris*.

FIG. 11: coding sequences of gene of GS115 genome G7 (SEQ ID 11) of *P. pastoris*.

FIG. 12: coding sequences of gene of GS115 genome G8 (SEQ ID 12) of *P. pastoris*.

FIG. 13: native pGAP promoter sequence of *P. pastoris* (GS115) (SEQ ID 13)

| # | Name | PAS* | PIPA* | GS115 description |
|---|---|---|---|---|
| pGAP | TDH3 | PAS_chr2-1_0437 | PIPA02510 | Glyceraldehyde-3-phosphate dehydrogenase |

*PAS: ORF name in *P. pastoris* GS115; PIPA: ORF name in *P. pastoris* type strain DSMZ70382

FIG. 14: De-repression properties of the pG1 (circle), pG3 (triangle), pG4 (diamond) and pG6 (square) promoter: the maximum transcription activity is reached for pG1 at around 0.04 g glucose/L or less, whereas all other pG promoters reach it already at around 4 g/L or less. In order to compare the relative induction behaviors of the different promoters, the data were normalized by dividing each value by the D20 value of the respective promoter construct. Therefore the data are relative fluorescence values, and the data points at D20 are 1.0.

FIG. 15: functionally active variants of the promoter sequence pG1; pG1a-f (SEQ ID 41-46) of *P. pastoris*.

DETAILED DESCRIPTION OF THE INVENTION

Specific terms as used throughout the specification have the following meaning.

The term "carbon source" as used herein shall mean a fermentable carbon substrate, typically a source carbohydrate, suitable as an energy source for microorganisms, such as those capable of being metabolized by host organisms or production cell lines, in particular sources selected from the group consisting of monosaccharides, oligosaccharides, polysaccharides, alcohols including glycerol, in the purified form or provided in raw materials, such as a complex nutrient material. The carbon source may be used according to the invention as a single carbon source or as a mixture of different carbon sources.

A "basal carbon source" such as used according to the invention typically is a carbon source suitable for cell growth, such as a nutrient for eukaryotic cells. The basal carbon source may be provided in a medium, such as a basal medium or complex medium, but also in a chemically defined medium containing a purified carbon source. The basal carbon source typically is provided in an amount to provide for cell growth, in particular during the growth phase in a cultivation process, for example to obtain cell densities of at least 5 g/L cell dry mass, preferably at least 10 g/L cell dry mass, or at least 15 g/L cell dry mass, e.g. exhibiting viabilities of more than 90% during standard sub-culture steps, preferably more than 95%.

According to the invention the basal carbon source is typically used in an excess or surplus amount, which is understood as an excess providing energy to increase the biomass, e.g. during the growth phase of a cell line in a fed-batch cultivation process. This surplus amount is particularly in excess of the limited amount of a supplemental carbon source to achieve a residual concentration in the fermentation broth that is measurable and typically at least 10 fold higher, preferably at least 50 fold or at least 100 fold higher than during feeding the limited amount of the supplemental carbon source.

The term "chemically defined" with respect to cell culture medium, such as a feed medium in a fed-batch process, shall mean a growth medium suitable for the in vitro cell culture of a production cell line, in which all of the chemical components and peptides are known. Typically a chemically defined medium is entirely free of animal-derived components and represents a pure and consistent cell culture environment.

A "supplemental carbon source" such as used according to the invention typically is a supplemental substrate facilitating the production of fermentation products by production cell lines, in particular in the production phase of a cultivation process. The production phase specifically follows a growth phase, e.g. in batch, fed-batch and continuous cultivation process. The supplemental carbon source specifically may be contained in the feed of a fed-batch process.

A "limited amount" of a carbon source or a "limited carbon source" is herein understood as the amount of a carbon source necessary to keep a production cell line in a production phase or production mode. Such a limited amount may be employed in a fed-batch process, where the carbon source is contained in a feed medium and supplied to the culture at low feed rates for sustained energy delivery to produce a POI, while keeping the biomass at low growth rates. A feed medium is typically added to a fermentation broth during the production phase of a cell culture.

The limited amount of the supplemental carbon source may, for example, be determined by the residual amount of the supplemental carbon source in the cell culture broth, which is below a predetermined threshold or even below the detection limit as measured in a standard (carbohydrate) assay. The residual amount typically would be determined in the fermentation broth upon harvesting a fermentation product.

The limited amount of a supplemental carbon source may as well be determined by defining the average feed rate of the supplemental carbon source to the fermenter, e.g. as determined by the amount added over the full cultivation process, e.g. the fed batch phase, per cultivation time, to determine a calculated average amount per time. This average feed rate is kept low to ensure complete usage of the supplemental carbon source by the cell culture, e.g. between 0.6 g $L^{-1}$ $h^{-1}$ (g carbon source per L initial fermentation volume and h time) and 25 g $L^{-1}$ $h^{-1}$, preferably between between 1.6 g $L^{-1}$ V and 20 g $L^{-1}$ V.

The limited amount of a supplemental carbon source may also be determined by measuring the specific growth rate before and during the production process, which specific growth rate is kept low during the production phase, e.g. within a predetermined range, such as in the range of 0.02 $h^{-1}$ to 0.20 $h^{-1}$, preferably between 0.02 $h^{-1}$ and 0.15 $h^{-1}$.

The term "cell line" as used herein refers to an established clone of a particular cell type that has acquired the ability to proliferate over a prolonged period of time. The term "host cell line" refers to a cell line as used for expressing an endogenous or recombinant gene or products of a metabolic pathway to produce polypeptides or cell metabolites mediated by such polypeptides. A "production host cell line" or "production cell line" is commonly understood to be a cell line ready-to-use for cultivation in a bioreactor to obtain the product of a production process, such as a POI. The term "eukaryotic host" or "eukaryotic cell line" shall mean any eukaryotic cell or organism, which may be cultivated to produce a POI or a host cell metabolite. It is well understood that the term does not include human beings.

The term "expression" or "expression system" or "expression cassette" refers to nucleic acid molecules containing a desired coding sequence and control sequences in operable linkage, so that hosts transformed or transfected with these sequences are capable of producing the encoded proteins or host cell metabolites. In order to effect transformation, the expression system may be included in a vector; however, the relevant DNA may also be integrated into the host chromosome. Expression may refer to secreted or non-secreted expression products, including polypeptides or metabolites.

"Expression constructs" or "vectors" used herein are defined as DNA sequences that are required for the transcription of cloned recombinant nucleotide sequences, i.e. of recombinant genes and the translation of their mRNA in a suitable host organism. Expression vectors usually comprise an origin for autonomous replication in the host cells, selectable markers (e.g. an amino acid synthesis gene or a gene conferring resistance to antibiotics such as zeocin, kanamycin, G418 or hygromycin), a number of restriction enzyme cleavage sites, a suitable promoter sequence and a transcription terminator, which components are operably linked together. The terms "plasmid" and "vector" as used herein include autonomously replicating nucleotide sequences as well as genome integrating nucleotide sequences.

The term "variant" as used herein in the context of the present invention shall refer to any sequence with a specific homology or analogy. The variant promoter may e.g. be derived from the promoter sequence pG1 (SEQ ID 1), pG3 (SEQ ID 2), pG4 (SEQ ID 4), pG6 (SEQ ID 3), pG7 (SEQ ID 5) or pG8 (SEQ ID 6) by mutagenesis to produce sequences suitable for use as a promoter in recombinant cell lines. Such variant promoter may be obtained from a library of mutant sequences by selecting those library members with predetermined properties. Variant promoters may have the same or even improved properties, e.g. improved in inducing POI production, with increased differential effect under repressing and de-repressing conditions. The variant promoter may also be derived from analogous sequences, e.g. from eukaryotic species other than *Pichia pastoris* or from a genus other than *Pichia*, such as from *K. lactis, Z. rouxii, P. stipitis, H. polymorpha*. Specifically, the analogous promoter sequences natively associated with genes analogous to the corresponding *P. pastoris* genes may be used as such or as parent sequences to produce functionally active variants thereof. Specifically,

- a promoter analogous to pG1 is characterised that it is natively associated with a gene analogous to G1 (high affinity glucose transporter; *P. pastoris* GS115 description: Putative transporter, member of the sugar porter family; coding sequence SEQ ID 7);
- a promoter analogous to pG3 is characterised that it is natively associated with a gene analogous to G3 (coding sequence SEQ ID 8);
- a promoter analogous to pG4 is characterised that it is natively associated with a gene analogous to G4 (*P. pastoris* GS115: predicted mitochondrial aldehyde dehydrogenase; coding sequence SEQ ID 9);
- a promoter analogous to pG6 is characterised that it is natively associated with a gene analogous to G6 (coding sequence SEQ ID 10);
- a promoter analogous to pG7 is characterised that it is natively associated with a gene analogous to G7 (*P. pastoris* GS115: member of the major facilitator sugar transporter family; coding sequence SEQ ID 11);
- a promoter analogous to pG8 is characterised that it is natively associated with a gene analogous to G8 (*P. pastoris* GS115: member of the Gti1_Pac2 superfamily; coding sequence SEQ ID 12).

The properties of such analogous promoter sequences or functionally active variants thereof may be determined using standard techniques.

The "functionally active" variant of a nucleotide or promoter sequence as used herein means a sequence resulting from modification of a parent sequence by insertion, deletion or substitution of one or more nucleotides within the sequence or at either or both of the distal ends of the sequence, and which modification does not affect (in particular impair) the activity of this sequence.

Specifically, the functionally active variant of the promoter sequence according to the invention is selected from the group consisting of

- homologs with at least about 60% nucleotide sequence identity,
- homologs obtainable by modifying the parent nucleotide sequence by insertion, deletion or substitution of one or more nucleotides within the sequence or at either or both of the distal ends of the sequence, preferably with (i.e. comprising or consisting of) a nucleotide sequence of at least 200 bp, preferably at least 300 bp, more preferred at least 400 bp, at least 500 bp, at least 600 bp, at least 700 bp, at least 800 bp, at least 900 bp, or at least 1000 bp, and
- analogs derived from species other than *Pichia pastoris*.

Specifically preferred functionally active variants are those derived from a promoter according to the invention by modification and/or fragments of the promoter sequence, with (i.e. comprising or consisting of) a nucleotide sequence of at least 200 bp, preferably at least 250 bp, preferably at least 300 bp, more preferred at least 400 bp, at least 500 bp, at least 600 bp, at least 700 bp, at least 800 bp, at least 900 bp, or at least 1000 bp.

Some of the preferred functionally active variants of the promoter according to the invention are fragments of any of the pG1, pG3, pG4, pG6, pG7 or pG8 promoter nucleotide sequences, preferably fragments including the 3' end of a promoter nucleotide sequence, e.g. a nucleotide sequence derived from one of the promoter nucleotide sequences which has of a specific length and a deletion of the 5' terminal region, e.g. a cut-off of the nucleotide sequence at the 5' end, so to obtain a specific length with a range from the 3' end to a varying 5' end, such as with a length of the nucleotide sequence of at least 200 bp, preferably at least 250 bp, preferably at least 300 bp, more preferred at least 400 bp, at least 500 bp, at least 600 bp, at least 700 bp, at least 800 bp, at least 900 bp, or at least 1000 bp.

Exemplary variants have proven to be functionally active comprising or consisting of such fragments, e.g. fragments with a specific length within the range of 200 to 1000 bp, preferably within the range of 250 to 1000 bp, more preferably within the range of 300 to 1000 bp, e.g. including the 3' terminal sequence. For example, a functionally active variant of pG1 is selected from the group consisting of pG1a (SEQ ID 41), pG1b (SEQ ID 42), pG1c (SEQ ID 43), pG1d (SEQ ID 44), pG1e (SEQ ID 45) and pG1f (SEQ ID 46), thus, a nucleotide sequence within the range of 300-1000 bp, including the 3' terminal sequence up to nucleotide 1001.

The term "regulatable" with respect to a promoter as used herein shall refer to a promoter that is repressed in a eukaryotic cell in the presence of an excess amount of a carbon source (nutrient substrate) in the growth phase of a batch culture, and de-repressed to exert strong promoter activity in the production phase of a production cell line, e.g. upon reduction of the amount of carbon, such as upon feeding of a growth limiting carbon source (nutrient substrate) to a culture according to the fed-batch strategy. In this regard, the term "regulatable" is understood as "carbon source-limit regulatable" or "glucose-limit regulatable", referring to the de-repression of a promoter by carbon consumption, reduction, shortcoming or depletion, or by limited addition of the carbon source so that it is readily consumed by the cells.

The functionally active promoter according to the invention is a relatively strong regulatable promoter that is silenced or repressed under cell growth conditions (growth phase), and activated or de-repressed under production condition (production phase), and therefore suitable for inducing POI production in a production cell line by limiting the carbon source. Therefore, the functionally active variant of a promoter has at least such regulatable properties.

The strength of the regulatable promoter according to the invention refers to its transcription strength, represented by the efficiency of initiation of transcription occurring at that promoter with high or low frequency. The higher transcription strength the more frequently transcription will occur at that promoter. Promoter strength is important because it determines how often a given mRNA sequence is transcribed, effectively giving higher priority for transcription to some genes over others, leading to a higher concentration of the transcript. A gene that codes for a protein that is required in large quantities, for example, typically has a relatively strong promoter. The RNA polymerase can only perform one transcription task at a time and so must prioritize its work to be efficient. Differences in promoter strength are selected to allow for this prioritization. According to the invention the regulatable promoter is relatively strong in the fully induced state, which is typically understood as the state of about maximal activity. The relative strength is commonly determined with respect to a standard promoter, such as the respective pGAP promoter of the cell as used as the host cell. The frequency of transcription is commonly understood as the transcription rate, e.g. as determined by the amount of a transcript in a suitable assay, e.g. RT-PCR or Northern blotting. For example, the transcription strength of a promoter according to the invention is determined in the host cell which is *P. pastoris* and compared to the native pGAP promoter of *P. pastoris*.

The pGAP promoter initiates expression of the gap gene encoding glyceraldehyde-3-phosphate dehydrogenase (GAPDH), which is a constitutive promoter present in any microorganism capable of growing on glucose. GAPDH (EC 1\2\1\12), a key enzyme of glycolysis, plays a crucial role in catabolic and anabolic carbohydrate metabolism.

The regulatable promoter according to the invention exerts a relatively high transcription strength, reflected by a transcription rate or transcription strength of at least 15% as compared to the native pGAP promoter in the host cell, sometimes called "homologous pGAP promoter". Preferably the transcription rate or strength is at least 20%, in specifically preferred cases at least 30%, at least 40%, at least 50%, at least 60%, at least 70%, at least 80%, at least 90% and at least 100% or even higher, such as at least 150% or at least 200% as compared to the native pGAP promoter, e.g. determined in the eukaryotic cell selected as host cell for producing the POI.

Specifically preferred is a regulatable promoter, which has in the induced state at least a transcription strength of one of the pG1, pG3, PG4, pG6, pG7 or pG8 promoter. The comparative transcription strength employing the pGAP promoter as a reference may be determined by standard means, such as by measuring the quantity of transcripts, e.g. employing a microarray, or else in a cell culture, such as by measuring the quantity of respective gene expression products in recombinant cells. An exemplary test is illustrated in the Examples section.

Specifically the promoter according to the invention is carbon source regulatable with a differential promoter strength as determined in a test comparing its strength in the presence of glucose and glucose limitation, showing that it is still repressed at relatively high glucose concentrations, preferably at concentrations of at least 10 g/L, preferably at least 20 g/L. Specifically the promoter according to the invention is fully induced at limited glucose concentrations and glucose threshold concentrations fully inducing the promoter, which threshold is less than 20 g/L, preferably less than 10 g/L, less than 1 g/L, even less than 0.1 g/L or less than 50 mg/L, preferably with a full transcription strength of e.g. at least 50% of the native, homologous pGAP promoter, at glucose concentrations of less than 40 mg/L.

Preferably the differential promoter strength is determined by the initiation of POI production upon switching to inducing conditions below a predetermined carbon source threshold, and compared to the strength in the repressed state. The transcription strength commonly is understood as the strength in the fully induced state, i.e. showing about maximum activities under de-repressing conditions. The differential promoter strength is, e.g. determined according to the efficiency or yield of POI production in a recombinant host cell line under de-repressing conditions as compared to repressing conditions, or else by the amount of a transcript. The regulatable promoter according to the invention has a preferred differential promoter strength, which is at least 2 fold, more preferably at least 5 fold, even more preferred at least 10 fold, more preferred at least 20 fold, more preferably at least 30, 40, 50, or 100 fold in the de-repressed state compared to the repressed state, also understood as fold induction. Such differential promoter strength may be determined by a test as illustrated by the enclosed Examples.

Prior art promoter (MLS1 promoter or ICL1 promoter) turned out to have a differential promoter strength of significantly less than the 2 fold induction. Such prior art promoter was also not useful for industrial POI production, with a promoter strength of around 5% as compared to the pGAP promoter standard. This has been proven in a direct comparison with the promoter according to the invention.

The term "homology" indicates that two or more nucleotide sequences have the same or conserved base pairs at a corresponding position, to a certain degree, up to a degree close to 100%. A homologous sequence typically has at least about 50% nucleotide sequence identity, preferably at least about 60% identity, more preferably at least about 70% identity, more preferably at least about 80% identity, more preferably at least about 90% identity, more preferably at least about 95% identity.

The homologous promoter sequence according to the invention preferably has a certain homology to any of the pG1, pG3, pG4, pG6, pG7 or pG8 promoter nucleotide sequences of *P. pastoris* in at least specific parts of the nucleotide sequence, such as including the 3' region of the respective promoter nucleotide sequence, preferably a part with a specific length up to the 3' end of the respective promoter nucleotide sequence, such as a part with a length of at least 200 bp, preferably at least 250 bp, preferably at least 300 bp, more preferred at least 400 bp, at least 500 bp, at least 600 bp, at least 700 bp, at least 800 bp, at least 900 bp, or at least 1000 bp, and analogs derived from species other than *Pichia pastoris*. Specifically at least those parts are preferably homologous within the range of 300-1000 bp, including the 3' terminal sequence of the respective promoter nucleotide sequence.

Analogous sequences are typically derived from other species or strains. It is expressly understood that any of the analogous promoter sequences of the present invention that are derived from species other than *Pichia pastoris* may comprise a homologous sequence, i.e. a sequence with a certain homology as described herein. Thus, the term "homologous" may also include analogous sequences. On the other hand, it is understood that the invention also refers to analogous sequences and homologs thereof that comprise a certain homology.

"Percent (%) identity" with respect to the nucleotide sequence of a gene is defined as the percentage of nucleotides in a candidate DNA sequence that is identical with the nucleotides in the DNA sequence, after aligning the sequence and introducing gaps, if necessary, to achieve the maximum percent sequence identity, and not considering any conservative substitutions as part of the sequence identity. Alignment for purposes of determining percent nucleotide sequence identity can be achieved in various ways that are within the skill in the art, for instance, using publicly available computer software. Those skilled in the art can determine appropriate parameters for measuring alignment, including any algorithms needed to achieve maximal alignment over the full length of the sequences being compared.

The term "mutagenesis" as used in the context of the present invention shall refer to a method of providing mutants of a nucleotide sequence, e.g. through insertion, deletion and/or substitution of one or more nucleotides, so to obtain variants thereof with at least one change in the non-coding or coding region. Mutagenesis may be through random, semi-random or site directed mutation. Typically large randomized gene libraries are produced with a high gene diversity, which may be selected according to a specifically desired genotype or phenotype.

The term "protein of interest (POI)" as used herein refers to a polypeptide or a protein that is produced by means of recombinant technology in a host cell. More specifically, the protein may either be a polypeptide not naturally occurring in the host cell, i.e. a heterologous protein, or else may be native to the host cell, i.e. a homologous protein to the host cell, but is produced, for example, by transformation with a self replicating vector containing the nucleic acid sequence encoding the POI, or upon integration by recombinant techniques of one or more copies of the nucleic acid sequence encoding the POI into the genome of the host cell, or by recombinant modification of one or more regulatory sequences controlling the expression of the gene encoding the POI, e.g. of the promoter sequence. In some cases the term POI as used herein also refers to any metabolite product by the host cell as mediated by the recombinantly expressed protein.

The term "recombinant" as used herein shall mean "being prepared by or the result of genetic engineering". Thus, a "recombinant microorganism" comprises at least one "recombinant nucleic acid". A recombinant microorganism specifically comprises an expression vector or cloning vector, or it has been genetically engineered to contain a recombinant nucleic acid sequence. A "recombinant protein" is produced by expressing a respective recombinant nucleic acid in a host. A "recombinant promoter" is a genetically engineered non-coding nucleotide sequence suitable for its use as a functionally active promoter as described herein.

It surprisingly turned out that eukaryotic cells are capable of inducing the production of a POI by limiting the availability of the carbon source. Carbon starvation conditions were found to trigger induction of strong promoter activity, which was heretofore unknown in the art. The MLS1 promoter of *Pichia pastoris* as described in US2008299616A1 to be derepressed under sugar limitations, was actually a comparably weak regulatable promoter for POI production. It was therefore surprising that such strong regulatable promoter of *P. pastoris* could be identified and could be used in eukaryotic production cell lines, in particular for recombinant POI production.

Though the 9.43 Mbp genomic sequence of the GS115 strain of *P. pastoris* has been determined and disclosed in US20110021378A1, the properties of individual sequences, such as promoter sequences, have not been investigated in detail. For instance, the pG4 sequence (SEQ ID 4) as described herein was identified as a promoter sequence in US20110021378A1, however, its regulatable properties or its use under carbon starvation conditions were not known. It was even surprising that such promoter could be effectively used in the method according to the invention. Regulated promoters of the prior art such as used in industrial scale POI production were mainly derived from the methanol metabolic pathway and needed the addition of methanol to induce POI production, which is often not desired. The method according to the invention has the advantage that it may provide for an increased production by an enhanced expression, and has the reduced risk of contamination due to the specific promoter regulation, in particular when using a chemically defined medium, free of methanol.

It turned out that the regulatable promoter according to the invention would exert their regulatable activity only upon use of very specific culture media suitable for establishing promoter repressing and de-repressing conditions. As an example, *P. pastoris* could be successfully cultivated under conditions of an industrial production process. First a batch culture on a basal carbon source, such as glycerol, was employed, followed by a fed batch with limited feed of a supplemental carbon source, such as glucose. Samples were taken close to the end of the first batch phase, and in limited growth conditions, e.g. using a limited amount of supplemental carbon source. Transcriptome analysis with DNA micoarrays revealed specific genes that are strongly active on the supplemental carbon source and weak or inactive in the presence of surplus carbon, i.e. the basal carbon source in excess amount. At least six promoter sequences were identified as regulatable promoter according to the invention, i.e. pG1 (SEQ ID 1), pG3 (SEQ ID 2), pG4 (SEQ ID 4), pG6 (SEQ ID 3), pG7 (SEQ ID 5) and pG8 (SEQ ID 6). The comparable MLS1 or ICL1 promoter of the prior art was only weak, with less than 1/10 of the strength of the pG1 promoter, and no detectable regulation.

The features of repressing recombinant gene expression on the basal carbon source, and strong expression on limited supplemental carbon source, i.e. induction by substrate change could be verified in fermentation processes.

The nucleotide sequences that could be used as regulatory sequences according to the invention, which would provide for an improved recombinant protein production, can be obtained from a variety of sources. The origin of the promoter according to the invention is preferably from a yeast cell, most preferably from methylotrophic yeast such as from the *Pichia* genus or from the *P. pastoris* species, which promoter may then be used as a parent sequence to produce suitable variants, e.g. mutants or analogs.

It is contemplated that a series of yeast cells, in particular of *Pichia* strains, may be suitable to obtain respective promoter sequences that are responsible for protein production under carbon starving conditions, or respective analogs in different species.

Variants of the identified *P. pastoris* promoter, including functionally active variants, such as homologs and analogs may be produced employing standard techniques. The promoter may e.g. be modified to generate promoter variants with altered expression levels and regulatory properties.

For instance, a promoter library may be prepared by mutagenesis of the promoter sequences according to the invention, which may be used as parent molecules, e.g. to fine-tune the gene expression in eukaryotic cells by analysing variants for their expression under different fermentation strategies and selecting suitable variants. A synthetic library of variants may be used, e.g. to select a promoter matching the requirements for producing a selected POI. Such variants may have increased expression efficiency in eukaryotic host cells and high expression upon depletion of a carbon source.

The differential fermentation strategies would distinguish between a growth phase, such as step a) according to the present invention, and a production phase, such as step b).

Growth and/or production can suitably take place in batch mode, fed-batch mode or continuous mode. Any suitable bioreactor can be used, including batch, fed-batch, continuous, stirred tank reactor, or airlift reactor.

It is advantageous to provide for the fermentation process on a pilot or industrial scale. The industrial process scale would preferably employ volumina of at least 10 L, specifically at least 50 L, preferably at least 1 $m^3$, preferably at least 10 $m^3$, most preferably at least 100 $m^3$.

Production conditions in industrial scale are preferred, which refer to e.g. fed batch cultivation in reactor volumes of 100 L to 10 $m^3$ or larger, employing typical process times of several days, or continuous processes in fermenter volumes of appr. 50-1000 L or larger, with dilution rates of approximately 0.02-0.15 $h^{-1}$.

The suitable cultivation techniques may encompass cultivation in a bioreactor starting with a batch phase, followed by a short exponential fed batch phase at high specific growth rate, further followed by a fed batch phase at a low specific growth rate.

Another suitable cultivation technique may encompass a batch phase followed by a continuous cultivation phase at a low dilution rate.

A preferred embodiment of the invention includes a batch culture to provide biomass followed by a fed-batch culture for high yields POI production.

For example, the cell line may be grown in step a) according to the invention on glycerol or glucose to obtain biomass.

It is preferred to cultivate the host cell line according to the invention in a bioreactor under growth conditions to obtain a cell density of at least 1 g/L cell dry weight, more preferably at least 10 g/L cell dry weight, preferably at least 20 g/L cell dry weight. It is advantageous to provide for such yields of biomass production on a pilot or industrial scale.

A growth medium allowing the accumulation of biomass, specifically a basal growth medium, typically comprises a carbon source, a nitrogen source, a source for sulphur and a source for phosphate. Typically, such a medium comprises furthermore trace elements and vitamins, and may further comprise amino acids, peptone or yeast extract.

Preferred nitrogen sources include $NH_4H_2PO_4$, or $NH_3$ or $(NH4)_2SO_4$;

Preferred sulphur sources include $MgSO_4$, or $(NH4)_2SO_4$ or $K_2SO_4$;

Preferred phosphate sources include $NH_4H_2PO_4$, or $H_3PO_4$ or $NaH_2PO_4$, $KH_2PO_4$, $Na_2HPO_4$ or $K_2HPO_4$;

Further typical medium components include KCl, $CaCl_2$, and Trace elements such as: Fe, Co, Cu, Ni, Zn, Mo, Mn, I, B;

Preferably the medium is supplemented with vitamin $B_7$;

A typical growth medium for *P. pastoris* comprises glycerol or glucose, $NH_4H_2PO_4$, $MgSO_4$, KCl, $CaCl_2$, biotin, and trace elements.

In the production phase a production medium is specifically used with only a limited amount of a supplemental carbon source.

Preferably the host cell line is cultivated in a mineral medium with a suitable carbon source, thereby further simplifying the isolation process significantly. An example of a preferred mineral medium is one containing an utilizable carbon source (e.g. glucose, glycerol or methanol), salts containing the macro elements (potassium, magnesium, calcium, ammonium, chloride, sulphate, phosphate) and trace elements (copper, iodide, manganese, molybdate, cobalt, zinc, and iron salts, and boric acid), and optionally vitamins or amino acids, e.g. to complement auxotrophies.

The cells are cultivated under conditions suitable to effect expression of the desired POI, which can be purified from the cells or culture medium, depending on the nature of the expression system and the expressed protein, e.g. whether the protein is fused to a signal peptide and whether the protein is soluble or membrane-bound. As will be understood by the skilled artisan, cultivation conditions will vary according to factors that include the type of host cell and particular expression vector employed.

Induction of the POI production by the promoter according to the invention is preferably controlled by cultivating the cells on a supplemental carbon source in a limited amount as the sole source of carbon and energy. The cells grow very slowly under carbon limited conditions, but produce high yields of the POI under the control of the regulatable promoter.

The difference in the promoter activity specifically is at least 2 fold, preferably at least 5 fold, more preferred at least 10 fold, more preferred at least 20 fold, more preferably at least 30, 40, 50, or 100 fold in the de-repressed state compared to the repressed state.

By selecting the suitable promoter sequence according to the invention, optionally in combination with further preferred regulatory sequences, it is possible to provide for, under comparable conditions, at least the same, or at least about a 1.5-fold, or at least about 2-fold, or at least about a 5-fold, 10-fold, or at least up to about a 15-fold activity as represented by the promoter activity or transcription strength, or regulated by the promoter strength relative to a GAP promoter that is homologous to the production cell, a native pGAP, or isolated from *P. pastoris*.

A typical production medium comprises the supplemental carbon source, and further $NH_4H_2PO_4$, $MgSO_4$, KCl, $CaCl_2$, biotin, and trace elements.

For example the feed of the supplemental carbon source added to the fermentation may comprise a carbon source with up to 50 wt % fermentable sugars. The low feed rate of the supplemental medium will limit the effects of product inhibition on the cell growth, thus a high product yield based on substrate provision will be possible.

The fermentation preferably is carried out at a pH ranging from 3 to 7.5.

Typical fermentation times are about 24 to 120 hours with temperatures in the range of 20° C. to 35° C., preferably 22-30° C.

In general, the recombinant nucleic acids or organisms as referred to herein may be produced by recombination techniques well known to a person skilled in the art. In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982).

According to a preferred embodiment of the present invention, a recombinant construct is obtained by ligating the promoter and relevant genes into a vector. These genes can be stably integrated into the host cell genome by transforming the host cell using such vectors.

Expression vectors may include but are not limited to cloning vectors, modified cloning vectors and specifically designed plasmids. The preferred expression vector as used in the invention may be any expression vector suitable for expression of a recombinant gene in a host cell and is selected depending on the host organism. The recombinant expression vector may be any vector which is capable of replicating in or integrating into the genome of the host organisms, also called host vector.

In the present invention, it is preferred to use plasmids derived from pPUZZLE as the vector.

Appropriate expression vectors typically comprise further regulatory sequences suitable for expressing DNA encoding a POI in a eukaryotic host cell. Examples of regulatory sequences include operators, enhancers, ribosomal binding sites, and sequences that control transcription and translation initiation and termination. The regulatory sequences may be operably linked to the DNA sequence to be expressed.

To allow expression of a recombinant nucleotide sequence in a host cell, the expression vector may provide the promoter according to the invention adjacent to the 5' end of the coding sequence, e.g. upstream from a signal peptide gene. The transcription is thereby regulated and initiated by this promoter sequence.

A signal peptide may be a heterologous signal peptide or a hybrid of a native and a heterologous signal peptide, and may specifically be heterologous or homologous to the host organism producing the protein. The function of the signal peptide is to allow the POI to be secreted to enter the endoplasmatic reticulum. It is usually a short (3-60 amino acids long) peptide chain that directs the transport of a protein outside the plasma membrane, thereby making it easy to separate and purify the heterologous protein. Some signal peptides are cleaved from the protein by signal peptidase after the proteins are transported.

Exemplary signal peptides are signal sequences from *S. cerevisiae* alpha-mating factor prepro peptide and the signal peptide from the *P. pastoris* acid phosphatase gene (PHO1).

A promoter sequence is understood to be operably linked to a coding sequence, if the promotor controls the transcription of the coding sequence. If a promoter sequence is not natively associated with the coding sequence, its transcription is either not controlled by the promoter in native (wild-type) cells or the sequences are recombined with different contiguous sequences.

To prove the function of the relevant sequences, expression vectors comprising one or more of the regulatory elements may be constructed to drive expression of a POI, and the expressed yield is compared to constructs with conventional regulatory elements. A detailed description of the experimental procedure can be found in the examples below. The identified genes may be amplified by PCR from *P. pastoris* using specific nucleotide primers, cloned into an expression vector and transformed into a eukaryotic cell line, e.g. using a yeast vector and a strain of *P. pastoris*, for high level production of various different POI. To estimate the effect of the promoter according to the invention on the amount of recombinant POI so produced, the eukaryotic cell line may be cultured in shake flask experiments and fedbatch or chemostat fermentations in comparison with strains comprising a conventional, non carbon source regulatable promoter, such as for example the standard pGAP promoter in the respective cell. In particular, the choice of the promoter has a great impact on the recombinant protein production.

Preferred methods of transformation for the uptake of the recombinant DNA fragment by the microorganism include chemical transformation, electroporation or transformation by protoplastation. Transformants according to the present invention can be obtained by introducing such a vector DNA, e.g. plasmid DNA, into a host and selecting transformants which express the relevant protein or host cell metabolite with high yields.

The POI can be produced using the recombinant host cell line by culturing a transformant, thus obtained in an appropriate medium, isolating the expressed product or metabolite from the culture, and optionally purifying it by a suitable method.

Transformants according to the present invention can be obtained by introducing such a vector DNA, e.g. plasmid DNA, into a host and selecting transformants which express the POI or the host cell metabolite with high yields. Host cells are treated to enable them to incorporate foreign DNA by methods conventionally used for transformation of eukaryotic cells, such as the electric pulse method, the protoplast method, the lithium acetate method, and modified methods thereof. *P. pastoris* is preferably transformed by electroporation.

The preferred host cell line according to the invention maintains the genetic properties employed according to the invention, and the production level remains high, e.g. at least at a μg level, even after about 20 generations of cultivation, preferably at least 30 generations, more preferably at least 40 generations, most preferred of at least 50 generations. The stable recombinant host cell is considered a great advantage when used for industrial scale production.

Several different approaches for the production of the POI according to the method of the invention are preferred. Substances may be expressed, processed and optionally secreted by transforming a eukaryotic host cell with an expression vector harbouring recombinant DNA encoding a relevant protein and at least one of the regulatory elements as described above, preparing a culture of the transformed cell, growing the culture, inducing transcription and POI production, and recovering the product of the fermentation process.

The POI is preferably expressed employing conditions to produce yields of at least 1 mg/L, preferably at least 10 mg/L, preferably at least 100 mg/L, most preferred at least 1 g/L.

The host cell according to the invention is preferably tested for its expression capacity or yield by the following test: ELISA, activity assay, H PLC, or other suitable tests.

It is understood that the methods disclosed herein may further include cultivating said recombinant host cells under conditions permitting the expression of the POI, preferably in the secreted form or else as intracellular product. A recombinantly produced POI or a host cell metabolite can then be isolated from the cell culture medium and further purified by techniques well known to a person skilled in the art.

The POI produced according to the invention typically can be isolated and purified using state of the art techniques, including the increase of the concentration of the desired POI and/or the decrease of the concentration of at least one impurity.

If the POI is secreted from the cells, it can be isolated and purified from the culture medium using state of the art techniques. Secretion of the recombinant expression products from the host cells is generally advantageous for reasons that include facilitating the purification process, since the products are recovered from the culture supernatant rather than from the complex mixture of proteins that results when yeast cells are disrupted to release intracellular proteins.

The cultured transformant cells may also be ruptured sonically or mechanically, enzymatically or chemically to obtain a cell extract containing the desired POI, from which the POI is isolated and purified.

As isolation and purification methods for obtaining a recombinant polypeptide or protein product, methods, such as methods utilizing difference in solubility, such as salting out and solvent precipitation, methods utilizing difference in molecular weight, such as ultrafiltration and gel electrophoresis, methods utilizing difference in electric charge, such as ion-exchange chromatography, methods utilizing specific affinity, such as affinity chromatography, methods utilizing difference in hydrophobicity, such as reverse phase high performance liquid chromatography, and methods utilizing difference in isoelectric point, such as isoelectric focusing may be used.

The highly purified product is essentially free from contaminating proteins, and preferably has a purity of at least 90%, more preferred at least 95%, or even at least 98%, up to 100%. The purified products may be obtained by purification of the cell culture supernatant or else from cellular debris.

As isolation and purification methods the following standard methods are preferred: Cell disruption (if the POI is obtained intracellularly), cell (debris) separation and wash by Microfiltration or Tangential Flow Filter (TFF) or centrifugation, POI purification by precipitation or heat treatment, POI activation by enzymatic digest, POI purification by chromatography, such as ion exchange (IEX), hydrophobic ointeraction chromatography (HIC), Affinity chromatography, size exclusion (SEC) or HPLC Chromatography, POI precipitation of concentration and washing by ultrafiltration steps.

The isolated and purified POI can be identified by conventional methods such as Western blot, HPLC, activity assay, or ELISA.

The POI can be any eukaryotic, prokaryotic or synthetic polypeptide. It can be a secreted protein or an intracellular protein. The present invention also provides for the recombinant production of functional homologs, functional equivalent variants, derivatives and biologically active fragments of naturally occurring proteins. Functional homologs are preferably identical with or correspond to and have the functional characteristics of a sequence.

A POI referred to herein may be a product homologous to the eukaryotic host cell or heterologous, preferably for therapeutic, prophylactic, diagnostic, analytic or industrial use.

The POI is preferably a heterologous recombinant polypeptide or protein, produced in a eukaryotic cell, preferably a yeast cell, preferably as secreted proteins. Examples of preferably produced proteins are immunoglobulins, immunoglobulin fragments, aprotinin, tissue factor pathway inhibitor or other protease inhibitors, and insulin or insulin precursors, insulin analogues, growth hormones, interleukins, tissue plasminogen activator, transforming growth factor a or b, glucagon, glucagon-like peptide 1 (GLP-1), glucagon-like peptide 2 (GLP-2), GRPP, Factor VII, Factor VIII, Factor XIII, platelet-derived growth factor1, serum albumin, enzymes, such as lipases or proteases, or a functional homolog, functional equivalent variant, derivative and biologically active fragment with a similar function as the native protein. The POI may be structurally similar to the native protein and may be derived from the native protein by addition of one or more amino acids to either or both the C- and N-terminal end or the side-chain of the native protein, substitution of one or more amino acids at one or a number of different sites in the native amino acid sequence, deletion of one or more amino acids at either or both ends of the native protein or at one or several sites in the amino acid sequence, or insertion of one or more amino acids at one or more sites in the native amino acid sequence. Such modifications are well known for several of the proteins mentioned above.

A POI can also be selected from substrates, enzymes, inhibitors or cofactors that provide for biochemical reactions in the host cell, with the aim to obtain the product of said biochemical reaction or a cascade of several reactions, e.g. to obtain a metabolite of the host cell. Exemplary products can be vitamins, such as riboflavin, organic acids, and alcohols, which can be obtained with increased yields following the expression of a recombinant protein or a POI according to the invention.

In general, the host cell, which expresses a recombinant product, can be any eukaryotic cell suitable for recombinant expression of a POI.

Examples of preferred mammalian cells are BHK, CHO (CHO-DG44, CHO-DUXB11, CHO-DUKX, CHO-K1, CHOK1 SV, CHO-S), HeLa, HEK293, MDCK, NIH3T3, NS0, PER.C6, SP2/0 and VERO cells.

Examples of preferred yeast cells used as host cells according to the invention include but are not limited to the *Saccharomyces* genus (e.g. *Saccharomyces cerevisiae*), the *Pichia* genus (e.g. *P. pastoris*, or *P. methanolica*), the *Komagataella* genus (*K. pastoris, K. pseudopastoris* or *K. phaffii*), *Hansenula polymorpha* or *Kluyveromyces lactis*.

Newer literature divides and renames *Pichia pastoris* into *Komagataella pastoris, Komagataella phaffii* and *Komagataella pseudopastoris*. Herein *Pichia pastoris* is used synonymously for all, *Komagataella pastoris, Komagataella phaffii* and *Komagataella pseudopastoris*.

The preferred yeast host cells are derived from methylotrophic yeast, such as from *Pichia* or *Komagataella*, e.g. *Pichia pastoris*, or *Komagataella pastoris*, or *K. phaffii*, or *K. pseudopastoris*. Examples of the host include yeasts such as *P. pastoris*. Examples of *P. pastoris* strains include CBS 704 (=NRRL Y-1603=DSMZ 70382), CBS 2612 (=NRRL Y-7556), CBS 7435 (=NRRL Y-11430), CBS 9173-9189 (CBS strains: CBS-KNAW Fungal Biodiversity Centre, Centraalbureau voor Schimmelcultures, Utrecht, The Netherlands), and DSMZ 70877 (German Collection of Microorganisms and Cell Cultures), but also strains from Invitrogen, such as X-33, GS115, KM71 and SMD1168. Examples of *S. cerevisiae* strains include W303, CEN.PK and the BY-series (EUROSCARF collection). All of the strains described above have been successfully used to produce transformants and express heterologous genes.

A preferred yeast host cell according to the invention, such as a *P. pastoris* or *S. cerevisiae* host cell, contains a heterologous or recombinant promoter sequences, which may be derived from a *P. pastoris* or *S. cerevisiae* strain, different from the production host. In another specific embodiment the host cell according to the invention comprises a recombinant expression construct according to the invention comprising the promoter originating from the same genus, species or strain as the host cell.

The promoter may be a promoter according to the invention or any other DNA sequence which shows transcriptional activity in the host cell and may be derived from genes encoding proteins either homologous or heterologous to the host. The promoter is preferably derived from a gene encoding a protein homologous to the host cell.

For example, a promoter according to the invention may be derived from yeast, such as a *S. cerevisiae* strain, and be used to express a POI in a yeast. A specifically preferred embodiment relates to a promoter according to the invention originating from *P. pastoris* for use in a method to produce a recombinant POI in a *P. pastoris* producer host cell line. The homologous origin of the nucleotide sequence facilitates its incorporation into the host cell of the same genus or species, thus enabling stable production of a POI, possibly with increased yields in industrial manufacturing processes. Also, functionally active variants of the promoter from other suitable yeasts or other fungi or from other organisms such as vertebrates or plants can be used.

If the POI is a protein homologous to the host cell, i.e. a protein which is naturally occurring in the host cell, the expression of the POI in the host cell may be modulated by the exchange of its native promoter sequence with a promoter sequence according to the invention.

This purpose may be achieved e.g. by transformation of a host cell with a recombinant DNA molecule comprising homologous sequences of the target gene to allow site specific recombination, the promoter sequence and a selective marker suitable for the host cell. The site specific recombination shall take place in order to operably link the promoter sequence with the nucleotide sequence encoding the POI. This results in the expression of the POI from the promoter sequence according to the invention instead of from the native promoter sequence.

In a specifically preferred embodiment of the invention the promoter sequence has an increased promoter activity relative to the native promoter sequence of the POI.

According to the invention it is preferred to provide a *P. pastoris* host cell line comprising a promoter sequence according to the invention operably linked to the nucleotide sequence coding for the POI.

According to the invention it is also possible to provide a wildcard vector or host cell according to the invention, which comprises a promoter according to the invention, and which is ready to incorporate a gene of interest encoding a POI. The wildcard cell line is, thus, a preformed host cell line, which is characterized for its expression capacity. This follows an innovative "wildcard" platform strategy for the generation of producer cell lines, for the POI production, e.g. using site-specific recombinase-mediated cassette exchange. Such a new host cell facilitates the cloning of a gene of interest (GOI), e.g. into predetermined genomic expression hot spots within days in order to get reproducible, highly efficient production cell lines.

According to a preferred embodiment the method according to the invention employs a recombinant nucleotide sequence encoding the POI, which is provided on a plasmid suitable for integration into the genome of the host cell, in a single copy or in multiple copies per cell. The recombinant nucleotide sequence encoding the POI may also be provided on an autonomously replicating plasmid in a single copy or in multiple copies per cell.

The preferred method according to the invention employs a plasmid, which is a eukaryotic expression vector, preferably a yeast expression vector. Expression vectors may include but are not limited to cloning vectors, modified cloning vectors and specifically designed plasmids. The preferred expression vector as used in the invention may be any expression vector suitable for expression of a recombinant gene in a host cell and is selected depending on the host organism. The recombinant expression vector may be any vector which is capable of replicating in or integrating into the genome of the host organisms, also called host vector, such as a yeast vector, which carries a DNA construct according to the invention. A preferred yeast expression vector is for expression in yeast selected from the group consisting of methylotrophic yeasts represented by the genera *Hansenula, Pichia, Candida* and *Torulopsis*.

In the present invention, it is preferred to use plasmids derived from pPICZ, pGAPZ, pPIC9, pPICZalfa, pGAPZalfa, pPIC9K, pGAPHis or pPUZZLE as the vector.

According to a preferred embodiment of the present invention, a recombinant construct is obtained by ligating the relevant genes into a vector. These genes can be stably integrated into the host cell genome by transforming the host cell using such vectors. The polypeptides encoded by the genes can be produced using the recombinant host cell line by culturing a transformant, thus obtained in an appropriate medium, isolating the expressed POI from the culture, and purifying it by a method appropriate for the expressed product, in particular to separate the POI from contaminating proteins.

Expression vectors may comprise one or more phenotypic selectable markers, e.g. a gene encoding a protein that confers antibiotic resistance or that supplies an autotrophic requirement. Yeast vectors commonly contain an origin of replication from a yeast plasmid, an autonomously replicating sequence (ARS), or alternatively, a sequence used for integration into the host genome, a promoter region, sequences for polyadenylation, sequences for transcription termination, and a selectable marker.

The procedures used to ligate the DNA sequences, e.g. coding for the precursing sequence and/or the POI, the promoter and the terminator, respectively, and to insert them into suitable vectors containing the information necessary for integration or host replication, are well known to persons skilled in the art, e.g. described by J. Sambrook et al., "Molecular Cloning 2nd ed.", Cold Spring Harbor Laboratory Press (1989).

It will be understood that the vector, which uses the regulatory elements according to the invention and/or the POI as an integration target, may be constructed either by first preparing a DNA construct containing the entire DNA sequence coding for the regulatory elements and/or the POI and subsequently inserting this fragment into a suitable expression vector, or by sequentially inserting DNA fragments containing genetic information for the individual elements, such as the signal, leader or heterologous protein, followed by ligation.

Also multicloning vectors, which are vectors having a multicloning site, can be used according to the invention, wherein a desired heterologous gene can be incorporated at a multicloning site to provide an expression vector. In expression vectors, the promoter is placed upstream of the gene of the POI and regulates the expression of the gene. In the case of multicloning vectors, because the gene of the POI is introduced at the multicloning site, the promoter is placed upstream of the multicloning site.

The DNA construct as provided to obtain a recombinant host cell according to the invention may be prepared synthetically by established standard methods, e.g. the phosphoramidite method. The DNA construct may also be of genomic or cDNA origin, for instance obtained by preparing a genomic or cDNA library and screening for DNA sequences coding for all or part of the polypeptide of the invention by hybridization using synthetic oligonucleotide probes in accordance with standard techniques (Sambrook et al., Molecular Cloning: A Laboratory Manual, Cold Spring Harbor, 1989). Finally, the DNA construct may be of mixed synthetic and genomic, mixed synthetic and cDNA or mixed genomic and cDNA origin prepared by annealing fragments of synthetic, genomic or cDNA origin, as appropriate, the fragments corresponding to various parts of the entire DNA construct, in accordance with standard techniques.

In another preferred embodiment, the yeast expression vector is able to stably integrate in the yeast genome, e. g. by homologous recombination.

A transformant host cell according to the invention obtained by transforming the cell with the regulatory elements according to the invention and/or the POI genes may preferably first be cultivated at conditions to grow efficiently to a large cell number without the burden of expressing a heterologous protein. When the cell line is prepared for the POI expression, cultivation techniques are chosen to produce the expression product.

The subject matter of the following definitions is considered embodiments of the present invention:

1. A method of producing a protein of interest (POI) by culturing a recombinant eukaryotic cell line comprising an expression construct comprising a regulatable promoter and a nucleic acid molecule encoding a POI under the transcriptional control of said promoter, comprising the steps
   a) cultivating the cell line with a basal carbon source repressing the promoter,
   b) cultivating the cell line with no or a limited amount of a supplemental carbon source de-repressing the promoter to induce production of the POI at a transcription rate of at least 15% as compared to the native pGAP promoter of the cell, and
   c) producing and recovering the POI.

2. Method according to definition 1, wherein the basal carbon source is selected from the group consisting of glucose, glycerol, ethanol and complex nutrient material.

3. Method according to definition 1 or 2, wherein the supplemental carbon source is a hexose such as glucose, fructose, galactose or mannose, a disaccharide, such as saccharose, an alcohol, such as glycerol or ethanol, or a mixture thereof.

4. Method according to any of definitions 1 to 3, wherein the basal carbon source is glycerol, and the supplemental carbon source is glucose.

5. Method according to any of definitions 1 to 4, wherein step b) employs a feed medium that provides for no or the supplemental carbon source in a limited amount, preferably 0-1 g/L in the culture medium.

6. Method according to definition 5, wherein the feed medium is chemically defined and methanol-free.

7. Method according to any of definitions 1 to 6, wherein the limited amount of the supplemental carbon source is growth limiting to keep the specific growth rate within the range of $0.02$ $h^{-1}$ to $0.2$ $h^{-1}$, preferably $0.02$ $h^{-1}$ to $0.15$ $h^{-1}$.

8. Method according to definition 7, wherein the limited amount of the supplemental source provides for a residual amount in the cell culture which is below the detection limit.

9. Method according to any of definitions 1 to 8, wherein the promoter is capable of controlling the transcription of a gene in a wild-type eukaryotic cell, which gene is selected from the group consisting of G1 (SEQ ID 7), G3 (SEQ ID 8), G4 (SEQ ID 9), G6 (SEQ ID 10), G7 (SEQ ID 11) or G8 (SEQ ID 12), or a functionally active variant thereof.

10. Method according to definition 9, wherein said functionally active variants are selected from the group consisting of homologs with at least about 60% nucleotide sequence identity, homologs obtainable by modifying the parent nucleotide sequence by insertion, deletion or substitution of one or more nucleotides within the sequence or at either or both of the distal ends of the sequence, preferably comprising or consisting of a nucleotide sequence of at least 200 bp, and analogs derived from species other than *Pichia pastoris*.

11. Method according to definition 9 or 10, wherein the functionally active variant of pG1 is selected from the group consisting of pG1a (SEQ ID 41), pG1b (SEQ ID 42), pG1c (SEQ ID 43), pG1d (SEQ ID 44), pG1e (SEQ ID 45) and pG1f (SEQ ID 46).

12. Method according to any of definitions 1 to 11, wherein the promoter is a *Pichia pastoris* promoter or a functionally active variant thereof.

13. Method according to any of definitions 1 to 12, wherein the cell line is selected from the group consisting of mammalian, insect, yeast, filamentous fungi and plant cell lines, preferably a yeast.

14. Method according to definition 13, wherein the yeast is selected from the group consisting of *Pichia, Candida, Torulopsis, Arxula, Hensenula, Yarrowia, Kluyveromyces, Saccharomyces, Komagataella*, preferably a methylotrophic yeast.

15. Method according to definition 14, wherein the yeast is *Pichia pastoris, Komagataella pastoris, K. phaffii,* or *K. pseudopastoris*.

16. Method according to any of definitions 1 to 15, wherein the promoter is not natively associated with the nucleotide sequence encoding the POI.

17. Method according to any of definitions 1 to 16, wherein the POI is a heterologous protein, preferably selected from therapeutic proteins, including antibodies or fragments thereof, enzymes and peptides, protein antibiotics, toxin fusion proteins, carbohydrate-protein conjugates, structural proteins, regulatory proteins, vaccines and vaccine like proteins or particles, process enzymes, growth factors, hormones and cytokines, or a metabolite of a POI.

18. Method according to any of definitions 1 to 17, wherein the POI is a eukaryotic protein, preferably a mammalian protein.

19. Method according to any of definitions 1 to 18, wherein the POI is a multimeric protein, preferably a dimer or tetramer.

20. Method according to any of definitions 1 to 19, wherein the POI is an antigen binding molecule such as an antibody, or a fragment thereof.

21. Method according to any of definitions 1 to 20, wherein a fermentation product is manufactured using the POI, a metabolite or a derivative thereof.

22. Method for controlling the expression of a POI in a recombinant eukaryotic cell under the transcriptional control of a carbon source regulatable promoter having a transcription strength of at least 15% as compared to the native pGAP promoter of the cell, wherein the expression is induced under conditions limiting the carbon source.

23. Method of producing a POI in a recombinant eukaryotic cell under the transcriptional control of a carbon source regulatable promoter, wherein said promoter has a transcription strength of at least 15% as compared to the native pGAP promoter of the cell.

24. Method according to any of definitions 1 to 23, wherein the regulatable promoter comprises a nucleic acid sequence selected from the group consisting of
   a) pG1 (SEQ ID 1), pG3 (SEQ ID 2), pG4 (SEQ ID 4), pG6 (SEQ ID 3), pG7 (SEQ ID 5), or pG8 (SEQ ID 6);
   b) a sequence having at least 60% homology to pG1 (SEQ ID 1), pG3 (SEQ ID 2), pG4 (SEQ ID 4), pG6 (SEQ ID 3), pG7 (SEQ ID 5), or pG8 (SEQ ID 6);
   c) a sequence which hybridizes under stringent conditions to pG1 (SEQ ID 1), pG3 (SEQ ID 2), pG4 (SEQ ID 4), pG6 (SEQ ID 3), pG7 (SEQ ID 5), or pG8 (SEQ ID 6); and
   d) a fragment or variant derived from a), b) or c),
wherein said promoter is a functionally active promoter, which is a carbon source regulatable promoter capable of expressing a POI in a recombinant eukaryotic cell at a transcription rate of at least 15% as compared to the native pGAP promoter of the cell.

25. Method according to definition 24, wherein the variant of pG1 (SEQ ID 1), pG3 (SEQ ID 2), pG4 (SEQ ID 4), pG6 (SEQ ID 3), pG7 (SEQ ID 5), or pG8 (SEQ ID 6), is a functionally active variant selected from the group consisting of homologs with at least about 60% nucleotide sequence identity, homologs obtainable by modifying the parent nucleotide sequence by insertion, deletion or substitution of one or more nucleotides within the sequence or at either or both of the distal ends of the sequence, preferably comprising or consisting of a nucleotide sequence of at least 200 bp, and analogs derived from species other than *Pichia pastoris*.

26. Method according to definition 24 or 25, wherein the functionally active variant of pG1 is selected from the group consisting of pG1a (SEQ ID 41), pG1b (SEQ ID 42), pG1c (SEQ ID 43), pG1d (SEQ ID 44), pG1e (SEQ ID 45) and pG1f (SEQ ID 46).

27. An isolated nucleic acid comprising a nucleic acid sequence selected from the group consisting of
   a) pG1 (SEQ ID 1), pG3 (SEQ ID 2), pG6 (SEQ ID 3), pG7 (SEQ ID 5), or pG8 (SEQ ID 6);
   b) a sequence having at least 60% homology to pG1 (SEQ ID 1), pG3 (SEQ ID 2), pG6 (SEQ ID 3), pG7 (SEQ ID 5), or pG8 (SEQ ID 6);
   c) a sequence which hybridizes under stringent conditions to pG1 (SEQ ID 1), pG3 (SEQ ID 2), pG6 (SEQ ID 3), pG7 (SEQ ID 5), or pG8 (SEQ ID 6); and
   d) a fragment or variant derived from a), b) or c),
wherein said nucleic acid comprises a functionally active promoter, which is a carbon source regulatable promoter capable of expressing a POI in a recombinant eukaryotic cell at a transcription rate of at least 15% as compared to the native pGAP promoter of the cell.

28. Nucleic acid according to definition 27, wherein the variant of pG1 (SEQ ID 1), pG3 (SEQ ID 2), pG6 (SEQ ID 3), pG7 (SEQ ID 5), or pG8 (SEQ ID 6) is a functionally active variant selected from the group consisting of homologs with at least about 60% nucleotide sequence identity, homologs obtainable by modifying the parent nucleotide sequence by insertion, deletion or substitution of one or more nucleotides within the sequence or at either or both of the distal ends of the sequence, preferably with a nucleotide sequence of at least 200 bp, and analogs derived from species other than *Pichia pastoris*.

29. Nucleic acid according to definition 27 or 28, wherein the functionally active variant of pG1 is selected from the group consisting of pG1a (SEQ ID 41), pG1b (SEQ ID 42), pG1c (SEQ ID 43), pG1d (SEQ ID 44), pG1e (SEQ ID 45) and pG1f (SEQ ID 46).

30. An expression construct comprising a nucleic acid according to any of the definitions 27 to 29 operably linked to a nucleotide sequence encoding a POI under the transcriptional control of said promoter, which nucleic acid is not natively associated with the nucleotide sequence encoding the POI.

31. Vector comprising the construct according to definition 30.

32. A recombinant eukaryotic cell comprising the construct of definition 30, or the vector of definition 31.

33. A cell according to definition 31, which is selected from the group consisting of mammalian, insect, yeast, filamentous fungi and plant cell lines, preferably a yeast.

34. A cell according to definition 32, wherein the yeast is selected from the group consisting of *Pichia, Candida, Torulopsis, Arxula, Hensenula, Yarrowia, Kluyveromyces, Saccharomyces, Komagataella*, preferably a methylotrophic yeast.

35. A cell according to definition 34, wherein the yeast is *Pichia pastoris, Komagataella pastoris, K. phaffii*, or *K. pseudopastoris*.

36. A cell of any of definitions 32 to 35, which has a higher specific growth rate in the presence of a surplus of carbon source relative to conditions of limited carbon source.

37. Method to identify a carbon source regulatable promoter from eukaryotic cells, comprising the steps of
   a) cultivating eukaryotic cells in the presence of a carbon source in a batch culture under cell growing conditions,
   b) further cultivating the cells in a fed batch culture in the presence of a limited amount of a supplemental carbon source,
   c) providing samples of the cell culture of step a) and b), and
   d) performing transcription analysis in said samples to identify a regulatable promoter that shows a higher transcriptional strength in cells of step b) than in cells of step a).

38. Method according to definition 37, wherein the transcription analysis is quantitative or semi-quantitative, preferably employing DNA microarrays, RNA sequencing and transcriptome analysis.

Specific examples relate to fed-batch fermentation of a recombinant production *P. pastoris* cell line producing reporter proteins, employing a glycerol batch medium and a glucose fed batch medium. Comparative promoter activity studies have proven that the promoter according to the invention may be successfully activated to induce recombinant protein production.

According to a further example, human serum albumin (HSA) was produced as a POI under the control of the glucose-limit induced promoters, and the HSA yield and gene copy number determined.

According to another example, fed-batch cultivation of *P. pastoris* strains expressing HSA under the control of a promoter according to the invention was performed. Induction of the promoter activity under glucose-limiting conditions was found to be even more than 120 fold with pG1, and more than 20 fold with pG6, compared to the repressed state.

Further examples refer to expressing a porcine carboxypeptidase B as model protein under transcriptional control of pG1 and pG6 promoter.

Yet, a further example refers to the expression of an antibody fragment under the transcriptional control of pG1.

A further example proves the functional activity of variants of a promoter according to the invention, such as fragments of pG1 with a length in the range of 300 to 1000 bp. Additional experiments have shown that even shorter fragments of pG1 were functionally active in a similar setting, such as fragments ranging between 200 and 1000 bp, or fragments ranging between 250 and 1000.

The foregoing description will be more fully understood with reference to the following examples. Such examples are, however, merely representative of methods of practicing one or more embodiments of the present invention and should not be read as limiting the scope of invention.

EXAMPLES

Examples below illustrate the materials and methods used to identify new regulatable promoters and to analyze their expression properties in *Pichia pastoris*.

Example 1: Identification of Strong, Efficiently Regulated Genes in *P. pastoris* in Glucose-Limited Conditions In order to identify strong, efficiently regulated genes and their respective promoters of *P. pastoris* in glucose-limit conditions, analysis of gene expression patterns was done using microarrays. *P. pastoris* cells grown in a glycerol batch (surplus of carbon source) were compared to cells which were cultivated in conditions where glucose was growth limiting (chemostat), thereby simulating the course of a protein production process, which is usually done in fed batch mode.

a) Strain

A wild type *P. pastoris* strain (CBS2612, CBS-KNAW Fungal Biodiversity Centre, Centraalbureau voor Schimmelcultures, Utrecht, The Netherlands), which can grow on minimal media without supplements, was used.

b) Cultivation of *P. pastoris*

Fermentations were performed with Minifors reactors (Infors-HT, Switzerland) with a final working volume of 2.5 L.

Following media were used:

$PTM_1$ Trace Salts Stock Solution Contained Per Liter
6.0 g $CuSO_4.5H_2O$, 0.08 g NaI, 3.36 g $MnSO_4.H_2O$, 0.2 g $Na_2MoO_4.2H_2O$, 0.02 g $H_3BO_3$, 0.82 g $CoCl_2$, 20.0 g $ZnCl_2$, 65.0 g $FeSO_4.7H_2O$, 0.2 g biotin and 5.0 ml $H_2SO_4$ (95%-98%).

Glycerol Batch Medium Contained Per Liter
2 g Citric acid monohydrate ($C_6H_8O_7.H_2O$), 39.2 g Glycerol, 20.8 g $NH_4H_2PO_4$, 0.5 g $MgSO_4.7H_2O$, 1.6 g KCl, 0.022 g $CaCl_2.2H_2O$, 0.8 mg biotin and 4.6 ml PTM1 trace salts stock solution. HCl was added to set the pH to 5.

Glycerol Fed-Batch Medium Contained Per Liter
632 g glycerol, 8 g $MgSO_4.7H_2O$, 22 g KCl, and 0.058 g $CaCl_2.2H_2O$.

Chemostat Medium Contained Per Liter
2 g Citric acid monohydrate ($C_6H_8O_7.H_2O$), 99.42 g glucose monohydrate, 22 g $NH_4H_2PO_4$, 1.3 g $MgSO_4.7H_2O$, 3.4 g KCl, 0.02 g $CaCl_2.2H_2O$, 0.4 mg biotin and 3.2 ml PTM1 trace salts stock solution. HCl was added to set the pH to 5.

The dissolved oxygen was controlled at DO=20% with the stirrer speed (500-1250 rpm). Aeration rate was 60 L $h^{-1}$ air, the temperature was controlled at 25° C. and the pH setpoint of 5 was controlled with addition of $NH_4OH$ (25%).

To start the fermentation, 1.5 L batch medium was sterile filtered into the fermenter and *P. pastoris* was inoculated (from an overnight pre-culture in YPG, 180 rpm, 28° C.) with a starting optical density (OD600) of 1. The batch phase of approximately 25 h reached a dry biomass concentration of approximately 20 g/L, it was followed by a 10 h exponential fed batch with glucose medium, leading to a dry biomass concentration of approximately 50 g/L. Then, the volume was reduced to 1.5 L and the chemostat cultivation was started with a feed/harvest rate of 0.15 L $h^{-1}$, resulting in a constant growth rate of µ=0.1. The fermentation was terminated 50 h after the chemostat start.

This fermentation has been performed three times to obtain the biological replicates necessary for reliable microarray analysis.

Carbon limited conditions (no detectable residual glucose) during the chemostat were verified by HPLC analysis of the culture supernatant.

c) Sampling

Samples were taken at the end of the glycerol batch phase and in steady state conditions of the glucose chemostat. Routine sampling as determination of optical density or yeast dry mass, qualitative microscopic inspection and cell viability analysis was done alongside during each fermentation. For microarray analysis, samples were taken and treated as follows: For optimal quenching, 9 mL cell culture broth was immediately mixed with 4.5 mL of ice cold 5% phenol (Sigma) solution (in Ethanol abs.), and aliquoted. Each 2 mL were centrifuged (13200 rpm for 1 minute) in precooled collection tubes (GE healthcare, NJ), supernatant was removed completely and the tubes were stored at −80° C. until RNA purification.

d) RNA purification and sample preparation for microarray hybridization

The RNA was isolated using TRI reagent according to the suppliers instructions (Ambion, US). The cell pellets were resuspended in TRI reagent and homogenized with glass beads using a FastPrep 24 (M.P. Biomedicals, CA) at 5 m $s^{-1}$ for 40 seconds. After addition of chloroform, the samples were centrifuged and the total RNA was precipitated from the aqueous phase by adding isopropanol. The pellet was washed with 70% ethanol, dried and re-suspended in RNAse free water. RNA concentrations were determined by measuring OD260 using a Nanodrop 1000 spectrophotometer (Nano Drop products, DE). Remaining DNA from the samples was removed using the DNA free Kit (Ambion, CA). Sample volume equal to 10 µg RNA was diluted to 50 µL in RNAse free water, then DNAse buffer I and rDNAse I were added and incubated at 37° C. for 30 minutes. After addition of DNAse Inactivation Reagent, the sample was centrifuged and the supernatant was transferred into a fresh tube. RNA concentrations were determined again as described above. Additionally, RNA integrity was analyzed using RNA nano chips (Agilent). To monitor the microarray workflow from amplification and labelling to hybridisation of the samples, the Spike In Kit (Agilent, Product Nr.: 5188-5279) was used as positive control. It contains 10 different polyadenylated transcripts from an adenovirus, which are amplified, labelled and cohybridised together with the own RNA samples. The samples were labelled with Cy 3 and Cy 5 using the Quick Amp Labelling Kit (Agilent, Prod. No.: 5190-0444). Therefore 500 ng of purified sample RNA were diluted in 8.3 µL RNAse free water, 2 µL Spike A or B, and 1.2 µL T7 promoter primer were added. The mixture was denatured for 10 minutes at 65° C. and kept on ice for 5 minutes. Then 8.5 µL cDNA mastermix (per sample: 4 µL 5× first strand buffer, 2 µL 0.1 M DTT, 1 µL 10 mM dNTP mix, 1 µL MMLV-RT, 0.5 µL RNAse out) were added, incubated at 40° C. for 2 hours, then transferred to 65° C. for 15 minutes and put on ice for 5 minutes. The transcription mastermix (per sample: 15.3 µL nuclease free water, 20 µL transcription buffer, 6 µL 0.1 M DTT, 6.4 µL 50% PEG, 0.5 µL RNAse Inhibitor, 0.6 µL inorg. phosphatase, 0.8 µL T7 RNA Polymerase, 2.4 µL Cyanin 3 or Cyanin 5) was prepared and added to each tube and incubated at 40° C. for 2 hours. In order to purify the obtained labelled cRNA, the RNeasy Mini Kit (Qiagen, Cat. No. 74104) was used. Samples were stored at −80° C. Quantification of the cRNA concentration and labelling efficiency was done at the Nanodrop spectrophotometer.

e) Microarray Analysis

In order to identify strong, efficient regulated genes in glucose-limited chemostat cultivations, the three biological sample replicates thereof were compared with the same reference and in one dyeswap each. The reference sample was generated by combining the glycerol batch cultivation samples in equal amounts.

The Gene Expression Hybridisation Kit (Agilent, Cat. No. 5188-5242) was used for hybridisation of the labelled sample cRNAs. For the preparation of the hybridisation samples each 300 ng cRNA (Cy3 and Cy 5) and 6 µL 10-fold blocking agent were diluted with nuclease free water to a final volume of 24 µL. After addition of 1 µL 25-fold fragmentation buffer, the mixture was incubated at 60° C. for 30 minutes. Then 25 µL GEx Hybridisation Buffer HI-RPM was added to stop the reaction. After centrifugation for one minute with 13,200 rpm, the sample was chilled on ice and used for hybridisation immediately. In-house designed *P. pastoris* specific oligonucleotide arrays (AMAD-ID: 026594, 8×15K custom arrays, Agilent) were used. Microarray hybridisation was done according to the Microarray Hybridisation Chamber User Guide (Agilent G2534A). First, the gasket slide was uncovered and put onto the chamber base, Agilent label facing up. The sample (40 µL per array) was loaded in the middle of each of the eight squares. Then the microarray slide was carefully put onto the gasket slide (Agilent label facing down) and the chamber cover was placed on and fixed with the clamp. Hybridisation was done in the hybridisation oven for 17 hours at 65° C. Before scanning, the microarray chip was washed. Therefore, the chamber was dismantled, and the sandwich slides were detached from each other while submerged in wash buffer 1. The microarray was directly transferred into another dish with wash buffer 1, washed for 1 minute, transferred into wash buffer 2 (temperature at least 30° C.) and washed for another minute. After drying of the microarray slide by touching the slide edge with a tissue, it was put into the slide holder (Agilent label facing up). The slide holder was put into the carousel and scanning was started.

f) Data Acquisition and Statistical Evaluation of Microarray Data

Images were scanned at a resolution of 50 nm with a G2565AA Microarray scanner (Agilent) and were imported into the Agilent Feature Extraction 9.5 software. Agilent Feature Extraction 9.5 was used for the quantification of the spot intensities. The raw mean spot intensity data was then imported into the open source software R for further normalisation and data analysis.

For data preprocessing and normalization the R packages limma, vsn and marray were used. The intensity data was not background corrected and normalized with VSN, after normalization it was transformed into log 2 ratios of the Cy5 channel against the Cy3 channel. Differential expression was calculated using the lmfit and eBayes function of the limma package.

The microarray data was browsed for entries with both, high difference in expression level between repressed to induced state (fold change) as well as high signal intensity in the induced state in order to identify strongly expressed, efficiently regulated genes. A list of the selected genes is shown in Table 1, with the fold change meaning the signal intensity in the induced state divided by the signal intensity in the repressed state. The data of pGAP and pMLS1, pICL1 are added as references.

TABLE 1

Microarray data of the promoters selected for further characterization and of pGAP, ICL1 and MLS1 as controls

| name | annotation/ yeast homolog | gene identifier | Fold-change | Intensity* | % of intensity/ transcription strength |
|---|---|---|---|---|---|
| pGAP | TDH3 | PAS_chr2-1_0437 | 0.79 | 41052.5 | 100.0 |
| pG1 | — | PAS_chr1-3_0011 | 29.86 | 86312.9 | 210.2 |
| pG3 | YPR127W | PAS_chr4_0550 | 2.66 | 15644.4 | 38.1 |
| pG4 | — | PAS_chr4_0043 | 2.57 | 15664.8 | 38.2 |
| pG6 | ALD4 | PAS_chr2-1_0853 | 2.10 | 26888.4 | 65.5 |
| MLS1 | MLS1 | PAS_chr4_0191 | 0.81 | 1446.9 | 3.5 |
| ICL1 | ICL1 | PAS_chr1-4_0338 | 1.71 | 2574.3 | 6.3 |
| pG7 | HXT6 | PAS_chr1-4_0570 | 3.3 | 13336.5 | 32.5 |
| pG8 | SFL1 | PAS_chr1-3_0165 | 2.1 | 9929.1 | 24.2 |

*of induced state in green channel

Example 2: Comparative Promoter Activity Studies of the Newly Identified Promoters in *P. pastoris* Using eGFP as Intracellularly Expressed Reporter Gene In order to analyze the properties of the newly identified promoters under glucose limit conditions, shake flask screenings were performed as follows: Pre-culture for 24 hours was done with rich medium containing glycerol as carbon source—simulating the batch phase of the process (repressed state of the promoters), which was followed by the main culture with minimal medium and glucose feed beads—simulating the glucose-limited fed batch phase of the process (induced state of the promoters).

a) Strain & Expression Vector

The *P. pastoris* wild type strain (CBS2612, CBS-KNAW Fungal Biodiversity Centre, Centraalbureau voor Schimmelcultures, Utrecht, The Netherlands) was used as host strain. Transformation of the strain was carried out with an in-house vector named pPUZZLE (Stadlmayr et al. J. Biotechnol 2010 December; 150(4):519-29), comprising of an origin of replication for *E. coli* (pUC19), an antibiotic resistance cassette (Sh ble gene conferring resistance to Zeocin) for selection in *E. coli* and yeast, an expression cassette for the gene of interest (GOI) consisting of a multiple cloning site and the *S. cerevisiae* CYC1 transcription terminator, and a locus for integration into the *P. pastoris* genome (3. AOX1 region).

b) Amplification and Cloning of the Newly Identified Promoters pG1, pG3, pG4 and pG6 into pPUZZLE Expression Vector Containing eGFP as 001

A list of the newly identified promoter sequences and their respective genes (see Example 1) is shown in Table 2. 1000 bp of the 5'-non coding region of the respective genes up to the start codon ATG were amplified by PCR (Phusion Polymerase, New England Biolabs) as promoter sequences using the primers shown in Table 2. These sequences were cloned into the pPUZZLE expression vector pPM1aZ10_eGFP, resulting in pPM1aZ10_pG1_eGFP, pPM1aZ10_pG3_eGFP, pPM1aZ10_pG4_eGFP and pPM1aZ10_pG6_eGFP. Additionally, the vector pPM1aZ10_pGAP_eGFP, containing the commonly used promoter of glyceraldehyde 3-phosphate dehydrogenase promoter (pGAP of *P. pastoris*, here SEQ ID 25) was used as reference. The promoters were inserted upstream of the start codon of the eGFP gene using the ApaI and the SbfI restriction sites (see Tables 2 and 3). The correctness of the promoter sequences was verified by Sanger sequencing.

TABLE 3

Amplification primers, cloning enzymes and the length of the cloned promoters

| promoter | 5'primer | 3'primer | Cloning enzyme 5' | Cloning enzyme 3' | Fragment length |
|---|---|---|---|---|---|
| pG1 | pG1_fw | pG1_back | ApaI | SbfI | 988 |
| pG3 | pG3_fw | pG3_back | ApaI | SbfI | 1011 |
| pG4 | pG4_fw | pG4_back | ApaI | SbfI | 1022 |
| pG6 | pG6_fw | pG6_back | ApaI | SbfI | 1022 |
| pG7 | pG7_fw | pG7_back | ApaI | SbfI | 1022 |
| pG8 | pG8_fw | pG8_back | ApaI | SbfI | 1022 | c) Expression of eGFP in *P. pastoris* for Analysis of the Promoter Activity

All plasmids were linearized with AscI within the 3'AOX genome integration region prior to electroporation (2 kV, 4 ms, GenePulser, BioRad) into electrocompetent *P. pastoris*.

Selection of positive transformants was performed on YPD plates (per liter: 10 g yeast extract, 20 g peptone, 20 g

TABLE 2

Primers for PCR amplification of the promoters

| Name | Target | Sequence | $T_M$ | Restriction site |
|---|---|---|---|---|
| pG1_fw | pG1 | SEQ ID 14<br>GATAGGGCCCCAAACATTTGCT<br>CCCCCTAGTCTC | 70.8 | ApaI |
| pG1_back | pG1 | SEQ ID 15<br>GATACCTGCAGGAAGGGTGGAA<br>TTTTAAGGATCTTTTAT | 69.8 | SbfI |
| pG3_fw | pG3 | SEQ ID 16<br>GATAGGGCCCCAGCAATCCAGT<br>AACCTTTTCTGAAT | 70.4 | ApaI |
| pG3_back | pG3 | SEQ ID 17<br>GATACCTGCAGGTTGAGTTCAAT<br>AAATTGTCCGGGA | 70.2 | SbfI |
| pG4_fw | pG4 | SEQ ID 18<br>GATAGGGCCCTGGACTGTTCAAT<br>TTGAAGTCGATG | 70.4 | ApaI |
| pG4_back | pG4 | SEQ ID 19<br>GATACCTGCAGGGGATAAAGGTA<br>AGGGAAAAAAGCAA | 70 | SbfI |
| pG6_fw | pG6 | SEQ ID 20<br>GATAGGGCCCAGACCAGCAGTTT<br>AACTACGCAAATC | 70.6 | ApaI |
| pG6_back | pG6 | SEQ ID 21<br>GATACCTGCAGGCTTTTCTTTGGG<br>CAAGGAAAAATC | 70.7 | SbfI |
| pG7_fw | pG7 | SEQ ID 22<br>GATAGGGCCCAATTGATTAAGTTCAGT<br>GAAATTTCAAAC | 69.1 | ApaI |
| pG7_back | pG7 | SEQ ID 23<br>GATACCTGCAGGATTATATTATGGGGA<br>ATAATGAAGAGAAGG | 70.9 | SbfI |
| pG8_fw | pG8 | SEQ ID 24<br>GATAGGGCCCCTGCACAACCATTGCC<br>AGTAAGG | 71.5 | ApaI |
| pG8_back | pG8 | SEQ ID 25<br>GATACCTGCAGGTTTTTAGAAGAGGG<br>AGAACTTAGATTGG | 70.4 | SbfI | glucose, 20 g agar-agar) plates containing 25 µg/mL of Zeocin (Invivogen, CA). Colony PCR was used to ensure the presence of the transformed plasmid. Therefore, genomic DNA was gained by cooking and freezing of *P. pastoris* colonies for 5 minutes each and directly applied for PCR with the appropriate primers. For expression screening, a single colony was inoculated in liquid YPG-Zeo medium (per liter: 20 g peptone, 10 g yeast extract, 12.6 g glycerol and 25 mg Zeocin) as pre-culture. After approximately 24 h the pre-culture was used to inoculate the main culture with an OD600 of 0.1 in 10 ml YP medium (per liter: 20 g peptone, 10 g yeast extract) and 2 glucose feed beads (Kuhner, CH). Glucose-limiting growth conditions were achieved due to the slow glucose release kinetics of these feed beads, which is described by the following equation: (Glucose)=1.63*t0.74 [mg/Disc]. Samples were taken at the end of the pre-culture, and 24 and 48 hours after inoculation of the main culture. Cell density was determined by measuring OD600, eGFP expression was analyzed by flow cytometry as described in Stadlmayr et al. (J. Biotechnology 2010 December; 150(4):519-29). For each sample 10,000 cells were analyzed. Auto-fluorescence of *P. pastoris* was measured using untransformed *P. pastoris* wild type cells and subtracted from the signal. Relative eGFP expression levels (fluorescence intensity related to cell size) are shown as percentage of eGFP expression level of a clone expressing eGFP under the control of the constitutive pGAP promoter. Further similar studies are done with the promoters pG7 and pG8. Cloning is done as described in example 2b, except that the wild type *P. pastoris* strain X-33 (Invitrogen) was used for the transformation of pPM1aZ10_pG7_eGFP and pPM1aZ10_pG8_eGFP. Used primers and cloning fragments are listed in Tables 2 and 3. The results are shown in Table 4.

TABLE 4

Screening results of eGFP expressing *P. pastoris* clones under the control of the novel promoters; Shown data (Fluorescence/cell size) is related to pGAP;

|  | pre-culture | | main culture | |
| --- | --- | --- | --- | --- |
|  | batch end | stdev | 48 h | stdev |
| pG1 | 7.6 | 0.2 | 242.8 | 59.5 |
| pG3 | −5.1 | 2.4 | 25.4 | 5.5 |
| pG4 | −6.3 | 0.2 | 113.6 | 26.3 |

TABLE 4-continued

Screening results of eGFP expressing *P. pastoris* clones under the control of the novel promoters; Shown data (Fluorescence/cell size) is related to pGAP;

|  | pre-culture | | main culture | |
| --- | --- | --- | --- | --- |
|  | batch end | stdev | 48 h | stdev |
| pG6 | 3.3 | 0.8 | 158.9 | 146.9 |
| pG7 | 49.4 | 7.4 | 115.7 | 16.2 |
| pG8 | 0.8 | 4.1 | 36.1 | 21.1 | d) Determination of eGFP Gene Copy Numbers (GCN) in Selected eGFPexpressing Clones Expression strength is often correlated to the number of expression cassettes integrated into the *P. pastoris* genome. Therefore the gene copy number of eGFP was determined. Genomic DNA was isolated using the DNeasy Blood&Tissue Kit (Quiagen, Cat. No. 69504). Gene copy numbers were determined using quantitative PCR. Therefore, SensiMix SYBR Kit (Bioline, QT605-05) was used. The Sensi Mix SYBR was mixed with the primers and the sample and applied for real time analysis in a real-time PCR cycler (Rotor Gene, Qiagen). A list of the primers is shown in Table 5. All samples were analyzed in tri- or quadruplicates. Rotor Gene software was used for data analysis. The actin gene ACT1 was used as calibrator. Results are shown in Table 6.

TABLE 5

Primers for gene copy nuber determination by real-time PCR

| primer | target | sequence | $T_M$ [° C.] | product lengh |
| --- | --- | --- | --- | --- |
| PpACT1_Up | Act | SEQ ID 26 CCTGAGGCTTTGTTCC ACCCATCT | 61.3 | 148 bp |
| PpACT1_Low | Act | SEQ ID 27 GGAACATAGTAGTACC ACCGGACATAACGA | 61.4 | 148 bp |
| PpeGFP_Up | GFP | SEQ ID 28 TCGCCGACCACTACCA GCAGAA | 61.4 | 124 bp |
| PpeGFP_Low | GFP | SEQ ID 29 ACCATGTGATCGCGCT TCTCGTT | 61.6 | 124 bp |

TABLE 6

Screening results (fluorescence/cell size related to pGAP) and gene copy numers of chosen *P. pastoris* clones expressing eGFP under the control of pG1 and pG6;

|  |  | % of pGAP_eGFP fluorescence/size | | |
| --- | --- | --- | --- | --- |
|  |  |  | main culture | |
|  | GCN | pre culture | 24 h | 48 h |
| pG1#8 | 1 | 7.32 | 33.00 | 184.30 |
| pG1#9 | 1 | 7.73 | 33.96 | 303.21 |
| pG1#12 | 2 | 7.75 | 33.32 | 240.92 |
| pG6#48 | 1 | 3.45 | 2.07 | 56.11 |
| pG6#50 | 2 | 4.00 | 23.18 | 327.14 |
| pG6#53 | 1 | 2.52 | 9.78 | 93.51 | e) Analysis of pG1 Promoter Strength in Fed-Batch Fermentation of One eGFP Clone Fed batch fermentations were performed in DASGIP reactors with a final working volume of 0.7 L.

Following media were used:

PTM$_1$ Trace Salts Stock Solution Contained Per Liter 6.0 g CuSO$_4$.5H$_2$O, 0.08 g NaI, 3.36 g MnSO$_4$.H$_2$O, 0.2 g Na$_2$MoO$_4$.2H$_2$O, 0.02 g H$_3$BO$_3$, 0.82 g CoCl$_2$, 20.0 g ZnCl$_2$, 65.0 g FeSO$_4$.7H$_2$O, 0.2 g biotin and 5.0 ml H$_2$SO$_4$ (95%-98%).

Glycerol Batch Medium Contained Per Liter 2 g Citric acid monohydrate (C$_6$H$_8$O$_7$.H$_2$O), 39.2 g Glycerol, 12.6 g NH$_4$H$_2$PO$_4$, 0.5 g MgSO$_4$.7H$_2$O, 0.9 g KCl, 0.022 g CaCl$_2$.2H$_2$O, 0.4 mg biotin and 4.6 ml PTM1 trace salts stock solution. HCl was added to set the pH to 5.

Glucose Fed Batch Medium Contained Per Liter 464 g glucose monohydrate, 5.2 g MgSO$_4$.7H2O, 8.4 g KCl, 0.28 g CaCl$_2$.2H$_2$O, 0.34 mg biotin and 10.1 mL PTM1 trace salts stock solution.

The dissolved oxygen was controlled at DO=20% with the stirrer speed (400-1200 rpm). Aeration rate was 24 Lh$^{-1}$ air, the temperature was controlled at 25° C. and the pH setpoint of 5 was controlled with addition of NH$_4$OH (25%).

To start the fermentation, 400 mL batch medium was sterile filtered into the fermenter and *P. pastoris* clone pG1_eGFP# 8 was inoculated (from pre-culture) with a starting optical density (OD600) of 1. The batch phase of approximately 25 h (reaching a dry biomass concentration of approximately 20 g/L) was followed by a glucose-limited fed batch starting with an exponential feed for 7 h and a constant feed rate of 15 g/L for 13 h, leading to a final dry biomass concentration of approximately 100 g/L. Samples were taken during batch and fed batch phase, and analyzed for eGFP expression using a plate reader (Infinite 200, Tecan, CH). Therefore, samples were diluted to an optical density (OD600) of 5. Results are shown in Table 7 as relative fluorescence per bioreactor (FL/r).

TABLE 7

Relative fluorescence per bioreactor of two different *P. pastoris* clones expressing eGFP under the control of pGAP or pG1 in an optimized fed batch fermentation.

| pGAP_eGFP#2 | | pG1_eGFP#8 | |
| --- | --- | --- | --- |
| t [h] | FL/r | t [h] | FL/r |
| −1.7 | 176.77 | −0.38 | 131.95 |
| 0.0 | 166.52 | 0.00 | 108.76 |
| 0.5 | 199.59 | 0.28 | 100.35 |
| 1.0 | 195.94 | 0.62 | 121.36 |
| 1.5 | 173.68 | 1.12 | 161.16 |
| 2.0 | 219.00 | 1.62 | 162.69 |
| 3.0 | 321.14 | 2.12 | 148.34 |
| 7.0 | 494.60 | 3.12 | 205.20 |
| 19.1 | 1150.96 | 7.12 | 373.08 |
| 20.0 | 1000.37 | 19.70 | 1745.65 |
| | | 21.12 | 1831.52 |

Example 3: Comparative Promoter Activity Studies of the Newly Identified Promoters in *P. pastoris* Using Human Serum Albumin (HSA) as Extracellular Expressed Reporter Gene In order to analyze the properties of the newly identified promoters under glucose limit conditions, shake flask screenings were performed as follows: Pre-culture for 24 hours was done with rich medium containing glycerol as carbon source—simulating the batch phase of the process (repressed state of the promoters), which was followed by the main culture with minimal medium and glucose feed beads—simulating the glucose-limited fed batch phase of the process (induced state of the promoters).

a) Strain & Expression Vector

The *P. pastoris* wild type strain (CBS2612, CBS-KNAW Fungal Biodiversity Centre, Centraalbureau voor Schimmelcultures, Utrecht, The Netherlands) was used as host strain. Transformation of the strain was carried out with an in-house vector named pPUZZLE (Stadlmayr et al. J. Biotechnol 2010 December; 150(4):519-29), selection of positive transformants was based on the Zeocin resistance. For secretory expression of human serum albumin (HSA) its native secretion leader was used.

b) Amplification and Cloning of the Newly Identified Promoters pG1, pG3, pG4 and pG6 into an in-House Expression Vector The four promoters amplified in Example 2b were cloned into the pPUZZLE expression vector pPM1aZ10_HSA, resulting in pPM1aZ10_pG1_HSA, pPM1aZ10_pG3_HSA, pPM1aZ10_pG4_HSA and pPM1aZ10_pG6_HSA. Additionally, the vector pPM1aZ10_pGAP_HSA, containing the commonly used promoter of glyceraldehyde 3-phosphate dehydrogenase promoter (pGAP) was used as reference. The promoters were inserted upstream of the start codon of the HSA gene using the ApaI and the SbfI restriction sites (see Table 3). The correctness of the promoter sequences was verified by Sanger sequencing.

c) Expression of HSA in *P. pastoris* Under Control of the Newly Identified Glucose-Limit Induced Promoters All plasmids were linearized using AscI restriction enzyme prior to electroporation (using a standard transformation protocol for *P. pastoris*) into *P. pastoris*. Selection of positive transformants was performed on YPD plates (per liter: 10 g yeast extract, 20 g peptone, 20 g glucose, 20 g agar-agar) plates containing 25 µg/mL of Zeocin. Colony PCR was used to ensure the presence of the transformed plasmid as described in Example 2c.

For HSA expression screening, a single colony was inoculated in liquid YPG-Zeo medium (per liter: 20 g peptone, 10 g yeast extract, 12.6 g glycerol and 25 mg Zeocin) as pre-culture. After approximately 24 h the pre-culture was used to inoculate the main culture with an OD600 of 1 in YP medium (per liter: 20 g peptone, 10 g yeast extract) and glucose feed beads (Kuhner, CH). Glucose-limiting growth conditions were achieved due to the slow glucose release kinetics of these feed beads, which is described by the following equation: (Glucose)=$1.63*t^{0.74}$ [mg/Disc]. Samples were taken at the end of the pre-culture, and 24 and 48 hours after inoculation of the main culture. Biomass concentration was determined by measuring OD600 or wet cell weight. HSA concentration in the culture supernatant was quantified by the Human Albumin ELISA Quantitation Set (Cat. No. E80-129, Bethyl Laboratories, Tex., USA) following the supplier's instruction manual. The HSA standard was used with a starting concentration of 400 ng mL$^{-1}$. Samples were diluted accordingly in sample diluent (50 mM Tris-HCl, 140 mM NaCl, 1% (w/v) BSA, 0.05% (v/v) Tween20, pH 8.0). HSA titers from screening of several clones of each construct are presented in Table 8.

TABLE 8

Screening results of HSA expressing *P. pastoris* clones under the control of pGAP, pG1 and pG6

| | HSA titer [mg L-1] | |
|---|---|---|
| clone | pre culture | main culture 48 h |
| pGAP_HSA #1 | 6.9 | 9.0 |
| pGAP_HSA #2 | 9.0 | 8.6 |
| pGAP_HSA #3 | 6.6 | 9.2 |
| pGAP_HSA #4 | 18.9 | 20.4 |
| pGAP_HSA #5 | 9.6 | 8.3 |
| pGAP_HSA #6 | 10.8 | 8.8 |
| pG1_HSA #19 | 0.6 | 6.9 |
| pG1_HSA #20 | 0.6 | 6.7 |
| pG1_HSA #21 | 0.1 | 7.0 |
| pG1_HSA #22 | — | — |
| pG1_HSA #23 | 1.3 | 13.5 |
| pG1_HSA #24 | 1.1 | 13.7 |
| pG1_HSA #25 | 0.5 | 8.9 |
| pG1_HSA #26 | 0.5 | 9.2 |
| pG1_HSA #27 | 0.6 | 7.3 |
| pG1_HSA #28 | 0.6 | 6.1 |
| pG1_HSA #29 | 0.6 | 6.4 |
| pG1_HSA #30 | 0.6 | 7.1 |
| pG6_HSA #31 | 0.3 | 1.8 |
| pG6_HSA #32 | 0.3 | 1.7 |
| pG6_HSA #33 | 0.3 | 2.0 |
| pG6_HSA #34 | 0.4 | 2.0 |
| pG6_HSA #35 | 0.2 | 2.2 |
| pG6_HSA #36 | 0.3 | 2.5 |
| pG6_HSA #37 | 0.3 | 2.3 |
| pG6_HSA #38 | 0.2 | 1.5 |
| pG6_HSA #39 | 0.7 | — |
| pG6_HSA #40 | 0.2 | 2.4 |
| pG6_HSA #41 | 0.4 | — |
| pG6_HSA #42 | — | 1.9 | d) Determination of HSA Gene Copy Numbers

Genomic DNA isolation and qPCR measurement were performed as in Example 2d, using the primers given in Table 9. Results are shown in Table 10.

TABLE 9

Primers for gene copy nuber determination by real-time PCR

| primer | target | sequence | product length |
|---|---|---|---|
| PpACT1_Up | Act | SEQ ID 30<br>CCTGAGGCTTTGTTCCACCCATCT | 148 bp |
| PpACT1_Low | Act | SEQ ID 31<br>GGAACATAGTAGTACCACCGGACATAACGA | 148 bp |
| PpHSA_Up | HSA | SEQ ID 32<br>AAACCTAGGAAAAGTGGGCAGCAAATGT | 135 bp |
| PpHSA_Low | HSA | SEQ ID 33<br>ACTCTGTCACTTACTGGCGTTTTCTCATG | 135 bp |

TABLE 10

Screening and gene copy numer results of chosen *P. pastoris* clones expressing HSA under the control of pGAP, pG1 and pG6;

| Clone | GCN | HSA mgL$^{-1}$ main culture | HSA mgL$^{-1}$ per GCN main culture | Mean | STDEV |
|---|---|---|---|---|---|
| pGAP_HSA#3 | 1 | 9.2 | 9.2 | 9.22 | 0.95 |
| pGAP_HSA#4 | 2 | 20.4 | 10.2 | | |
| pGAP_HSA#5 | 1 | 8.3 | 8.3 | | |
| pG1_HSA#20 | 1 | 6.6 | 6.6 | 6.81 | 0.13 |
| pG1_HSA#21 | 1 | 7.0 | 7.0 | | |
| pG1_HSA#23 | 2 | 13.5 | 6.8 | | |
| pG1_HSA#24 | 2 | 13.7 | 6.8 | | |
| pG6_HSA#36 | 1 | 2.5 | 2.5 | 2.07 | 0.52 |
| pG6_HSA#37 | 1 | 2.3 | 2.3 | | |
| pG6_HSA#38 | 1 | 1.5 | 1.5 | | | e) Fed-Batch Cultivation of *P. pastoris* Strains Expressing HSA Under Control of the pG1 and pG6 Promoter The fermentations were performed in DASGIP bioreactors with a final working volume of 0.7 L. The strain pG1_HSA# 23 had two HSA gene copies, the strain pG6_HSA# 36 carried only one HSA gene copy. Therefore two different *P. pastoris* strains expressing HSA under control of pGAP (pGAP_HSA# 3 having one HSA gene copy, and pGAP_HSA# 4 having two HSA gene copies) were cultivated as reference. All fermentations were performed in duplicates.

Following media were used:

PTM$_1$ Trace Salts Stock Solution Contained Per Liter 6.0 g CuSO$_4$.5H$_2$O, 0.08 g NaI, 3.36 g MnSO$_4$.H$_2$O, 0.2 g Na$_2$MoO$_4$.2H$_2$O, 0.02 g H$_3$BO$_3$, 0.82 g CoCl$_2$, 20.0 g ZnCl$_2$, 65.0 g FeSO$_4$.7H$_2$O, 0.2 g biotin and 5.0 ml H$_2$SO$_4$ (95%-98%).

Glycerol Batch Medium Contained Per Liter 39.2 g Glycerol, 27.9 g H$_3$PO$_4$ (85%), 7.8 g MgSO$_4$.7H$_2$O, 2.6 g KOH, 9.5 g K$_2$SO$_4$, 0.6 g CaSO$_4$.2H2O, 0.4 mg biotin and 4.6 ml PTM1 trace salts stock solution. The pH was adjusted to 5.85 after sterile filtering into the fermenter.

Glucose Fed Batch Medium Contained Per Liter 550 g glucose monohydrate, 6.5 g MgSO$_4$.7H$_2$O, 10 g KCl, 0.35 g CaCl$_2$.2H$_2$O, 0.4 mg biotin and 12 ml PTM1 trace salts stock solution.

The dissolved oxygen was controlled at DO=20% with the stirrer speed (400-1200 rpm). Aeration rate was 24 l h$^{-1}$ air, the temperature was controlled at 25° C. and the pH setpoint of 5.85 was controlled with addition of NH$_4$OH (25%).

To start the fermentation, 400 ml batch medium was sterile filtered into the fermenter and *P. pastoris* was inoculated (from pre-culture) with a starting optical density (OD600) of 1. The batch phase of approximately 25 h reached a dry biomass concentration of approximately 20 g/L and it was followed by a constant fed batch (for 100 hours) with glucose medium, leading to a dry biomass concentration of approximately 100 g/L. The pH was 5.85 during batch, and kept at 5.85 throughout the fermentation. Samples were taken during batch and fed batch phase. HSA concentration was quantified using the Human Albumin ELISA Quantitation Set (Bethyl, Cat. No. E80-129) as described in Example 3c. Biomass concentration and HSA titers are shown in Table 11, the product yield (amount of HSA secreted per biomass, HSA/YDM) at the end of the batch (repressing conditions for pG1 and pG6) and the end of the fed batch (inducing conditions for pG1 and pG6) are given in Table 12. Thereby the induction strategy could be verified. pG1 and pG6 are repressed under carbon source surplus (in glycerol batch), showing nearly no detectable HSA in contrast to the pGAP driven clones. Induction of pG1 and pG6 occurred with the switch to C-limited conditions with the start of the fed batch phase. Induction of pG1 (HSA/YDM) was more than 120-fold compared to the repressed state, induction of pG6 was more than 20-fold compared to the repressed state, while nearly no change was observed for pGAP (3-fold increase in HSA/YDM compared to batch phase).

TABLE 11

Yeast dry mass and HSA titers at batch end and fed batch end of 7 fermentations of P. pastoris clones expressing HSA under the control of pGAP, pG1 or pG6.

| | | Batch end | | | Fed batch end | | |
|---|---|---|---|---|---|---|---|
| CLONE | Fermentation # | time [h] | YDM [gL$^{-1}$] | HSA titer [mgL$^{-1}$] | time [h] | YDM [gL$^{-1}$] | HSA titer [mgL$^{-1}$] |
| pG1#23 | A041 | −1.1 | 24.7 | 0.5 | 99.6 | 125.3 | 328.6 |
| pG1#23 | A048 | −0.3 | 23.9 | 0.5 | 108.4 | 128.6 | 277.6 |
| pG6#36 | A045 | −0.1 | 23.5 | 0.3 | 104.7 | 125.2 | 21.8 |
| pG6#36 | A049 | −0.3 | 24.4 | 0.3 | 108.4 | 129.0 | 26.9 |
| pGAP#4 | A044 | −0.1 | 23.6 | 11.2 | 104.7 | 129.1 | 141.4 |
| pGAP#4 | A051 | −0.9 | 24.1 | 9.0 | 96.9 | 118.2 | 114.9 |
| pGAP#3 | A050 | −0.9 | 24.2 | 5.0 | 96.9 | 117.7 | 57.8 |

TABLE 12

HSA titer per yeast dry mass at batch end and fed batch end of 7 fermentations of P. pastoris clones expressing HSA under the control of pGAP, pG1 or pG6.

| | | end of batch | | end of fed batch | | |
|---|---|---|---|---|---|---|
| | GCN HSA | mean HSA/YDM | SD | mean HSA/YDM | SD | fold induction |
| pG1#23 | 2 | 0.02 | 0.00 | 2.39 | 0.33 | 121.06 |
| pG6#36 | 1 | 0.01 | 0.00 | 0.19 | 0.02 | 21.39 |
| pGAP#4 | 2 | 0.42 | 0.07 | 1.03 | 0.09 | 3.16 |
| pGAP#3 | 1 | 0.21 | | 0.49 | | |

Example 4: Comparative Promoter Activity Studies in Various Glucose Concentrations of the Newly Identified Promoters in P. pastoris Using eGFP as Intracellular Expressed Reporter Gene In order to analyze the properties of the newly identified promoters in various glucose concentrations, shake flask screenings were performed as follows: Pre-culture for 24 hours was done with rich medium containing glycerol as carbon source (repressed state of the promoters), which was followed by the main culture with minimal medium and glucose as carbon source (induced state of the promoters);

a) Strain & Expression Vector

The P. pastoris wild type strain (CBS2612, CBS-KNAW Fungal Biodiversity Centre, Centraalbureau voor Schimmelcultures, Utrecht, The Netherlands) is used as host strain. Transformation of the strain was carried out with an in-house vector named pPUZZLE (Stadlmayr et al. J. Biotechnol 2010 December; 150(4):519-29), selection of positive transformants was based on the Zeocin resistance.

b) Amplification and Cloning of the Newly Identified Promoters pG1, pG3, pG4 and pG6 into pPUZZLE Expression Vector Containing eGFP as GOI Amplification and cloning is done as described in example 2.

c) Expression of eGFP in P. pastoris for Analysis of the Promoter Activity

Transformation and clone selection is done as described in Example 2.

For expression screening, a single colony is inoculated in liquid YPG-Zeo medium (per liter: 20 g peptone, 10 g yeast extract, 12.6 g glycerol and 25 mg Zeocin) as pre-culture. After approximately 24 h the pre-culture is used to inoculate the main culture with an OD600 of 0.01 in 10 ml YP medium (per liter: 20 g peptone, 10 g yeast extract) and glucose as carbon source. Glucose is used in various concentrations from 20 to 0.001 g L$^{-1}$.

Samples are taken after 1-8 hours after inoculation of the main culture. eGFP expression is analyzed by flow cytometry as described in Stadlmayr et al. (J. Biotechnology 2010 December; 150(4):519-29), selection of positive transformants is based on the Zeocin resistance. For each sample 10,000 cells are analyzed. Auto-fluorescence of P. pastoris is measured using untransformed P. pastoris wild type cells.

Example 5: Comparative Promoter Activity Studies of the Newly Identified Promoters in P. pastoris Using Porcine Carboxypeptidase B (CpB) as Extracellular Expressed Reporter Gene In order to analyze the properties of the newly identified promoters under glucose limit conditions, shake flask screenings is performed as follows: Pre-culture for 24 hours is done with rich medium containing glycerol as carbon source—simulating the batch phase of the process (repressed state of the promoters), which is followed by the main culture with minimal medium and glucose feed beads—simulating the glucose-limited fed batch phase of the process (induced state of the promoters);

a) Strain & Expression Vector

The P. pastoris wild type strain (CBS2612, CBS-KNAW Fungal Biodiversity Centre, Centraalbureau voor Schimmelcultures, Utrecht, The Netherlands) is used as host strain. Transformation of the strain is carried out with an in-house vector named pPUZZLE (Stadlmayr et al. J. Biotechnol 2010 December; 150(4):519-29), selection of positive transformants is based on the Zeocin resistance. For secretory expression of porcine carboxypeptidase B (CpB) yeast alpha mating factor leader is used.

b) Amplification and Cloning of the Newly Identified Promoters pG1, pG3, pG4 and pG6 into an in-House Expression Vector Two promoters amplified in Example 2b are cloned into the pPUZZLE expression vector pPM1aZ30_aMF_CpB, resulting in pPM1aZ30_pG1_aMF_CpB and pPM1aZ30_pG6_aMF_CpB. Additionally, the vector pPM1dZ30_pGAP_CPB, containing the commonly used promoter of glyceraldehyde 3-phosphate dehydrogenase promoter (pGAP) is used as reference. The promoters are inserted upstream of the start codon of the CpB gene using the ApaI and the SbfI restriction sites The correctness of the promoter sequences is verified by Sanger sequencing.

c) Expression of CpB in *P. pastoris* Under Control of the Newly Identified Glucose-Limit Induced Promoters Plasmids are linearized using SpeI or SapI restriction enzyme prior to electroporation (using a standard transformation protocol for *P. pastoris*) into *P. pastoris*. Selection of positive transformants is performed on YPD plates (per liter: 10 g yeast extract, 20 g peptone, 20 g glucose, 20 g agar-agar) plates containing 25 µg/mL of Zeocin. Colony PCR is used to ensure the presence of the transformed plasmid as described in Example 2c.

For CpB expression screening, a single colony is inoculated in liquid YPG-Zeo medium (per liter: 20 g peptone, 10 g yeast extract, 12.6 g glycerol and 25 mg Zeocin) as pre-culture. After approximately 24 h the pre-culture is used to inoculate the main culture with an OD600 of 1 in YP medium (per liter: 20 g peptone, 10 g yeast extract) and glucose feed beads (Kuhner, CH). Glucose-limiting growth conditions are achieved due to the slow glucose release kinetics of these feed beads, which is described by the following equation: (Glucose)=$1.63*t^{0.74}$ [mg/Disc]. Samples are taken at the end of the pre-culture, and 24 and 48 hours after inoculation of the main culture. Biomass concentration is determined by measuring OD600 or wet cell weight. CpB concentration in the culture supernatant is quantified by an enzymatic assay, based on the conversion of hippuryl-L-arginine to hippuric acid by the CpB. Reaction kinetics are measured by monitoring the absorption at 254 nm at 25° C. using a Hitachi U-2910 Spectrophotometer when the reaction is started. Samples and standards are buffered with assay buffer (25 mM Tris, 100 mM HCl, pH 7.65) and are activated using activation buffer (0.01 mgL-1 Trypsin, 300 mM Tris, 1 µM $ZnCl_2$, pH 7.65). Activation buffer without trypsin is used instead of sample as negative control. The reaction is started by adding the substrate solution (1 mM hippuryl-L-arginine in assay buffer).

d) Fed-Batch Cultivation of *P. pastoris* Strains Expressing CpB Under Control of the pG6 Promoter Fed batch fermentation is done as described in example 3e. The clone pPM1aZ10_pG6_CpB# 4 produced no detectable CpB in the batch and more than 210 mg/L CpB at the end of the fed batch.

Example 6: Comparative Promoter Activity Studies of the Newly Identified Promoters pG1 and pG6 in *P. pastoris* Multicopy Clones Using Human Serum Albumin (HSA) as Extracellular Expressed Reporter Gene In order to analyze the properties of the newly identified promoters under glucose limit conditions, shake flask screenings are performed as follows: Pre-culture for 24 hours is done with rich medium containing glycerol as carbon source—simulating the batch phase of the process (repressed state of the promoters), which is followed by the main culture with minimal medium and glucose feed beads—simulating the glucose-limited fed batch phase of the process (induced state of the promoters);

a) Strain & Expression Vector

The *P. pastoris* wild type strain (CBS2612, CBS-KNAW Fungal Biodiversity Centre, Centraalbureau voor Schimmelcultures, Utrecht, The Netherlands) is used as host strain. Transformation of the strain is carried out with an in-house vector named pPUZZLE (Stadlmayr et al. J. Biotechnol 2010 December; 150(4):519-29), selection of positive transformants is based on the Zeocin resistance. For secretory expression of human serum albumin (HSA) its native secretion leader is used.

b) Amplification and Cloning of the Newly Identified Promoters pG1 and pG6 into an in-House Expression Vector Two promoters amplified in Example 2b are cloned into the pPUZZLE expression vector pPM1nZ30_HSA, resulting in pPM1nZ30_pG1_HSA and pPM1 nZ30_pG6_HSA.

The promoters are inserted upstream of the start codon of the HSA gene using the ApaI and the SbfI restriction sites. The correctness of the promoter sequences is verified by Sanger sequencing.

c) Expression of HSA in *P. pastoris* Under Control of the Newly Identified Glucose-Limit Induced Promoters All plasmids are linearized using AscI restriction enzyme prior to electroporation (using a standard transformation protocol for *P. pastoris*) into *P. pastoris*. Selection of positive transformants is performed on YPD plates (per liter: 10 g yeast extract, 20 g peptone, 20 g glucose, 20 g agar-agar) plates containing 25 µg/mL of Zeocin. Gene copy number amplification is done as described in Marx et al. (FEMS Yeast Res. 2009 December; 9(8):1260-70). Colony PCR is used to ensure the presence of the transformed plasmid as described in Example 2c.

For HSA expression screening, a single colony is inoculated in liquid YPG-Zeo medium (per liter: 20 g peptone, 10 g yeast extract, 12.6 g glycerol and 25 mg Zeocin) as pre-culture. After approximately 24 h the pre-culture is used to inoculate the main culture with an OD600 of 1 in YP medium (per liter: 20 g peptone, 10 g yeast extract) and glucose feed beads (Kuhner, CH). Glucose-limiting growth conditions are achieved due to the slow glucose release kinetics of these feed beads, which is described by the following equation: (Glucose)=1.63*t0.74 [mg/Disc]. Samples are taken at the end of the pre-culture, and 24 and 48 hours after inoculation of the main culture. Biomass concentration is determined by measuring OD600 or wet cell weight. HSA concentration in the culture supernatant is quantified by the Human Albumin ELISA Quantitation Set (Cat. No. E80-129, Bethyl Laboratories, Tex., USA) following the supplier's instruction manual. The HSA standard is used with a starting concentration of 400 ng $mL^{-1}$. Samples are diluted accordingly in sample diluent (50 mM Tris-HCl, 140 mM NaCl, 1% (w/v) BSA, 0.05% (v/v) Tween20, pH 8.0). HSA titers from a screening of several multicopy clones and single copy clones from Example 3c are presented in Table 13.

TABLE 13

Screening results of *P. pastoris* multicopy clones expressing HSA under the control of pGAP, pG1 and pG6

| clone | HSA titer (mg/L) |
| --- | --- |
| pPM1aZ10_pG1_HSA#23 | 8.20 |
| pPM1nZ30_pG1_HSA#C2 | 19.55 |
| pPM1nZ30_pG1_HSA#4*1000 | 21.59 |
| pPM1nZ30_pG1_HSA#5*1000 | 21.33 |
| pPM1nZ30_pG1_HSA#X4 | 27.22 |
| pPM1nZ30_pG1_HSA#X5 | 6.90 |
| pPM1aZ10_pG6_HSA#36 | 1.55 |
| pPM1nZ30_pG6_HSA#C6 | 14.12 |
| pPM1nZ30_pG6_HSA#2*1000 | 15.85 |
| pPM1nZ30_pG6_HSA#X5 | 11.52 |
| pPM1nZ30_pG6_HSA#X8 | 7.87 | d) Determination of HSA Gene Copy Numbers

Genomic DNA isolation and qPCR measurement are performed as in Example 2d, using the primers given in Table 9. Results are shown in Table 14.

TABLE 14

Screening and gene copy numer results of chosen
P. pastoris multicopy clones expressing
HSA under the control of pGAP, pG1 and pG6

| clone | GCN | HSA mgL$^{-1}$ main culture | HSA mgL$^{-1}$ per GCN main culture |
|---|---|---|---|
| pPM1nZ30_pG1_HSA#4*1000 | 11 | 21.59 | 1.89 |
| pPM1nZ30_pG1_HSA#X4 | 17 | 27.22 | 1.64 |
| pPM1nZ30_pG6_HSA#C6 | 12 | 14.12 | 1.23 |
| pPM1nZ30_pG6_HSA#2*1000 | 6 | 15.85 | 2.50 | e) Fed-Batch Cultivation of Multicopy P. pastoris Strains Expressing HSA Under Control of the pG1 and pG6 Promoter Fed batch fermentations are done as described in example 3e. The clones pPM1nZ30_pG1_HSA# 4*1000 and pPM1nZ30_pG6_HSA# C6 reached 1060 and 728 mg/L HSA at the end of the fed batch, respectively.

Example 7: Comparative Promoter Activity Studies of the Newly Identified Promoter pG1 in P. pastoris Using Antibody Fragment (Fab) as Extracellular Expressed Reporter Gene In order to analyze the properties of the newly identified promoters under glucose limit conditions, shake flask screenings is performed as follows: Pre-culture for 24 hours is done with rich medium containing glycerol as carbon source—simulating the batch phase of the process (re-pressed state of the promoters), which is followed by the main culture with minimal medium and glucose feed beads—simulating the glucose-limited fed batch phase of the process (induced state of the promoters);

a) Strain & Expression Vector

The P. pastoris wild type strain (CBS2612, CBS-KNAW Fungal Biodiversity Centre, Centraalbureau voor Schimmelcultures, Utrecht, The Netherlands) is used as host strain. Transformation of the strain is carried out with an in-house vector named pPUZZLE (Stadlmayr et al. J. Biotechnol 2010 December; 150(4):519-29), selection of positive transformants is based on the Zeocin resistance. For secretory expression of an antibody Fab fragment, yeast alpha mating factor leader is used.

b) Amplification and Cloning of the Newly Identified Promoter pG1 into an in-House Expression Vector The pG1 promoter amplified in Example 2b is cloned into the pPUZZLE expression vector containing Fab as GOI as described in example 5b. The promoter is inserted upstream of the start codon of the Fab gene using the ApaI and the SbfI restriction sites. The correctness of the promoter sequence is verified by Sanger sequencing.

c) Expression of Fab in P. pastoris Under Control of the Newly Identified Glucose-Limit Induced Promoter pG1

Plasmids are linearized using SpeI or SapI restriction enzyme prior to electroporation (using a standard transformation protocol for P. pastoris) into P. pastoris. Selection of positive transformants is performed on YPD plates (per liter: 10 g yeast extract, 20 g peptone, 20 g glucose, 20 g agar-agar) plates containing 25 µg/mL of Zeocin. Colony PCR is used to ensure the presence of the transformed plasmid as described in Example 2c.

For Fab expression screening, a single colony is inoculated in liquid YPG-Zeo medium (per liter: 20 g peptone, 10 g yeast extract, 12.6 g glycerol and 25 mg Zeocin) as pre-culture. After approximately 24 h the pre-culture is used to inoculate the main culture with an OD600 of 1 in YP medium (per liter: 20 g peptone, 10 g yeast extract) and glucose feed beads (Kuhner, CH). Glucose-limiting growth conditions are achieved due to the slow glucose release kinetics of these feed beads, which is described by the following equation: (Glucose)=1.63*t$^{0.74}$ [mg/Disc]. Samples are taken at the end of the pre-culture, and 24 and 48 hours after inoculation of the main culture. Biomass concentration is determined by measuring OD600 or wet cell weight. Fab expression levels are quantified by ELISA using Anti-Human Kappa Light Chains (Bound and Free)-Alkaline Phosphatase antibody produced in goat. Fab titers from a screening of several Fab expressing clones under the control of pGAP and pG1 are presented in Table 15.

TABLE 15

Screening results of P. pastoris clones expressing
Fab under the control of pGAP and pG1

| | Fab (mg/L) |
|---|---|
| pPM1dZ30_pGAP_Fab#2 | 0.00 |
| pPM1dZ30_pGAP_Fab#5 | 0.70 |
| pPM1dZ30_pGAP_Fab#7 | 0.68 |
| pPM1aZ30_pG1_Fab#2 | 2.02 |
| pPM1aZ30_pG1_Fab#3 | 0.70 |
| pPM1aZ30_pG1_Fab#4 | 1.10 |
| pPM1aZ30_pG1_Fab#5 | 0.00 |
| pPM1aZ30_pG1_Fab#6 | 0.56 |
| pPM1aZ30_pG1_Fab#9 | 0.66 |
| pPM1aZ30_pG1_Fab#10 | 1.80 |
| pPM1aZ30_pG1_Fab#11 | 1.64 |
| pPM1aZ30_pG1_Fab#12 | 2.31 |
| pPM1aZ30_pG1_Fab#13 | 2.35 |
| pPM1aZ30_pG1_Fab#14 | 2.27 |
| pPM1aZ30_pG1_Fab#15 | 1.60 |
| pPM1aZ30_pG1_Fab#16 | 1.45 |
| pPM1aZ30_pG1_Fab#B9 | 2.89 |
| pPM1aZ30_pG1_Fab#B10 | 2.32 |
| pPM1aZ30_pG1_Fab#B11 | 6.45 |
| pPM1aZ30_pG1_Fab#B12 | 3.24 |
| pPM1aZ30_pG1_Fab#B13 | 2.57 |
| pPM1aZ30_pG1_Fab#B14 | 3.14 |
| pPM1aZ30_pG1_Fab#B15 | 3.23 |
| pPM1aZ30_pG1_Fab#B16 | 2.61 |
| pPM1aZ30_pG1_Fab#C1 | 10.58 |
| pPM1aZ30_pG1_Fab#C2 | 1.46 |
| pPM1aZ30_pG1_Fab#C3 | 12.38 |
| pPM1aZ30_pG1_Fab#C4 | 9.91 |
| pPM1aZ30_pG1_Fab#C5 | 1.96 |
| pPM1aZ30_pG1_Fab#C6 | 2.87 |
| pPM1aZ30_pG1_Fab#C7 | 7.03 |
| pPM1aZ30_pG1_Fab#C8 | 6.37 | d) Fed-Batch Cultivation of P. pastoris Strains Expressing Fab Under Control of the pG1 Promoter.

Fed batch fermentations are done similar as described in example 3e, but glucose fed batch as described in example 2e is used. The clones pPM1aZ30_pG1_Fab# C4 and pPM1aZ30_pG1_Fab# C7 reached 165 and 131 mg/L Fab at the end of the fed batch, respectively.

Example 8: Exponential Fed-Batch Fermentation to Control the Specific Growth Rate at the Maximal Volumetric Productivity of the Newly Identified Promoters Chemostat cultivations of P. pastoris clones expressing a reporter gene under the control of the newly identified promoters are used to determine the specific and volumetric productivity at different growth rates. As described by Maurer et al. (Microb Cell Fact. 2006 Dec. 11; 5:37), exponential fed-batch fermentations can be used to grow a P. pastoris clone at a certain growth rate for improved production during the whole feed phase. Thereby the space-time yield can be optimized. An optimized feed was applied and the space-time yield of the fed batch phase was improved by more than 35%.

Example 9: Determination of Promoter/Transcription Strength: Comparative Promoter Activity Study to Identify Promoter Regulation on Different Glucose Concentrations Using eGFP as Intracellular Expressed Reporter Gene Regulation properties of a promoter are analyzed by screening clones expressing eGFP under the control of said promoter. Therefore, a single colony is inoculated in liquid YPG-Zeo medium (per liter: 20 g peptone, 10 g yeast extract, 12.6 g glycerol and 25 mg Zeocin) as pre-culture. After approximately 24 h the pre-culture is used to inoculate the main culture with an OD600 of 0.01 in 10 ml YP medium (per liter: 20 g peptone, 10 g yeast extract) and glucose in different concentrations (20, 10, 5, 2.5, 1.25, 0.625, 0.313, 0.156, 0.078, 0.039, 0.020, 0.010, 0.005 and 0.002 g/L). A sample is taken after 6 hours and analyzed by flow cytometry as described by Stadlmayr et al. (J Biotechnol. 2010 December; 150(4):519-29). Fluorescence related to cell size (forward scatter to the power of 1.5) is calculated for each cell/data point and the geometric mean thereof is used to compare eGFP expression levels produced in different glucose concentrations. A clone expressing eGFP under the control of pGAP is used as reference (pGAP of P. pastoris, here SEQ ID 25). Auto-fluorescence of P. pastoris is measured using untransformed P. pastoris wild type cells and subtracted from the signal. Table 16 shows the full induction of pG1 promoter at about 40 mg/L glucose or less, and its transcription strength as compared to the native pGAP promoter.

TABLE 16

Relative eGFP expression (related to pGAP) of a P. pastoris clone expressing eGFP under the control of the pG1 promoter in different glucose concentrations (20-0.002 g/L)

| % of pGAP | Glucose (g/L) |
| --- | --- |
| 14.7 | 20 |
| 17.4 | 10 |
| 23.7 | 5 |
| 25.4 | 2.5 |
| 28.2 | 1.25 |
| 30.6 | 0.625 |
| 36.9 | 0.3125 |
| 44.5 | 0.15625 |
| 50.9 | 0.078125 |
| 56.2 | 0.0390625 |
| 55.0 | 0.0195313 |
| 57.5 | 0.0097656 |
| 59.2 | 0.0048828 |
| 59.6 | 0.0024414 |

Further similar studies were made to compare the relative transcription strength of the de-repressed promoters pG1, pG3, pG4, pG6 and pG7. A clone expressing eGFP under the control of one of the promoters was cultivated in YPG (20 g/L glycerol, repressed state) and then inoculated in YP medium containing different amounts of glucose (20 to 0.002 g/L (D20, D10, . . . D0.002), induced state) and cultivated for 5-6 hours. Cells were analyzed by flow cytometry and results were evaluated as follows: The fluorescence was related to cell size (forward scatter to the power of 1.5) for each cell and the geometric mean thereof was used for comparison of different glucose concentrations. The concluding result of these screenings are shown in FIG. 14, a diagram showing the logarithmic glucose concentrations against relative fluorescence, giving a good picture of the induction behaviour of glucose-limit regulatable promoters. FIG. 14 shows the full induction of pG1 promoter at about 40 mg/L glucose or less, and of the promoters pG3, pG4 and pG6 at about 4 g/L or less, and the transcription strength as compared to the native pGAP promoter. The induction behaviour of pG7 is similar to pG1 (Data not shown). Based on the previous results with pG8 it is assumed that its induction behavior is in the range of the other promoters.

Example 10: Comparison of Prior Art pICL1 and pMLS1 Promoters to pG1 in the Glucose Concentration Screening Assay The comparative promoter activity study is performed according to Example 9, employing the pICL1 and pMLS1 promoters as a reference to compare with the pG1 promoter according to the invention.

The activity of both pICL1 and pMLS1 promoters is found to be very weak, with no significant difference at high (D20: 20 g/L/Repression) or low (D0.04: 0.04 g/L Induction=De-Repression) glucose concentration. In any case the activity is far less than the activity of the repressed pG1 promoter in the same setting. Results are shown in Table 17 as promoter activity in % relative to the pGAP promoter.

TABLE 17

Relative fluorescence of strains expressing eGFP under control of pG1, pICL1 and pMLS1, respectively, grown either in medium containing 20 g/L glucose (D20) or 0.04 g/L (D0.04).

| | D20/Repression | D0.04/Induction |
| --- | --- | --- |
| pG1#8 | 9.95 +/− 2.60 | 48.41 +/− 2.76 |
| pICL1 | 2.68 +/− 1.78 | 5.07 +/− 0.90 |
| pMLS1 | −1.26 +/− 0.54 | 0.58 +/− 0.22 |

Example 11: Comparison of Variants of pG1

Shorter variants of the pG1 promoter are cloned as described in example 2a and screened similar as described in example 2c, but in a downscaled setup using 24-well plates (Whatman, UK, Art. Nr. 7701-5110) and quarters of feed beads (12 mm, Kuhner, CH) instead of total ones. Clones expressing under the control of pG1 and pGAP are used as controls. Forward primers and lengths of pG1 and its variants are listed in Table 18. There was no significant difference in the relative fluorescence of cells expressing eGFP under the control of pG1 and the pG1 variants a-f.

TABLE 18 pG1 and its variants: forward primers and 5' start and 3'end positions in the pG1 sequence (SEQ ID 1). Sequences of pG1a-f see FIG. 15 (SEQ ID 41-46).

| promoter | primer | 5' | 3' | Length (bp) |
|---|---|---|---|---|
| pG1 | GATAGGGCCCCAAACATTTGCTCCCCCTAGTCTC<br>SEQ ID 34 | 36 | 1001 | 988 |
| pG1 a | GATAGGGCCCGGAATCTGTATTGTTAGAAAGAACGAG<br>AG<br>SEQ ID 35 | 143 | 1001 | 881 |
| pG1 b | GATAGGGCCCCCATATTCAGTAGGTGTTTCTTGCAC<br>SEQ ID 36 | 338 | 1001 | 686 |
| pG1 c | GATAGGGCCCCTGCAGATAGACTTCAAGATCTCAGG<br>SEQ ID 37 | 509 | 1001 | 515 |
| pG1 d | GATAGGGCCCGACCCCGTTTTCGTGACAAATT<br>SEQ ID 38 | 632 | 1001 | 392 |
| pG1 e | GATAGGGCCCCCGGATAAGAGAATTTTGTTTGATTAT<br>SEQ ID 39 | 674 | 1001 | 350 |
| pG1 f | GATAGGGCCCGCCTGCTCCATATTTTTCCGG<br>SEQ ID 40 | 719 | 1001 | 305 |

---

The invention claimed is:

1. A method of producing a promoter variant which is a variant of a promoter selected from the group consisting of pG1 consisting of the nucleotide sequence of SEQ ID NO: 1, pG3 consisting of the nucleotide sequence of SEQ ID NO: 2, pG4 consisting of the nucleotide sequence of SEQ ID NO: 4, pG6 consisting of the nucleotide sequence of SEQ ID NO: 3, pG7 consisting of the nucleotide sequence of SEQ ID NO: 5, and pG8 consisting of the nucleotide sequence of SEQ ID NO: 6, which method comprises
   a) mutagenesis of the respective promoter nucleotide sequence thereby producing variants comprising a nucleotide sequence of at least 250 bp and having at least 80% sequence identity to the respective promoter nucleotide sequence,
   b) determining the transcription rate of the variants, and
   c) selecting a promoter variant from said variants which is capable of producing a protein of interest (POI) in a recombinant eukaryotic cell by expressing a nucleotide sequence encoding said POI under the transcriptional control of said promoter variant, at a transcription rate of at least 20% as compared to the pGAP promoter (SEQ ID NO:13).

2. The method of claim 1, wherein in step b) the transcription rate of the variants is determined when repressed and de-repressed to select a carbon source regulatable promoter variant.

3. The method of claim 1, wherein the promoter variant is selected which is regulatable by a carbon source such that
   i) it is repressed in a cell when cultivating the cell with a basal carbon source repressing the promoter, wherein the basal carbon source is a carbon source suitable for cell growth; and
   ii) it is de-repressed and fully induced in the cell when cultivating the cell in the presence of 0-1 g/L of a supplemental carbon source.

4. The method of claim 3, wherein
   a) the basal carbon source is selected from the group consisting of glucose, glycerol, ethanol, fructose, galactose, mannose, a disaccharide, and mixtures thereof; and/or
   b) wherein the supplemental carbon source is selected from the group consisting of a hexose, a disaccharide, an alcohol, and mixtures thereof.

5. The method of claim 1, wherein the promoter variant is selected which is de-repressed and fully induced when cultivating the cell using a feed medium which is chemically defined and methanol-free.

6. The method of claim 1, wherein the transcription rate is determined in a cell culture employing a feed medium that provides for a limited amount of the supplemental carbon source, or an amount of 1 g/L or less of the supplemental carbon source in the culture medium.

7. The method of claim 1, wherein in step a) said mutagenesis includes modifying the respective promoter nucleotide sequence by insertion, deletion or substitution of one or more nucleotides within the sequence or at either or both of the distal ends of the sequence.

8. The method of claim 1, wherein in step a) said mutagenesis includes producing fragments of any of the pG1, pG3, pG4, pG7, or pG8 promoter.

9. The method of claim 8, wherein said mutagenesis includes producing fragments of the pG1 promoter which are selected from the group consisting of pG1a consisting of the nucleotide sequence of SEQ ID NO: 41, pG1b consisting of the nucleotide sequence of SEQ ID NO: 42, pG1c consisting of the nucleotide sequence of SEQ ID NO: 43, pG1d consisting of the nucleotide sequence of SEQ ID NO: 44, pG1e consisting of the nucleotide sequence of SEQ ID NO: 45 and pG1f consisting of the nucleotide sequence of SEQ ID NO: 46.

10. The method of claim 1, wherein in step a) said mutagenesis produces variants having at least 90% sequence identity to the respective promoter nucleotide sequence.

11. The method of claim 1, wherein the POI is a heterologous protein selected from the group consisting of therapeutic proteins, antibodies or antigen-binding fragments thereof, enzymes, peptides, protein antibiotics, toxin fusion proteins, carbohydrate-protein conjugates, structural proteins, regulatory proteins, vaccines, vaccine like proteins or particles, process enzymes, growth factors, hormones and cytokines.

12. The method of claim 1, wherein the cell line is selected from the group consisting of mammalian, insect, yeast, filamentous fungi and plant cell lines.

* * * * *